(12) United States Patent
Ryu et al.

(10) Patent No.: US 8,148,541 B2
(45) Date of Patent: Apr. 3, 2012

(54) RHODANINE DERIVATIVES, A PROCESS FOR THE PREPARATION THEREOF AND PHARMACEUTICAL COMPOSITION CONTAINING THE SAME

(75) Inventors: Seong Eon Ryu, Taejeon-si (KR); Seung Jun Kim, Taejeon-si (KR); Dae Gwin Jeong, Taejeon-si (KR); Sang Hyeup Lee, Taejeon-si (KR); Suk Kyeong Jung, Taejeon-si (KR); Hwan Mook Kim, Taejeon-si (KR); Song Kyu Park, Taejeon-si (KR); Ki Ho Lee, Seoul (KR); Chang Woo Lee, Taejeon-si (KR); Joong-Kwon Choi, Taejeon-si (KR); Jin Hee Ahn, Taejeon-si (KR)

(73) Assignee: Korea Research Institute of Bioscience and Biotechnology, Taejeon-Si (KR)

( * ) Notice: Subject to any disclaimer, the term of this patent is extended or adjusted under 35 U.S.C. 154(b) by 598 days.

(21) Appl. No.: 12/087,474

(22) PCT Filed: Dec. 8, 2006

(86) PCT No.: PCT/KR2006/005343
§ 371 (c)(1),
(2), (4) Date: Jul. 8, 2008

(87) PCT Pub. No.: WO2007/081091
PCT Pub. Date: Jul. 19, 2007

(65) Prior Publication Data
US 2009/0042872 A1 Feb. 12, 2009

(30) Foreign Application Priority Data
Jan. 9, 2006 (KR) .................. 10-2006-0002175

(51) Int. Cl.
*C07D 277/04* (2006.01)
*C07D 417/02* (2006.01)
*C07D 413/02* (2006.01)
*A61K 31/535* (2006.01)
*A61K 31/497* (2006.01)
*A61K 31/425* (2006.01)

(52) U.S. Cl. ........ 548/183; 544/133; 544/369; 514/236; 514/254.02; 514/369

(58) Field of Classification Search ........................ None
See application file for complete search history.

(56) References Cited

U.S. PATENT DOCUMENTS

| 5,523,314 A | * | 6/1996 | Bue-Valleskey et al. ..... 514/369 |
| 6,506,755 B2 | * | 1/2003 | Friebe et al. ............. 514/252.05 |
| 2002/0037901 A1 | * | 3/2002 | Friebe et al. ............. 514/252.05 |
| 2002/0049214 A1 | * | 4/2002 | Gibbs et al. ............. 514/253.01 |
| 2005/0288341 A1 | | 12/2005 | Nag et al. |

FOREIGN PATENT DOCUMENTS

| JP | 05306224 A | * | 11/1993 |
| JP | 07173143 A | * | 7/1995 |
| WO | 01/02377 | | 1/2001 |
| WO | WO 0102377 A1 | * | 1/2001 |
| WO | WO0157006 A2 | * | 8/2001 |
| WO | 02/06281 | | 1/2002 |
| WO | 02/072009 | | 9/2002 |
| WO | 03/050098 | | 6/2003 |
| WO | 2004/007491 | | 1/2004 |
| WO | WO 2004080480 A1 | * | 9/2004 |

OTHER PUBLICATIONS

Ahn et al. Bioorg. Med. Chem. Lett., 16 (2006) 2996-2999.*
Lesik et al. Farmatsevtichnii Zhurnal (Kiev) 2003(2) 52-56.*
Makoto Murata et al., *Synthesis and aldose reductase inhibitory activity of a new series of 5-[[2-(ω-carboxyalkoxy)aryl]methylene]-4-oxo-2-thioxothiazolidine derivatives*, 34 Eur. J. Med. Chem. 1061 (1999).
Han Chen et al., *Synthesis and biological evaluation of thiazolidine-2,4-dione and 2,4-thione derivatives as inhibitors of translation initiation*, 14 Bioorganic & Med. Chem. Letters 5401 (2004).

* cited by examiner

*Primary Examiner* — Kamal Saeed
*Assistant Examiner* — Nyeemah A Grazier
(74) *Attorney, Agent, or Firm* — The Nath Law Group; Tanya E. Harkins; Mihsuhn Koh

(57) ABSTRACT

Disclosed herein are rhodanine derivatives, a method for the preparation thereof, and a pharmaceutical composition containing the same. The rhodanine derivatives have inhibitory activity against protein phosphatases (PPase) such as PTP1B, Prl-3, LAR, CD45, Cdc25A, Cdc25B, Cdc25C, Yop, PP1 and VHR, and can be applied for the prevention and treatment of PPase-caused diseases, including autoimmune diseases, diabetes, impaired glucose intolerance, insulin resistance, obesity, cancers, etc. when the inhibitory activity thereof is modulated.

14 Claims, No Drawings

RHODANINE DERIVATIVES, A PROCESS FOR THE PREPARATION THEREOF AND PHARMACEUTICAL COMPOSITION CONTAINING THE SAME

TECHNICAL FIELD

The present invention relates to rhodanine derivatives which inhibit the activity of protein phosphatases (PPase), such as PTP1B (protein tyrosine phosphatase 1B), Prl-3 (phosphatase of regenerating liver), LAR (leukocyte antigen-related), CD45 (cluster of differentiation 45), Cdc25A, Cdc25B, Cdc25C (cell division cycle 25), Yop (*Yersinia enterocolitica* tyrosine phosphatase), PP1 (protein phosphatases 1), VHR (vaccinia human-related) and the like, a method for the preparation thereof and a pharmaceutical composition containing the same or a pharmaceutically acceptable salt thereof as an active ingredient.

BACKGROUND ART

Protein phosphorylation and dephosphorylation are known as important regulatory mechanisms which are used for signal transduction in various stages of the cellular functions. On the whole, cellular signals are mediated through phosphorylation and dephosphorylation, catalyzed by kinases and phosphatases, respectively. Due to their characteristic activities, particularly, protein phosphatases (PPases), which are responsible for dephosphorylation, are known to play pivotal roles in the in vivo modulation and regulation of fundamental cellular signaling mechanisms for metabolism, growth, proliferation and differentiation. Among these protein phosphatases are PTP1B, functioning to remove phosphate from tyrosine, Prl-3, LAR, CD45, Cdc25A, Cdc25B, Cdc25C, Yop, PP1, VHR and the like. Hereinafter, the results of the prior researches related to these PPases will be described.

1. PTP1B

PTP1B as the first identified intracellular protein tyrosine phosphatase, was isolated from the human placenta and found to have molecular weight of ~50 KDa (Tonks et al., *J. Biol. Chem.* 1988, 263, 6722), and then successfully cloned (Charbonneau at al., *Proc. Natl. Acad. Sci. USA* 1989, 86, 5252; Chernoff et al., *Proc. Natl. Acad. Sci. USA* 1989, 87, 2735). PTP1B is highly expressed in various human cells. Particularly, PTP1B acts to inhibit the phosphorylation not only of insulin receptor (IR) but also of insulin receptor substrate (IRS-1) in the signal transduction pathway of insulin. It was demonstrated through the biochemical experiment conducted by Kennedy and Ramachandran, in which PTP1B knock-out mice were observed to exhibit insulin sensitivity and, when injected with insulin, to increase the phosphorylation of insulin receptors in hepatic and muscular cells (*Science* 1999, 283, 1544). Diabetes mellitus type II, a insulin-independent diabetes, is a metabolic disorder that is primarily characterized by insulin resistance of the organs (muscles, liver, lipocytes) where insulin disfunctions, although the pancreas normally secretes insulin. The dephosphorylation of the insulin receptor (IR) was found to be directly responsible for insulin resistance and be implicated in diabetes mellitus type II. Having potential activity to overcome insulin resistance and normalize the level of glucose and insulin in the blood without causing hypoglycemia, accordingly, PTP1B inhibitors, acting against the dephosphorylation of IR, have been extensively studied with the aim of developing therapeutic agents for diabetes mellitus type II.

For example, Wyeth-Ayerst and American Home Products disclosed 10 or more patents in which a broad spectrum of PTP1B inhibitors is described (U.S. Pat. No. 6,121,271, U.S. Pat. No. 6,110,963, U.S. Pat. No. 6,110,962, U.S. Pat. No. 6,103,708, U.S. Pat. No. 6,063,815, U.S. Pat. No. 6,057,316, U.S. Pat. No. 6,001,867, WO 9961436, WO 9961410, WO 9958522, WO 9958521, WO 9958520, WO 9958519, WO 9958518, WO 9958514, WO 9958511), and published many relevant articles (Wrobel, J. et al., *J. Med Chem* 1999, 42, 3199, Malamas, M. S. et al., *J. Med. Chem.* 2000, 43, 995; Malamas, M. S. et al., *J. Med. Chem.* 2000, 43, 1293; Wrobel, J. et al., *Bioorg. & Med. Chem. Lett.* 2000, 10, 1535). Through the above studies of PTP1B inhibitors, new compounds, including benzofuran and benzothiophene biophenyl, were reported to have $IC_{50}$ values of tens of nM. A material which is also able to more effectively reduce the level of glucose in the blood than ciglitazone, which has been widely used as a therapeutic agent for diabetes mellitus, was found through in vivo experiments with mice. Recently, the development of the ertiprotafib, a kind of PTP1B inhibitor, represented by the following structural formulas, has been discontinued in phase II clinical testing.

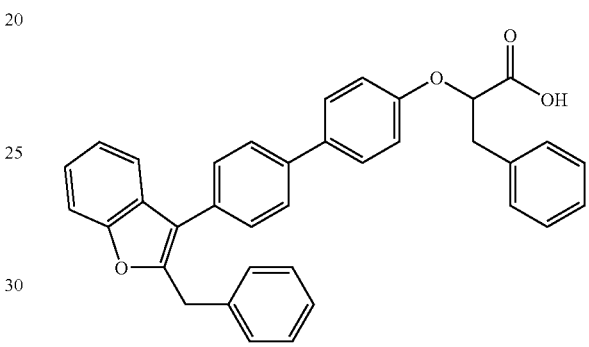

American Home Product WO9958518

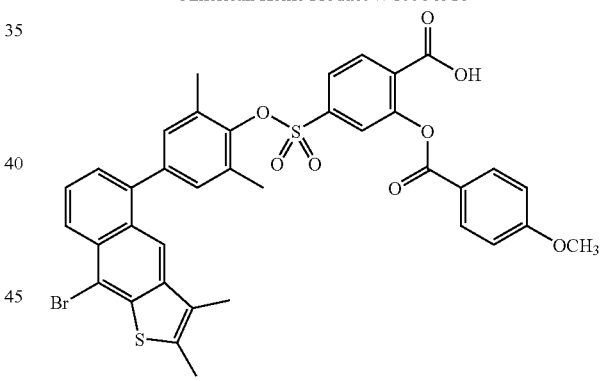

American Home Product WO9958522

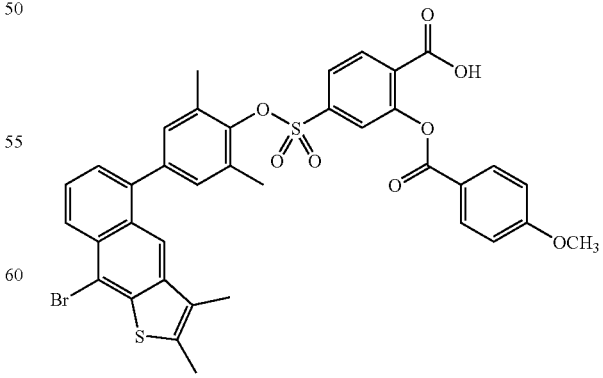

Ertiprotafib, Wyeth-Ayerst

Also, Abbott Company has continuously tried to develop PTP1B inhibitors on the basis of various chemical skeletons. (WO0264840, US 2002-077347, US 2002-072516, Diabetes 2002, 57(8), 2405). Prof. Zhang, Albert Einstein College of Medicine of Yeshiva University, suggested novel structures for PTP1B inhibitors by virtual screening, and also by molecular modeling using PTP1B crystalline structure (Zhang, Z. et al., *J. Biol. chem.* 2002, 277 (35), 31818. *J. Med. Chem.* 2000, 43, 146, *Bioorg. & Med. Chem. Lett.* 2000, 10, 457, *Bioorg. & Med. Chem. Lett.* 2000, 10, 923, *Bioorg. & Med. Chem. Lett.* 1998, 8, 2149, *Bioorg. & Med. Chem. Lett.* 1998, 8, 1799, *Biochemisty* 1999, 38, 3793).

Novo Nordisk/Ontogen Company introduced a low molecular weight oxalylaminoaryl acid derivative, which is neither derived from phosphatic acid nor from peptides (WO 9946237, 9946267, 0117516, Iversen, L. F. et al., *J. Med. Chem.* 2002, 45 (20), 4443; *J. Biol. Chem.* 2000, 275, 10300; Moller, N. P. H. et al., *J. Biol. Chem.* 2000, 275, 7101). According to their research, they emphasized that the synthetic PTP1B inhibitor has high selectivity for other protein tyrosine phosphatases.

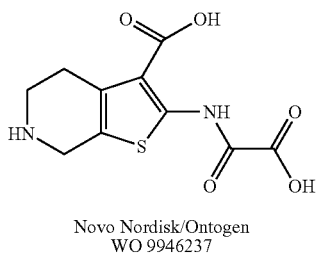

Novo Nordisk/Ontogen
WO 9946237

Continuing to study PTP1B inhibitors, Merck Frosst Canada suggested α,α-difluoromethylenephosphonates structures (WO 0146206, 0146205, 0146204, 0146203, 0069889, 0017211, 0006712, Taylor, S. D. et al., *Bioorg. & Med. Chem. Lett.* 1998, 8, 345; Taylor, S. D. et al., *Bioorg. Med. Chem.* 1998, 6, 1457).

There are a lot of related articles published on the subject of PTP1B inhibitors (Lilijebris et al., *Bioorg. & Med. Chem. Lett.*, 2002, 10, 1; Park et. al. *Biochemistry* 2002, 41, 9043; Cristopher et al., *J. Med. Chem.* 2002, 45 (18), 3946; Choi et al., *Bioorg. & Med. Chem. Lett.*, 2002, 12 (15), 1941; Bleasdale, J. E. et al., *Biochemisty* 2001, 40, 5642; Umezawa, K. et al. *Tetrahedron* 2000, 56, 741; Taylor, S. C. et al., *J. Chem. Soc. Perkin Trans* 72000, 1271; Yokomatsu, T. et al., *Bioorg. & Med. Chem. Lett.* 1999, 9, 529).

Although there are such a large quantity of results as mentioned above, no materials have passed the complete clinical testing thus far. So there is an urgent need to find novel compounds which can be used in humans.

2. CD45

For cells to grow normally, highly elaborate signals are required. When the balance between them is broken and activation signals remain alone, cells grow uncontrollably, thus resulting in the occurrence of disorders. CD45 plays an essential role in terminating the signal transduction responsible for the uncontrollable growth of cells. CD45, a transmembrane PTPase (Protein Tyrosine Phosphatase), was known as an important role in signal transduction in T-cell or B-cells. In CD45 knock-out mice, Janus kinase (JAK) and STAT (signal transducer and activators of transcription) are observed to be activated by cytokines and interferon, demonstrating that CD45 interrupts the signal transduction of cytokines by inhibiting JAK.

In addition, CD45 negatively regulates interleukin-3-mediated cellular proliferation, erythropoietin-dependent hematopoiesis and antiviral responses. This indicates that CD45 suppresses the activity of the immune system of attacking foreign invaders, leading to the suppression of cancer cell proliferation and autoimmune diseases. Based on this finding, CD45 inhibitors can be available to prevent transplant rejection. In fact, extensive research into CN45 inhibitors has been conducted and the results thereof are disclosed in many patents and articles, issued to AstraZeneca Company (WO 0146125, 0145681, 0145680, R. A. Urbanek et al., *J. Med. Chem.* 2001, 44, 1777 and to others (JP2001114678, JP2001114689, WO 0128991, 0119830, 0119831, 0116097, 0128991). However, in spite of the extensive research results, no materials have succeeded in passing clinical testing, and thus there is an urgent need for a novel material for CD45 inhibitors.

3. LAR

It was hypothesized that LAR might be involved in the physiological modulation of insulin receptor signaling in intact cells (Hashimoto et al., *J. Biol. Chem.* 1992, 267, 13811). This conclusion was reached from data obtained by comparing the rate of dephosphorylation/inactivation of purified IR using PTP1B as well as the cytoplasmic domains of LAR. To examine whether the transmembrane PTPase LAR can modulate insulin receptor signaling in vivo, antisense inhibition was recently employed (Kulas et al., *J. Biol. Chem.* 1995, 270, 2435). In this test, LAR protein levels were specifically suppressed by approximately 60% in a rat hepatoma cell line. This suppression of the LAR protein level was paralleled by an approximately 150% increase in the insulin-dependent autophosphorylation of the insulin receptor.

However, only a modest 35% increase in insulin receptor tyrosine kinase (IRTK) activity was observed, whereas reduced LAR levels resulted in a 350% increase in insulin-dependent phosphatidylinositol 3-kinase (PI 3-kinase) activity. The authors speculated that LAR could specifically dephosphorylate tyrosine residues, which are critical for PI 3-kinase activation, either on the insulin receptor itself or on a downstream substrate.

Therefore, LAR inhibitors are expected to be useful in the treatment of obesity, impaired glucose tolerance, diabetes mellitus, hypertension, and partially ischemic diseases. In spite of the results from extensive research and studies, there are no compounds that have passed clinical tests thus far. Therefore, there is a need for a novel material applicable to human bodies for the treatment of such diseases.

4. Cdc25B

A dual specific phosphatase (defined as a subclass within the PTPase family able to hydrolyze phosphate from phosphor-tyrosine as well as from phosphor-serine/threonine) is responsible for the activation of cyclin dependent kinase (CDK) by hydrolyzing inhibitory phosphate from tyrosine and threonine residues of CDK, which is implicated in the cell division cycle. A high level of CDK induces the activation of the MPF (M phase promoting factor) to increase the mitotic activity in the M phase of cell cycle, resulting in cell proliferation.

Accordingly, dual specific phosphatase inhibitors interfere with cell division to thus prevent cell proliferation. Cdc25, a kind of dual specific phosphatase, has been reported to have three homologues, Cdc25A, Cdc25B, and Cdc25C, in human cells. Among them, Cdc25B is inferred to play an important role in carcinogenesis because it is the most highly expressed in cancer cells. Because inducing M phase arrest, therefore, Cdc25B inhibitors can be targets for developing anticancer agents. Extensive and intensive research has been studied on the inhibitors and the results have been reported (Otani, T. et al., *J. of Antibiotics* 2000, 53, 337; Lazo, J. S. et al., *Bioorg. Med. Chem. Lett.* 2000, 8, 1451).

5. VHR

VHR, a dual specific phosphatase, extracellularly regulates extracellular signal receptor kinase 1 (ERK1) and ERK2, both belonging to a subclass of mitogen-activated protein kinase (MAPK), to mediate mitogenic signaling. Since VHR is involved in controlling cell cycles, its inhibitors, like Cdc25B inhibitors, can be available as anticancer agents (Osada, H. et al., *FEBS Letters* 1995, 372, 54).

6. Prl-3

Genetic level changes occurred in colon cancer thus far was the inactivation of tumor suppressors. However, these low-molecular weight materials are not suitable as targets for a novel anticancer drug. A recent report (Sana et al., *Science* 2001, 294, 1343) says that the novel phosphatase Prl-3 is commonly overexpressed in the metastasis of various colon cancer cells. The activity of Prl-3 is essential in the metastasis of colon cancer, therefore, effective Prl-3 inhibitors may be a drug target which can provide a new turning point for the therapy of colon cancer in the metastasis phase.

As elucidated above, overexpression or activity alteration of various protein phosphatases are reported to cause various diseases. Therefore, compounds having inhibitory activity against the protein phosphatases, if developed, could be useful in the prevention and treatment of specific diseases, such as diabetes, autoimmune diseases, and various cancers. Leading to the present invention, intensive and thorough research into protein phosphatase inhibitors, conducted by the present inventors, resulted in the finding that compounds derived from rhodanine can inhibit the activity of protein phosphatases.

DISCLOSURE

Technical Problem

An object of the present invention is to provide a rhodanine derivative or a pharmaceutically acceptable salt thereof.

Another object of the present invention is to provide a method for preparing the rhodanine derivative.

A further object of the present invention is to provide a pharmaceutical composition, comprising the rhodanine derivative or a pharmaceutically acceptable salt thereof as an active ingredient, for the prevention and treatment of various diseases including autoimmune diseases, diabetes, impaired glucose intolerance, insulin resistance, obesity, cancers, etc.

Technical Solution

To accomplish the object, the present invention provide a rhodanine derivative or a pharmaceutically acceptable salt thereof.

The present invention also provide a method for preparing the rhodanine derivative.

The present invention further provide a pharmaceutical composition, comprising the rhodanine derivative or a pharmaceutically acceptable salt thereof as an active ingredient, for the prevention and treatment of various diseases including autoimmune diseases, diabetes, impaired glucose intolerance, insulin resistance, obesity, cancers, etc.

BEST MODE

The present invention provides a rhodanine derivative represented by 1 or a pharmaceutically acceptable salt thereof

[Chemistry Figure 1]

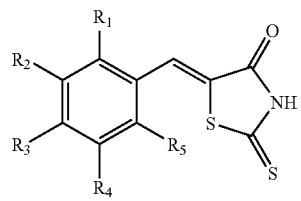

wherein, $R_1$ may be selected from the group consisting of alkoxy, aryl alkoxy, substituted aryl alkoxy, heteroaryl alkoxy, substituted heteroaryl alkoxy, heteroaryl alkyl alkoxy, aryl oxy alkoxy, substituted aryl oxy alkoxy, heteroaryl oxy alkoxy, substituted heteroaryl oxy alkoxy, heterocyclic alkoxy, amino alkoxy, substituted amino alkoxy, heterocyclic oxy alkoxy, cyclic amino alkoxy, heterocyclic amino alkoxy, alkenyl alkoxy, cyclic amino, heterocyclic amino, substituted heterocyclic amino, nitro, sulfonyl, benzenesulfonyl, and substituted benzenesulfonyl, and preferably one selected from the following Compound Group 1;

<Compound Group 1>

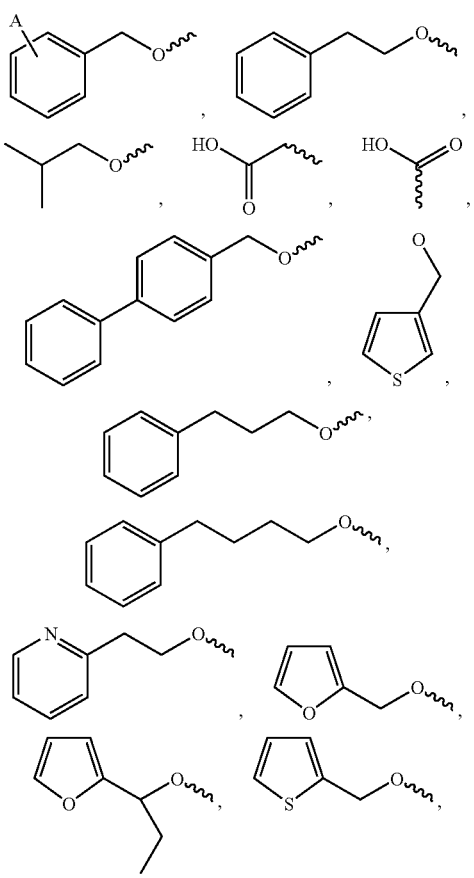

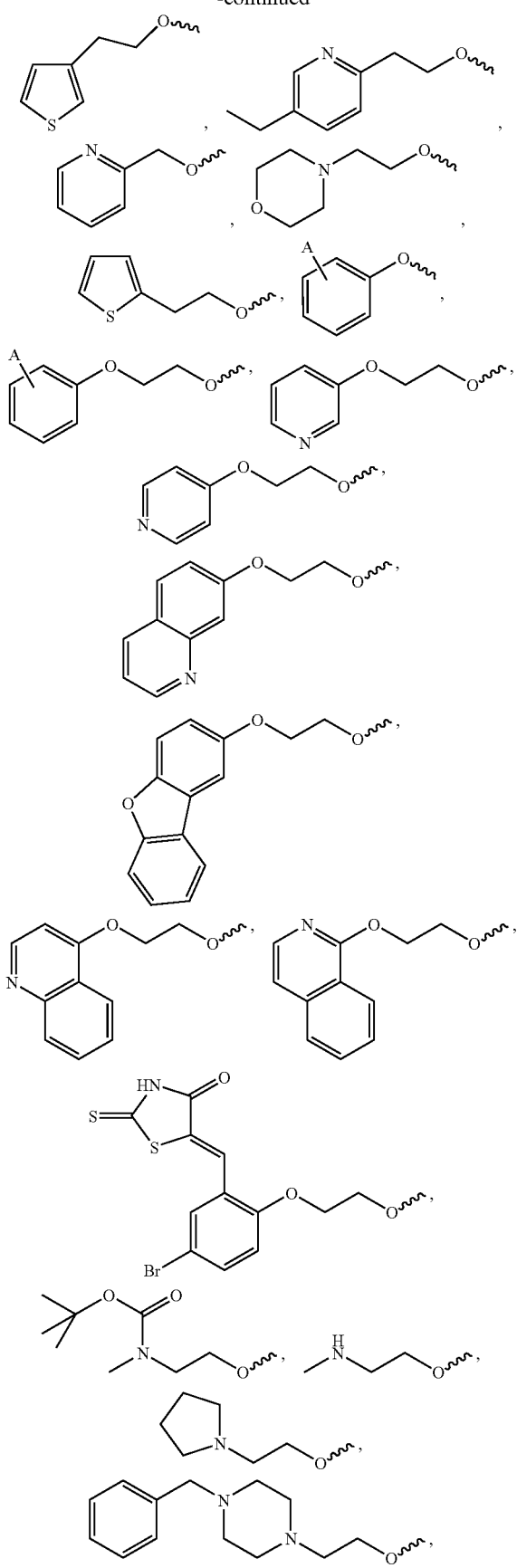
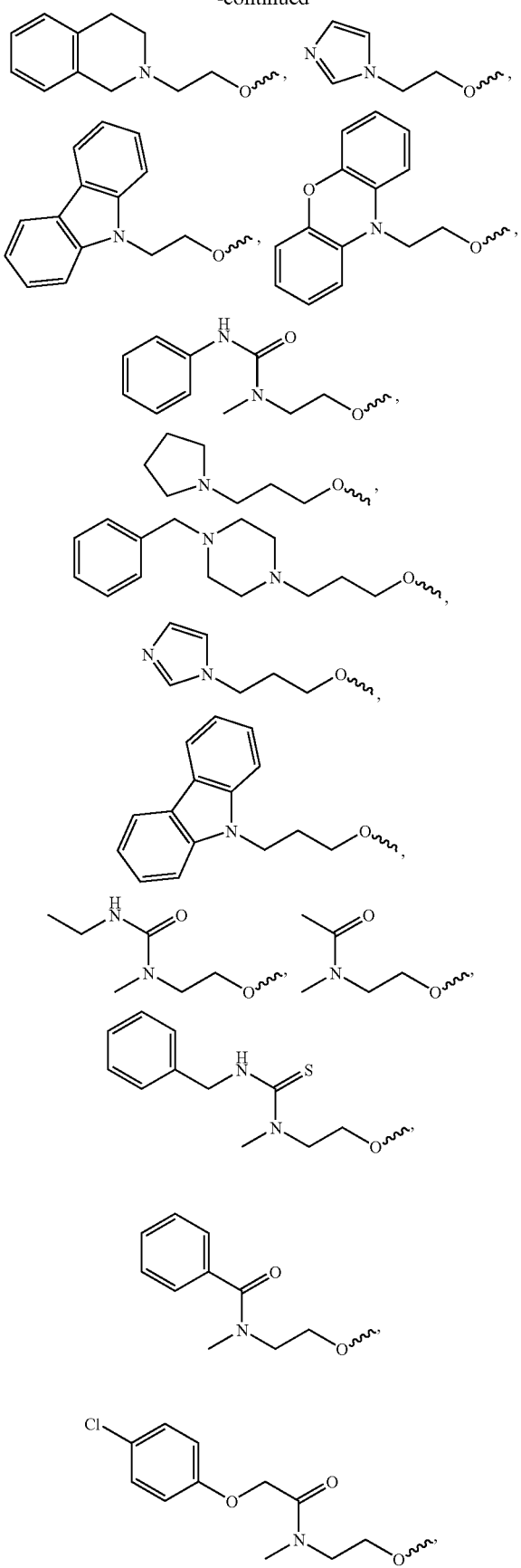

-continued (wherein A is H, one or two halogen atoms, $C_1$~$C_4$ alkyl, trifluoromethyl, cyano, or $C_1$~$C_4$ alkoxy)

$R_2$ is hydrogen, Br, or $R_3$ may be selected from the group consisting of hydrogen, halo, hydroxy, alkoxy, substituted alkoxy, substituted aryl oxy, alkyl amino alkoxy, cyclic amino alkoxy, heterocyclic amino alkoxy, substituted heterocyclic amino alkoxy, alkyl amino aryl, alkyl amido alkoxy, aryl amido alkoxy, sulfonyl amino alkoxy, and substituted aryl oxy amido alkoxy, and preferably one selected from the following Compound Group 2;

<Compound Group>

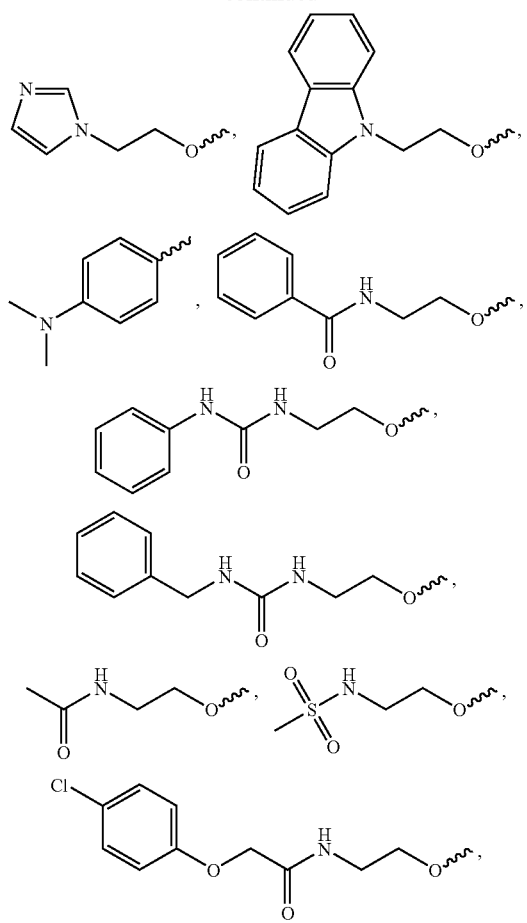

R₄ may be selected from the group consisting of hydrogen, halo, nitro, heterocyclo, alkoxy, aryl alkoxy, and substituted aryl alkoxy, and preferably one selected from the following Compound Group 3;

<Compound Group 2>

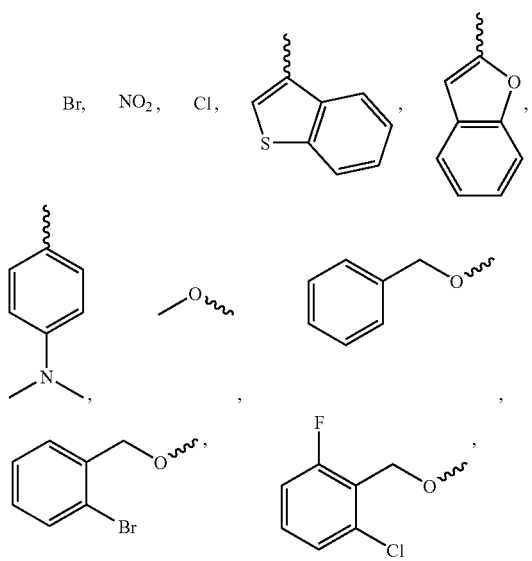

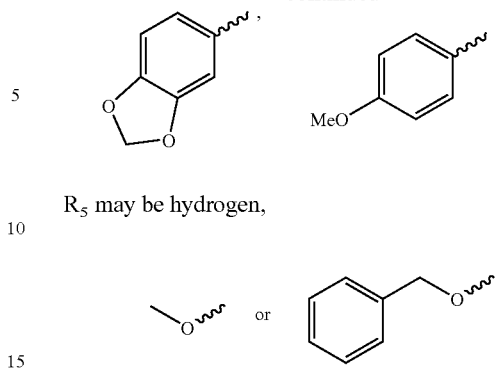

R₅ may be hydrogen,

DETAILED DESCRIPTION OF THE INVENTION

Hereinafter, the present invention will be described more specifically. The rhodanine derivatives according to the present invention include;

1) 5-(2-benzyloxy-5-bromobenzylidene)-2-thioxo-thiazolidin-4-one,
2) 5-(3-benzyloxy-naphthalen-2-ylmethylene)-2-thioxo-thiazolidin-4-one,
3) 5-(2-benzyloxy-naphthalen-1-ylmethylene)-2-thioxo-thiazolidin-4-one,
4) 5-(5-bromo-2-phenethyloxy-benzylidene)-2-thioxo-thiazolidin-4-one,
5) 5-(5-bromo-2-isobutoxy-benzylidene)-2-thioxo-thiazolidin-4-one,
6) 5-(3-benzyloxy-7-bromo-naphthalen-2-ylmethylene)-2-thioxo-thiazolidin-4-one,
7) 5-(2,4-bis-benzyloxy-benzylidene)-2-thioxo-thiazolidin-4-one,
8) 5-(2-benzyloxy-5-nitro-benzylidene)-2-thioxo-thiazolidin-4-one,
9) 5-(2-benzyloxy-3-bromo-5-chloro-benzylidene)-2-thioxo-thiazolidin-4-one,
10) 5-(2-benzyloxy-6-methoxy-benzylidene)-2-thioxo-thiazolidin-4-one,
11) 2-thioxo-5-(2,4,6-tris-benzyloxy-benzylidene)-thiazolidin-4-one,
12) 5-[5-bromo-2-(4-chloro-2-nitro-benzyloxy)-benzylidene]-2-thioxo-thiazolidin-4-one,
13) 5-[5-bromo-2-(2-chloro-6-fluoro-benzyloxy)-benzylidene]-2-thioxo-thiazolidin-4-one,
14) 5-[5-bromo-2-(2-chloro-benzyloxy)-benzylidene]-2-thioxo-thiazolidin-4-one,
15) 5-[5-bromo-2-(2,4-dichloro-benzyloxy)-benzylidene]-2-thioxo-thiazolidin-4-one,
16) 5-[5-bromo-2-(3,4-dichloro-benzyloxy)-benzylidene]-2-thioxo-thiazolidin-4-one,
17) 5-[5-bromo-2-(2,5-dimethyl-benzyloxy)-benzylidene]-2-thioxo-thiazolidin-4-one,
18) 5-[2-(biphenyl-ylmethoxy)-5-bromo-benzylidene]-2-thioxo-thiazolidin-4-one,
19) 5-[5-bromo-2-(3-trifluoromethyl-benzyloxy)-benzylidene]-2-thioxo-thiazolidin-4-one,
20) 5-[5-bromo-2-(3,5-dimethoxy-benzyloxy)-benzylidene]-2-thioxo-thiazolidin-4-one,
21) 5-[5-bromo-2-(2,6-difluoro-benzyloxy)-benzylidene]-2-thioxo-thiazolidin-4-one,
22) 5-[5-bromo-2-(4-bromo-benzyloxy)-benzylidene]-2-thioxo-thiazolidin-4-one, 23) 5-[5-bromo-2-(3-bromo-benzyloxy)-benzylidene]-2-thioxo-thiazolidin-4-one,
24) 5-[5-bromo-2-(2-bromo-benzyloxy)-benzylidene]-2-thioxo-thiazolidin-4-one,
25) 5-[5-bromo-2-(2-nitro-benzyloxy)-benzylidene]-2-thioxo-thiazolidin-4-one,
26) 5-[5-bromo-2-(3-phenyl-propoxy)-benzylidene]-2-thioxo-thiazolidin-4-one,
27) 5-[5-bromo-2-(5-phenyl-pentyloxy)-benzylidene]-2-thioxo-thiazolidin-4-one,
28) 5-(2-benzyloxy-benzylidene)-2-thioxo-thiazolidin-4-one,
29) 5-[3-(2-chloro-6-fluoro-benzyloxy)-naphthalen-2-naphthalen-2-thioxo-thiazolidin-4-one,
30) 5-[3-(3,5-dimethoxy-benzyloxy)-naphthalen-2-ylmethylene]-2-thioxo-thiazolidin-4-one,
31) 5-[3-(biphenyl-4-ylmethoxy)-naphthalen-2-ylmethylene]-2-thioxo-thiazolidin-4-one,
32) 5-(2-benzyloxy-4-diethylamino-benzylidene)-2-thioxo-thiazolidin-4-one,
33) 5-[2-(biphenyl-4-ylmethoxy)-4-diethylamino-benzylidene]-2-thioxo-thiazolidin-4-one,
34) 5-[2-(2-chloro-6-fluoro-benzyloxy)-4-diethylamino-benzylidene]-2-thioxo-thiazolidin-4-one,
35) 5-[4-diethylamino-2-(3,5-dimethoxy-benzyloxy)-benzylidene]-2-thioxo-thiazolidin-4-one,
36) 5-(4-diethylamino-2-phenethyloxy-benzylidene)-2-thioxo-thiazolidin-4-one,
37) 5-[2-(2-chloro-6-fluoro-benzyloxy)-naphthalen-1-ylmethylene]-2-thioxo-thiazolidin-4-one,
38) 5-[2-(3,5-dimethoxy-benzyloxy)-naphthalen-1-ylmethylene]-2-thioxo-thiazolidin-4-one,
39) 5-[5-bromo-2-(2-fluoro-benzyloxy)-benzylidene]-2-thioxo-thiazolidin-4-one,
40) 5-[5-bromo-2-(2-iodo-benzyloxy-benzylidene]-2-thioxo-thiazolidin-4-one, 41) 5-[2-(2-bromo-benzyloxy)-naphthalen-1-ylmethylene]-2-thioxo-thiazolidin-4-one,
42) 5-(2-phenethyloxy-naphthalen-1-ylmethylene)-2-thioxo-thiazolidin-4-one,
43) 5-(5-chloro-2-nitro-benzylidene)-2-thioxo-thiazolidin-4-one,
44) 5-[2,4-bis-(2-bromo-benzyloxy)-benzylidene]-2-thioxo-thiazolidin-4-one,
45) 5-[2,3-bis-(2-chloro-6-fluoro-benzyloxy)-benzylidene]-2-thioxo-thiazolidin-4-one,
46) 5-(2,3-bis-benzyloxy-benzylidene)-2-thioxo-thiazolidin-4-one,
47) 5-(2-benzyloxy-5-methoxy-benzylidene)-2-thioxo-thiazolidin-4-one,
48) 5-[2-(2-bromo-benzyloxy)-4-hydroxy-benzylidene]-2-thioxo-thiazolidin-4-one,
49) 5-(2,5-bis-benzyloxy-benzylidene)-2-thioxo-thiazolidin-4-one,
50) 5-[2,5-bis-(2-bromo-benzyloxy)-benzylidene]-2-thioxo-thiazolidin-4-one,
51) 5-[2,5-bis-(2-chloro-6-fluoro-benzyloxy)-benzylidene]-2-thioxo-thiazolidin-4-one,
52) 5-5-bromo-2-[2-(5-bromo-2-(4-oxo-2-thioxo-thiazolidin-5-ylidenemethyl)-phenoxy)-ethoxy]-benzylidene-2-thioxo-thiazolidin-4-one,
53) 5-[5-bromo-2-(1-phenyl-ethoxy)-benzylidene]-2-thioxo-thiazolidin-4-one,
54) 5-[5-bromo-2-(3-methyl-but-2-enyloxy)-benzylidene]-2-thioxo-thiazolidin-4-one,
55) 5-[5-bromo-2-(1,1-dimethyl-2-oxo-2-methyll-ethoxy)-benzylidene]-2-thioxo-thiazolidin-4-one,
56) 5-(2-benzhydryloxy-5-bromo-benzylidene)-2-thioxo-thiazolidin-4-one,
57) 5-[5-bromo-2-(2-pyridin-2-yl-ethoxy)-benzylidene]-2-thioxo-thiazolidin-4-one,
58) 5-[5-bromo-2-(furan-2-ylmethoxy)-benzylidene]-2-thioxo-thiazolidin-4-one,
59) 5-[5-bromo-2-(thiopen-2-ylmethoxy)-benzylidene]-2-thioxo-thiazolidin-4-one,
60) 5-[5-bromo-2-(thiophen-3-ylmethoxy)-benzylidene]-2-thioxo-thiazolidin-4-one,
61) 5-[5-bromo-2-(2-thiophen-3-yl-ethoxy)-benzylidene]-2-thioxo-thiazolidin-4-one,
62) 5-5-bromo-2-[2-(5-ethyl-pyridin-2-yl)-ethoxy]-benzylidene-2-thioxo-thiazolidin-4-one,
63) 5-[5-bromo-2-(pyridin-2-ylmethoxy)-benzylidene]-2-thioxo-thiazolidin-4-one,
64) 5-[5-bromo-2-(2-morpholin-4-yl-ethoxy)-benzylidene]-2-thioxo-thiazolidin-4-one,
65) 5-[5-bromo-2-(2-thiopen-2-yl-ethoxy)-benzylidene]-2-thioxo-thiazolidin-4-one,
66) 5-[5-bromo-2-(1-furan-2-yl-propoxy)-benzylidene]-2-thioxo-thiazolidin-4-one,
67) toluene-4-sulfonic acid 4-bromo-2-(4-oxo-2-thioxo-thiazolidin-5-ylidenemethyl)-phenyl ester,
68) methanesulfonic acid 4-bromo-2-(4-oxo-2-thioxo-thiazolidin-5-ylidenemethyl)-phenyl ester,
69) 2,4,6-trimethyl-benzenesulfonic acid 4-bromo-2-(4-oxo-2-thioxo-thiazolidin-5-ylidenemethyl)-phenyl ester,
70) 4-bromo-benzenesulfonic acid 4-bromo-2-(4-oxo-2-thioxo-thiazolidin-5-ylidenemethyl)-phenyl ester,
71) 5-(5-bromo-2-phenoxy-benzylidene)-2-thioxo-thiazolidin-4-one,
72) 5-(4-bromo-2-phenoxy-benzylidene)-2-thioxo-thiazolidin-4-one,
73) 5-(2-morpholin-4-yl-benzylidene)-2-thioxo-thiazolidin-4-one,
74) 5-[2-(4-methyl-piperazin-1-yl)-benzylidene]-2-thioxo-thiazolidin-4-one,
75) 5-[2-(4-benzyl-piperazin-1-yl)-benzylidene]-2-thioxo-thiazolidin-4-one,
76) 5-(5-bromo-2-morpholin-4-yl-benzylidene)-2-thioxo-thiazolidin-4-one,
77) 5-[5-bromo-2-(2-bromo-phenoxy)-benzylidene]-2-thioxo-thiazolidin-4-one,
78) 5-[5-bromo-2-(3-bromo-phenoxy)-benzylidene]-2-thioxo-thiazolidin-4-one,
79) 5-[5-bromo-2-(4-bromo-phenoxy)-benzylidene]-2-thioxo-thiazolidin-4-one,
80) 2-[4-bromo-2-(4-oxo-2-thioxo-thiazolidin-5-ylidenemethyl)-phenoxy]-benzonitrile,
81) 5-[5-bromo-2-(2,4-dibromo-phenoxy)-benzylidene]-2-thioxo-thiazolidin-4-one,
82) 5-[2-(4-benzyl-piperazin-1-yl)-5-bromo-benzylidene]-2-thioxo-thiazolidin-4-one,
83) 5-(5-bromo-2-piperidin-1-yl-benzylidene)-2-thioxo-thiazolidin-4-one,
84) 5-(5-bromo-2-pyrrolidin-1-yl-benzylidene)-2-thioxo-thiazolidin-4-one,
85) 5-[4-bromo-2-(2-bromo-phenoxy)-benzylidene]-2-thioxo-thiazolidin-4-one,
86) 5-[4-bromo-2-(3-bromo-phenoxy)-benzylidene]-2-thioxo-thiazolidin-4-one,
87) 5-[2,4-bis-(4-bromo-phenoxy)-benzylidene]-2-thioxo-thiazolidin-4-one,
88) 5-[5-bromo-2-(4-methyl-piperazin-1-yl)-benzylidene]-2-thioxo-thiazolidin-4-one, 89) 2-[5-bromo-2-(4-oxo-2-thioxo-thiazolidin-5-ylidenemethyl)-phenoxy]-benzonitrile,
90) 5-(4-benzyloxy-biphenyl-3-ylmethylene)-2-thioxo-thiazolidin-4-one,
91) 5-(5-benzo[b]thiophen-3-yl-2-benzyloxy-benzylidene)-2-thioxo-thiazolidin-4-one,
92) 5-(5-benzofuran-2-yl-2-benzyloxy-benzylidene)-2-thioxo-thiazolidin-4-one,
93) 5-(4-benzyloxy-4'-dimethylamino-biphenyl-3-ylmethylene)-2-thioxo-thiazolidin-4-one,
94) 5-[4-(2-chloro-6-fluoro-benzyloxy)-4'-dimethylamino-biphenyl-3-ylmethylene]-2-thioxo-thiazolidin-4-one,
95) 5-[4-(2-bromo-benzyloxy)-4'-dimethylamino-biphenyl-3-ylmethylene]-2-thioxo-thiazolidin-4-one,
96) 5-[4'-dimethylamino-4-(4-methoxy-benzyloxy)-biphenyl-3-ylmethylene]-2-thioxo-thiazolidin-4-one,
97) 5-(4'-dimethylamino-3-phenoxy-biphenyl-4-ylmethylene)-2-thioxo-thiazolidin-4-one,
98) 5-(4-benzyloxy-4'-methoxyethoxy-3-ylmethylene)-2-thioxo-thiazolidin-4-one,
99) 5-[4'-dimethylamino-4-(1-phenyl-ethoxy)-biphenyl-3-ylmethylene]-2-thioxo-thiazolidin-4-one,
100) 5-[5-benzo[1,3]dioxo-5-yl-2-(1-phenyl-ethoxy)-benzylidene]-2-thioxo-thiazolidin-4-one,
101) 5-(4-benzyloxy-4'-dimethylamino-biphenyl-3-ylmethylene)-2-thioxo-thiazolidin-4-one,
102) 5-(5-benzo[1,3]dioxo-5-yl-2-benzyloxy-benzylidene)-2-thioxo-thiazolidin-4-one,
103) 5-[4'-dimethylamino-4-(3-methyl-but-2-enyloxy)-biphenyl-3-ylmethylene]-2-thioxo-thiazolidin-4-one,
104) 5-[4'-dimethylamino-4-(1,1-dimethyl-2-oxo-2-phenyl-ethoxy)-biphenyl-3-ylmethylene]-2-thioxo-thiazolidin-4-one,
105) 5-[5-benzo[1,3]-dioxo-5-yl-2-(1,1-dimethyl-2-oxo-2-phenyl-ethoxy)-benzylidene]-2-thioxo-thiazolidin-4-one,
106) 5-(4-benzhydryloxy-4'-dimethylamino-biphenyl-3-ylmethylene)-2-thioxo-thiazolidin-4-one,
107) 5-(2-benzhydryloxy-5-benzo[1,3]dioxo-5-yl-benzylidene)-2-thioxo-thiazolidin-4-one,
108) 5-2-[2-(benzothiazol-2-yloxy)-ethoxy]-5-bromo-benzylidene-2-thioxo-thiazolidin-4-one,
109) 5-5-bromo-2-[2-(isoquinolin-5-yloxy)-ethoxy]-benzylidene-2-thioxo-thiazolidin-4-one,
110) 5-5-bromo-2-[2-(isoquinolin-7-yloxy)-ethoxy]-benzylidene-2-thioxo-thiazolidin-4-one,
111) 5-5-bromo-2-[2-(6-methyl-pyridin-3-yloxy)-ethoxy]-benzylidene-2-thioxo-thiazolidin-4-one,
112) 5-5-bromo-2-[2-(1-oxy-pyridin-3-yloxy)-ethoxy]-benzylidene-2-thioxo-thiazolidin-4-one,
113) 5-5-bromo-2-[2-(2-bromo-phenoxy)-ethoxy]-benzylidene-2-thioxo-thiazolidin-4-one,
114) 5-5-bromo-2-[2-(3-bromo-phenoxy)-ethoxy]-benzylidene-2-thioxo-thiazolidin-4-one,
115) 5-5-bromo-2-[2-(4-bromo-phenoxy)-ethoxy]-benzylidene-2-thioxo-thiazolidin-4-one,
116) 5-5-bromo-2-[2-(3,5-dibromo-phenoxy)-ethoxy]-benzylidene-2-thioxo-thiazolidin-4-one,
117) 2-2-[4-bromo-2-(4-oxo-2-thioxo-thiazolidin-5-ylidenemethyl)-phenoxy]-ethoxy-benzonitrile,
118) 4-2-[4-bromo-2-(4-oxo-2-thioxo-thiazolidin-5-ylidenemethyl)-phenoxy]-ethoxy-benzonitrile,
119) 5-5-bromo-2-[2-(2-chloro-phenoxy)-ethoxy]-benzylidene-2-thioxo-thiazolidin-4-one,
120) 5-5-bromo-2-[2-(4-chloro-phenoxy)-ethoxy]-benzylidene-2-thioxo-thiazolidin-4-one,
121) 5-5-bromo-2-[2-(3,5-dichloro-phenoxy)-ethoxy]-benzylidene-2-thioxo-thiazolidin-4-one,
122) 5-5-bromo-2-[2-(2-iodo-phenoxy)-ethoxy]-benzylidene-2-thioxo-thiazolidin-4-one,
123) 5-5-bromo-2-[2-(4-iodo-phenoxy)-ethoxy]-benzylidene-2-thioxo-thiazolidin-4-one,
124) 5-5-bromo-2-[2-(3-iodo-phenoxy)-ethoxy]-benzylidene-2-thioxo-thiazolidin-4-one,
125) 5-[5-bromo-2-(2-phenoxy-ethoxy)-benzylidene]-2-thioxo-thiazolidin-4-one,
126) 5-5-bromo-2-[2-(pyridin-3-yloxy)-ethoxy]-benzylidene-2-thioxo-thiazolidin-4-one,
127) 5-5-bromo-2-[2-(pyridin-4-yloxy)-ethoxy]-benzylidene-2-thioxo-thiazolidin-4-one,
128) 5-5-bromo-2-[2-(quinolin-7-yloxy)-ethoxy]-benzylidene-2-thioxo-thiazolidin-4-one,
129) 5-5-bromo-2-[2-(dibenzofuran-2-yloxy)-ethoxy]-benzylidene-2-thioxo-thiazolidin-4-one,
130) 5-5-bromo-2-[2-(4-methoxy-phenoxy)-ethoxy]-benzylidene-2-thioxo-thiazolidin-4-one,
131) 5-5-bromo-2-[2-(4-sec-butyl-phenoxy)-ethoxy]-benzylidene-2-thioxo-thiazolidin-4-one,
132) 5-5-bromo-2-[2-(2,6-dimethyl-phenoxy)-ethoxy]-benzylidene-2-thioxo-thiazolidin-4-one,
133) 5-5-chloro-2-[2-(4-methoxy-phenoxy)-ethoxy]-benzylidene-2-thioxo-thiazolidin-4-one,
134) 5-5-chloro-2-[3-(3,5-dimethyl-phenoxy)-propoxy]-benzylidene-2-thioxo-thiazolidin-4-one,
135) 5-5-bromo-2-[2-(quinolin-4-yloxy)-ethoxy]-benzylidene-2-thioxo-thiazolidin-4-one,
136) 5-5-bromo-2-[2-(isoquinolin-1-yloxy)-ethoxy]-benzylidene-2-thioxo-thiazolidin-4-one,
137) 5-2-[2-(4-benzyl-piperazin-1-yl)-ethoxy]-5-bromo-benzylidene-2-thioxo-thiazolidin-4-one,
138) 5-[5-bromo-2-(2-pyrrolidin-1-yl-ethoxy)-benzylidene]-2-thioxo-thiazolidin-4-one,
139) 5-5-bromo-2-[2-(3,4-dihydro-1H-isoquinolin-2-yl)-ethoxy]-benzylidene-2-thioxo-thiazolidin-4-one,
140) 5-[5-bromo-2-(2-imidazol-1-yl-ethoxy)-benzylidene]-2-thioxo-thiazolidin-4-one,
141) 5-[5-bromo-2-(2-carbazol-9-yl-ethoxy)-benzylidene]-2-thioxo-thiazolidin-4-one,
142) 5-2-[2-(9H-acridin-10-yl)-ethoxy]-5-bromo-benzylidene-2-thioxo-thiazolidin-4-one,
143) 5-2-[3-(4-benzyl-piperazin-1-yl)-propoxy]-5-bromo-benzylidene-2-thioxo-thiazolidin-4-one,
144) 5-[5-bromo-2-(3-pyrrolidin-1-yl-propoxy)-benzylidene]-2-thioxo-thiazolidin-4-one,
145) 5-[5-bromo-2-(3-carbazol-9-yl-propoxy)-benzylidene]-2-thioxo-thiazolidin-4-one,
146≡-[5-bromo-2-(3-imidazol-1-yl-propoxy)-benzylidene]-2-thioxo-thiazolidin-4-one,
147) 5-[2-(2-bromo-benzyloxy)-4-(2-bromo-ethoxy)-benzylidene]-2-thioxo-thiazolidin-4-one,
148) 5-[4-[2-(4-benzyl-piperazin-1-yl)-ethoxy]-2-(2-bromo-benzyloxy)-benzylidene]-2-thioxo-thiazolidin-4-one,
149) 5-[2-(2-bromo-benzyloxy)-4-(2-morpholin-4-yl-ethoxy)-benzylidene]-2-thioxo-thiazolidin-4-one,
150) 5-[2-(2-bromo-benzyloxy)-4-(2-diethylamino-ethoxy)-benzylidine]-2-thioxo-thiazolidin-4-one,
151) 5-[2-(2-bromo-benzyloxy)-4-(2-piperidin-1-yl-ethoxy)-benzylidene]-2-thioxo-thiazolidin-4-one,
152) 5-2-(2-bromo-benzyloxy)-4-[2-(3,4-dihydro-1H-isoquinolin-2-yl)-ethoxy]-benzylidene-2-thioxo-thiazolidin-4-one,
153) 5-[2-(2-bromo-benzyloxy)-4-(2-phenoxazin-10-yl-ethoxy)-benzylidene]-2-thioxo-thiazolidin-4-one,
154) 5-[2-(2-bromo-benzyloxy)-4-(2-idol-1-yl-ethoxy)-benzylidene]-2-thioxo-thiazolidin-4-one, 155) 5-[2-(2-bromo-benzyloxy)-4-(2-imidazol-1-yl-ethoxy)-benzylidene]-2-thioxo-thiazolidin-4-one,
156) 5-[2-(2-bromo-benzyloxy)-4-(2-carbazol-9-yl-ethoxy)-benzylidene]-2-thioxo-thiazolidin-4-one,
157) 2-[4-bromo-2-(4-oxo-2-thioxo-thiazolidin-5-ylidenemethyl)-phenoxy]-ethyl-methyl-carbamic acid t-butyl ester,
158) 5-[5-bromo-2-(2-methylamino-ethoxy)benzylidene]-2-thioxo-thiazolidin-4-one; trifluoro acetic acid compound,
159) 1-2-[4-bromo-2-(4-oxo-2-thioxo-thiazolidin-5-ylidenemethyl)-phenoxy]-ethyl-1-methyl-3-phenyl-urea,
160) 1-2-[4-bromo-2-(4-oxo-2-thioxo-thiazolidin-5-ylidenemethyl)-phenoxy]-ethyl-3-(4-methoxy-phenyl)-1-methyl-urea,
161) 1-2-[4-bromo-2-(4-oxo-2-thioxo-thiazolidin-5-ylidenemethyl)-phenoxy]-ethyl-3-ethyl-1-methyl-urea,
162) N-2-[4-bromo-2-(4-oxo-2-thioxo-thiazolidin-5-ylidenemethyl)-phenoxy]-ethyl-N-methyl-acetamide,
163) 3-benzyl-1-2-[4-bromo-2-(4-oxo-2-thioxo-thiazolidin-5-ylidenemethyl)-phenoxy]-ethyl-1-methyl-thiourea,
164) N-2-[4-bromo-2-(4-oxo-2-thioxo-thiazolidin-5-ylidenemethyl)-phenoxy]-ethyl-N-methyl-benzamide,
165) N-2-[4-bromo-2-(4-oxo-2-thioxo-thiazolidin-5-ylidenemethyl)-phenoxy]-ethyl-2-(4-chloro-phenoxy)-N-methyl-acetamide,
166) N-2-[4-bromo-2-(4-oxo-2-thioxo-thiazolidin-5-ylidenemethyl)-phenoxy]-ethyl-N-methyl-methanesulfoneamide,
167) N-2-[4-bromo-2-(4-oxo-2-thioxo-thiazolidin-5-ylidenemethyl)-phenoxy]-ethyl-4,N-dimethyl-benzenesulfoneamide,
168) N-2-[3-(2-bromo-benzyloxy)-4-(4-oxo-2-thioxo-thiazolidin-5-ylidenemethyl)-phenoxy]-ethyl-2-(4-chlorophenoxy)-acetamide,
169) N-2-[3-(2-bromo-benzyloxy)-4-(4-oxo-2-thioxo-thiazolidin-5-ylidenemethyl)-phenoxy]-ethyl-benzamide,
170) 1-2-[3-(2-bromo-benzyloxy)-4-(4-oxo-2-thioxo-thiazolidin-5-ylidenemethyl)-phenoxy]-ethyl-3-phenyl-urea,
171) 1-benzyl-3-2-[3-(2-bromo-benzyloxy)-4-(4-oxo-2-thioxo-thiazolidin-5-ylidenemethyl)-phenoxy]-ethyl-urea,
172) N-2-[3-(2-bromo-benzyloxy)-4-(4-oxo-2-thioxo-thiazolidin-5-ylidenemethyl)-phenoxy]-ethyl-acetamide,
173) N-2-[3-(2-bromo-benzyloxy)-4-(4-oxo-2-thioxo-thiazolidin-5-ylidenemethyl)-phenoxy]-ethyl-methane sulfoneamide, and
174) 5-[2-(2-bromo-benzyloxy)-4-(2-pyridin-2-yl-ethoxy)-benzylidene]-2-thioxo-thiazolidin-4-one.

It should be noted that isomers of the rhodanine derivatives represented by Chemical Formula 1, whether optical or geometrical, fall within the scope of the present invention. In addition, the rhodanine derivatives according to the present invention may be in free forms or in the form of acid or base addition salts, which are also within the scope of the present invention. Examples of the acid suitable for acid addition salts of the rhodanine derivatives include hydrochloric acid, trifluoroacetic acid, citric acid, lactic acid, maleic acid and fumaric acid. Preferable base addition salts of the rhodanine derivatives may be obtained through the use of sodium, potassium, or amine-based organic salts.

In accordance with an aspect of the present invention, a method is provided for preparing the rhodanine derivatives represented by Chemical Formula 1 or pharmaceutically acceptable salts thereof. The rhodanine derivatives according to the present invention can be synthesized through various routes, which will be described in detail in conjugation with Reaction Formulas 1 to 3, below. In Reaction Formula 1 to 3, each of $R_1$ to $R_5$ is as defined above.

In one embodiment of the present invention, provided is a method for the preparation of a rhodanine derivative, represented by the flowing chemical formula 1 from a compound represented by the following chemical formula 2 through the route of Chemical Reaction 1.

[Chemical Reaction 1]

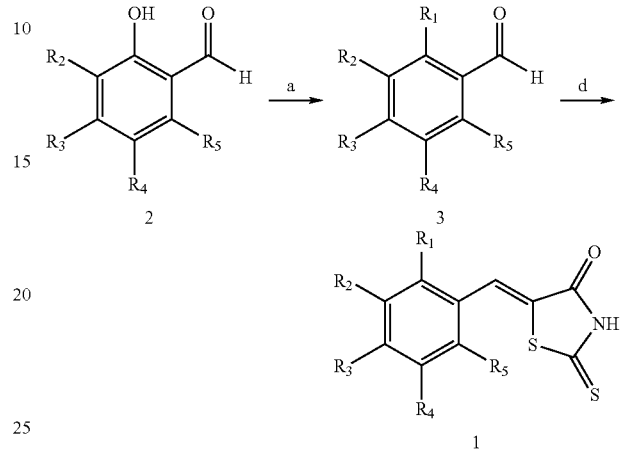

In Reaction Formula 1, (a) is a step to synthesize the intermediate represented by chemical formula 3, which may be converted to the rhodanine derivative according to the present invention. The step (a) can be accomplished though one of the three synthesis routes to be described as follows (Synthesis Routes 1~3).

Synthesis Route 1: Step (a) of preparing an intermediate, represented by chemical formula 3, to the rhodanine derivative can be conducted by reacting the compound of chemical formula 2 with alkyl or aryl bromide having various substituent(s) in the presence of a suitable base under a nitrogen atmosphere with stirring. When the reactant of chemical formula 2 is consumed completely, the reaction terminates, which can be readily detected by thin layer chromatography.

In more detail, potassium carbonate, sodium carbonate or sodium hydride is preferably used as the base in an amount of 2~10 equivalents in association with the catalyst selected from among potassium iodide and sodium iodide.

For this reaction, dimethylform amide or acetone may be used as a solvent. This reaction is preferably conducted at room temperature to 120° C. for 1~36 hour(s). The alkyl or aryl bromide having various substituent(s) may be selected from the following Compound Group 4.

<Compound Group 4>

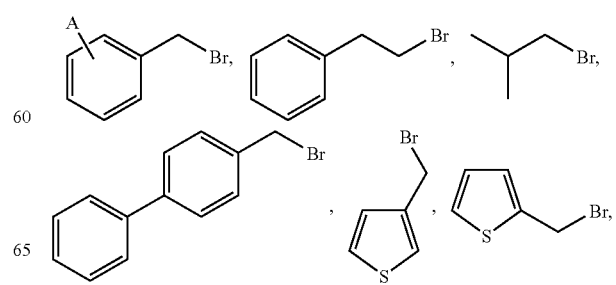

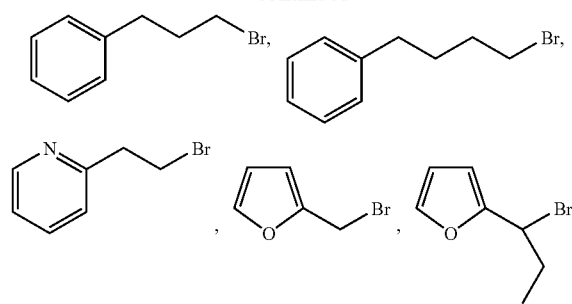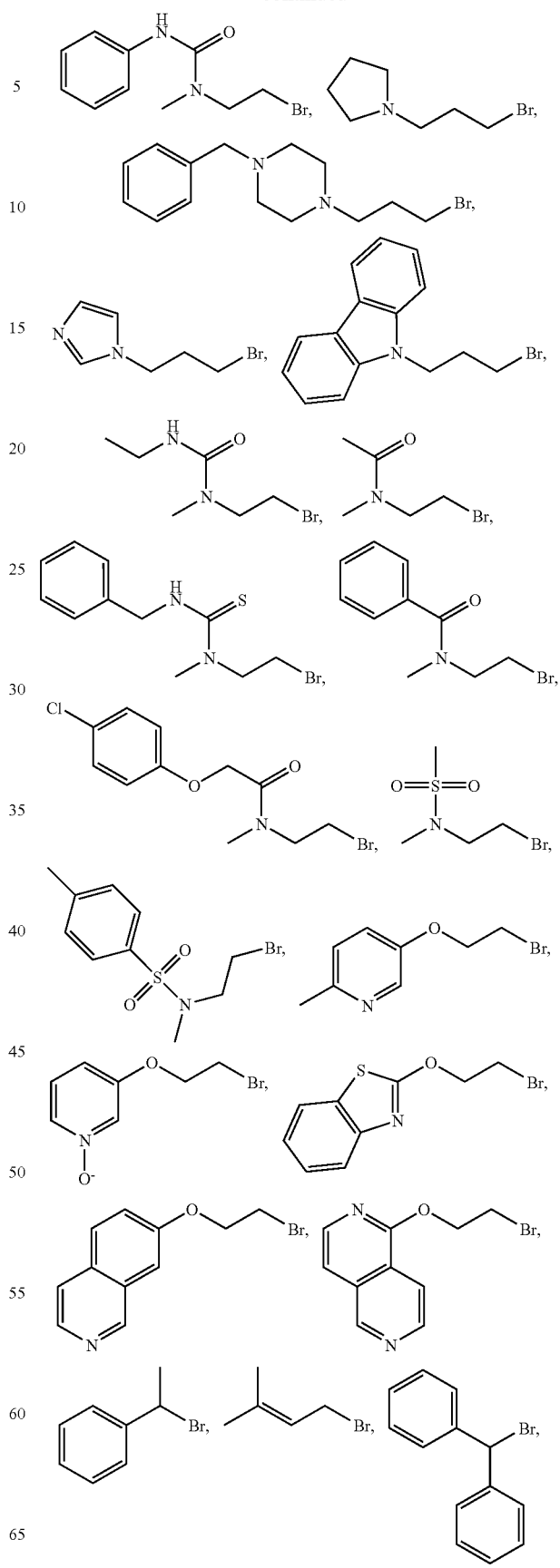

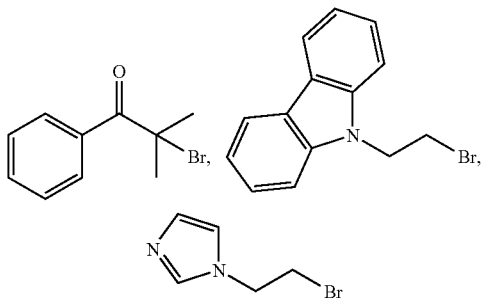

(A is H, one or two halogen atoms, $C_1$~$C_4$ alkyl, trifluoromethyl, cyano, or $C_1$~$C_4$ alkoxy)

Synthesis Route 2: Step (a) of preparing an intermediate, represented by chemical formula 3, to the rhodanine derivative according to the present invention can utilize the Mitsunobu reaction (O. Mitsunobu, *Bull. Chem. Soc. Jpn.* 1967, 40, 4235; O. Mitsunobu, *Synthesis* 1981, 1). In this case, 1~3 equivalents) of an alcohol selected from the following Compound Group 5 is treated with triphenylphosphine, and diethyl azodicarboxylate (DEAD) or diisopropyl azodicarboxylate (DIAD). This Mitsunobu reaction is preferably conducted in a solvent, such as tetrahydroforan, diethylether or benzene, at a temperature from 0 to 30° C. for 1~12 hour(s).

<Compound Group 5>

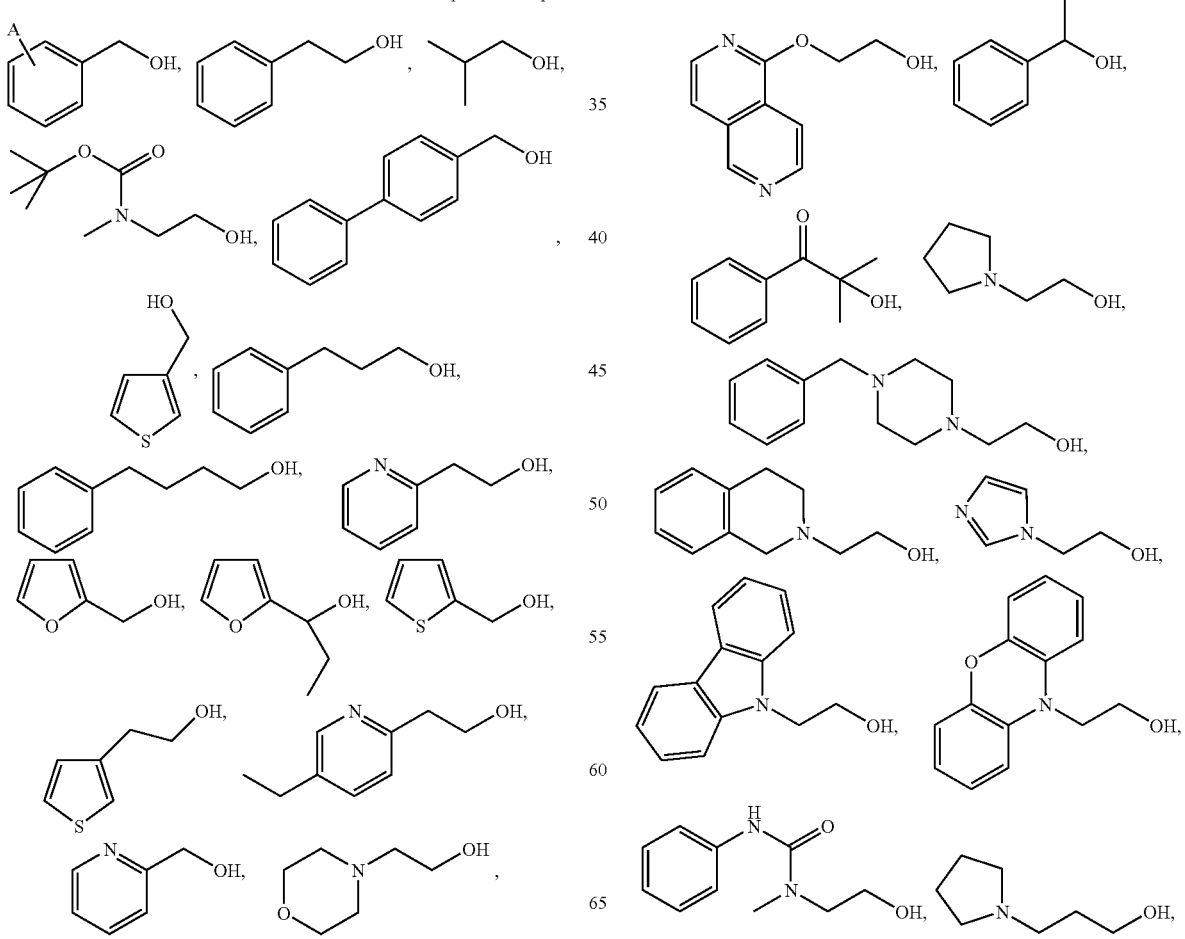

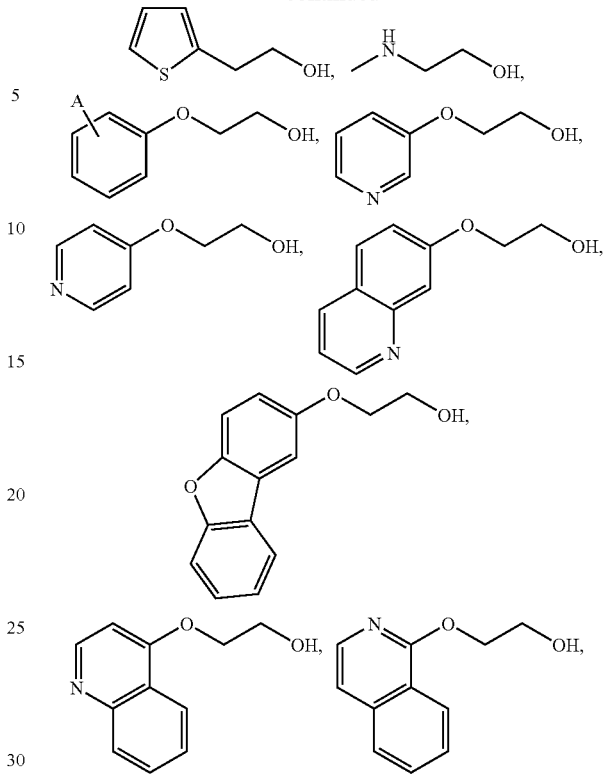

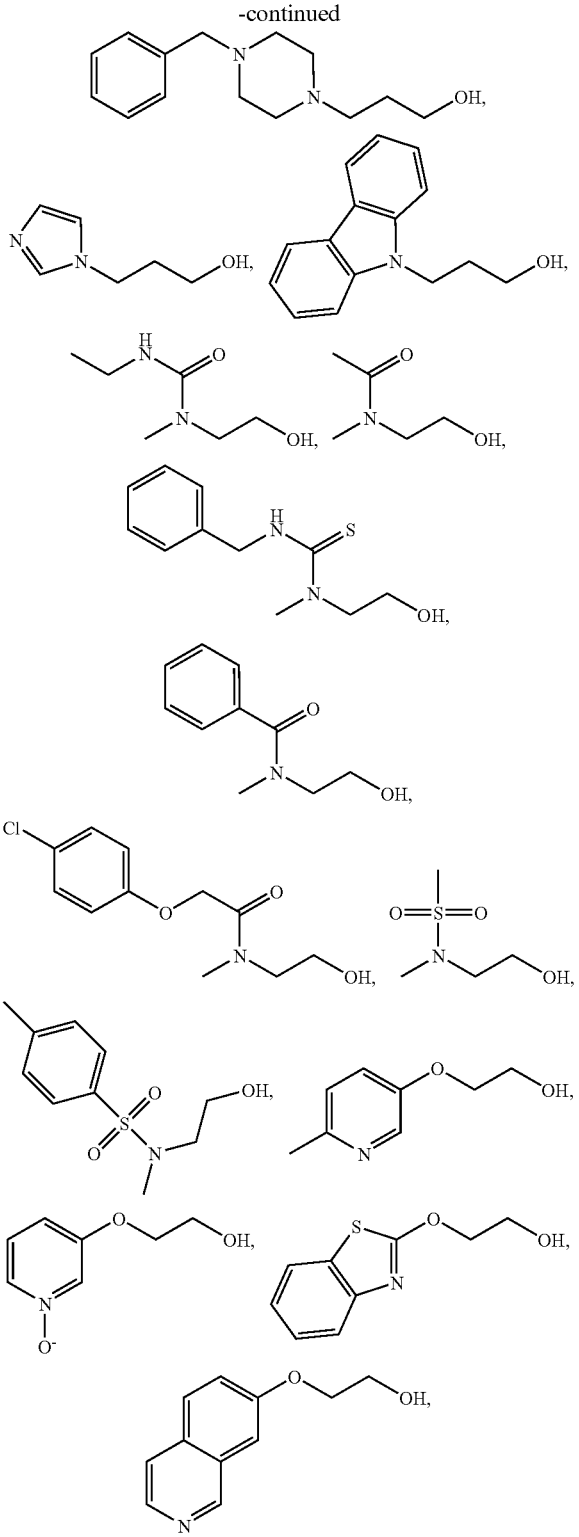

(A is H, one or two halogen atoms, $C_1$~$C_4$ alkyl, trifluoromethyl, cyano, or $C_1$~$C_4$ alkoxy)

Synthesis Route 3: Step (a) of preparing an intermediate, represented by chemical formula 3, to the rhodanine derivative can be conducted by reacting the compound of chemical formula 2 with various sulfonyl chloride(s) selected from the following Compound Group 6.

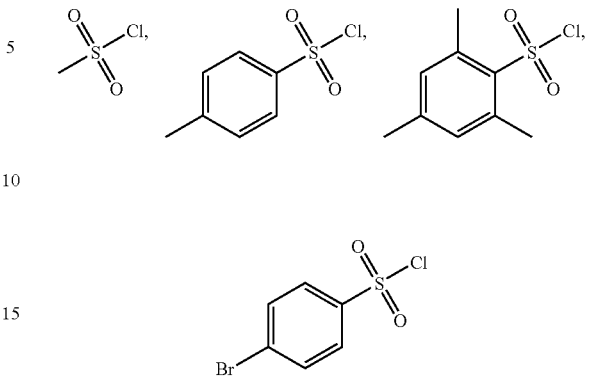

<Compound Group 6>

This reaction is preferably conducted at 0~30° C. for 1~12 hour(s) in the presence of 1~3 equivalents) of a base, such as pyridine or triethylamine, in a solvent, such as chloroform or dichloromethane.

From the compound of chemical formula 3 obtained by way of one of the three synthesis routes of step (a), thereafter, the rhodanine derivative of chemical formula 1 can be prepared through step (d) in Reaction Formula 1.

Step (d) is to react the compound of chemical formula 3 with 2-thioxo-thiazolidin-4-one (rhodanine), represented by the following chemical formula 4, in the presence of ammonium or sodium acetate and acetic acid to afford the rhodanine derivative of chemical formula 1. Preferably, 2~5 equivalents of ammonium acetate or sodium and 5~10 equivalents of acetic acid are used. For this reaction, benzene or toluene is preferably used as a solvent. The reaction is conducted at 5~120° C. for 3~24 hours. The complete consumption of the compound of chemical formula 3 leads to the termination of the reaction, which can be readily monitored by thin layer chromatography.

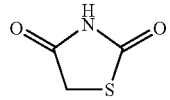

[Chemical Formula 4]

In another embodiment of the present invention, a method is provided for preparing the rhodanine derivative of chemical formula 1 from a compound represented by the following chemical formula 5 through the route of Chemical Reaction 2 (Synthesis Route 4).

[Chemical Reaction 2]

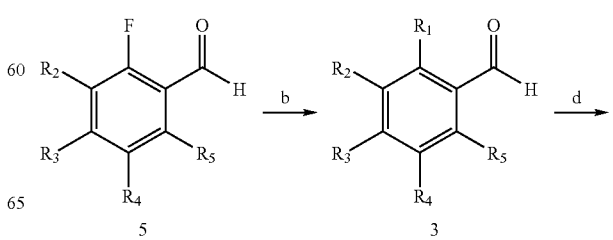

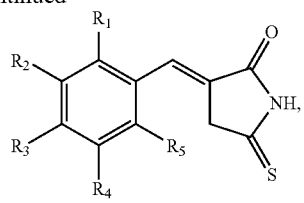

1

In Reaction Formula 2, step (b) is the synthesis of an intermediate, represented by chemical formula 3, to the rhodanine derivative according to the present invention from the compound of chemical formula 5 used as a starting material.

Synthesis Route 4: The compound of chemical formula 5 is commercially available. Starting from the compound of chemical formula 5, the intermediate of chemical formula 3 can be synthesized using a method known in the art (Chen, C. et. al. *J. Med. Chem.* 2004, 47, 6821; Marsh, C. *Eur. J. Org. Chem.* 2003, 14, 2566) in which the starting material is reacted with an amine or a phenol derivative in the presence of an inorganic base. The amine or phenol derivative useful in the present invention is selected from the following Compound Group 7. Potassium carbonate, sodium hydride, or sodium carbonate may be used as a preferable inorganic base.

<Compound Group 7>

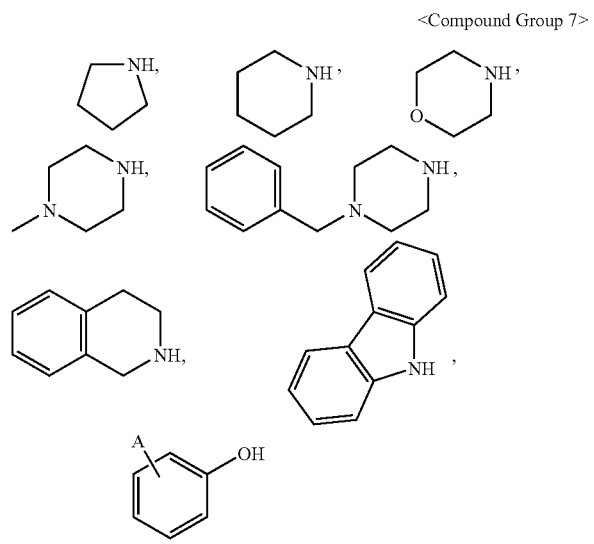

(wherein A is hydrogen, one or two halogen, $C_1$~$C_4$ alkyl, trifluoromethyl, cyano, or $C_1$~$C_4$ alkoxy)

In this reaction, the amine and inorganic base each are preferably used in an amount from 2 to 10 equivalents. Step (b) is preferably conducted at 100~150° C. for 3~24 hours in a polar solvent, such as dimethyl sulfoxide, dimethylformamide, or dimethyl acetamide. The complete consumption of the compound of chemical formula 5 leads to the termination of Step (b), which can be readily monitored by thin layer chromatography.

Subsequently, the preparation of the rhodanine derivative of chemical formula 1 from the compound of chemical formula 3, synthesized through Step (b), can be achieved through the same Step (d) as described above.

In a further embodiment of the present invention, a method is provided for preparing the rhodanine derivative of chemical formula 1 from a compound represented by the following chemical formula 6 through the route of Chemical Reaction 3 (Synthesis Route 5).

[Reaction Formula 3]

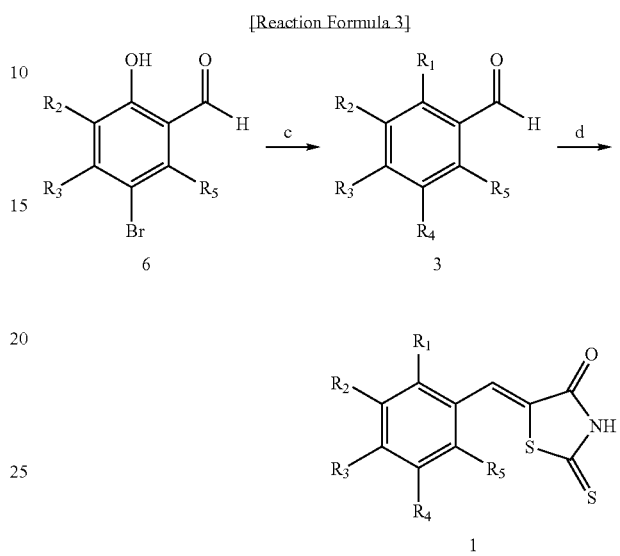

In Reaction Formula 3, Step (c) is the synthesis of an intermediate, represented by chemical formula 3, to the rhodanine derivative according to the present invention, from the compound of chemical formula 6 used as a starting material.

Synthesis Route 5: The compound of chemical formula 6 is commercially available. Step (c) takes advantage of the Suzuki reaction (Ismail, M. et. al. *Bioorg. Med. Chem.* 2004, 12, 5045; Mor, M et. al. *J. Med. Chem.* 2004, 47, 4998) featuring a biaryl coupling between organoboronic acid and halide in the presence of a palladium catalyst, thereby introducing the substituent $R_4$ into the starting material. As for $R_1$, it can be introduced by way of one of Synthesis Routes 1 to 3 described above.

Preferable as a boronic acid suitable for use in Step (c) of the Suzuki reaction is one selected from the following Compound Group 8. This reaction is preferably conducted at a temperature ranging from room temperature to 120° C. in a polar solvent such as tetrahydrofuran, dimethylformamide, ethylene glycoldimethyether, or water. Depending on the amount of the palladium catalyst used, the reaction time preferably falls within a range from 3 to 15 hours. In this case, 0.01~0.3 equivalents of the palladium catalyst are used. The termination of Step (c) is determined by the complete consumption of the compound of chemical formula 5, which can be readily monitored using thin layer chromagraphy.

Compound Group 8

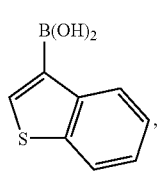

-continued

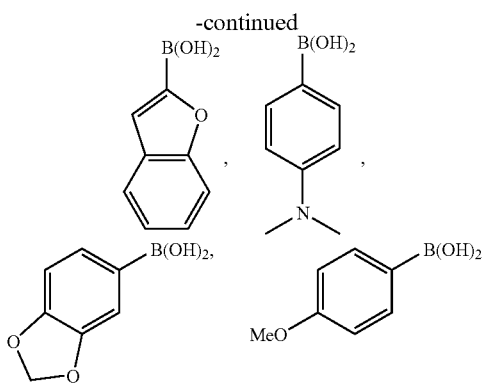

Subsequently, the preparation of the rhodanine derivative of chemical formula 1 from the compound of chemical formula 3, synthesized through Step (c), can be achieved through the same Step (d) as described above.

Pharmaceutically acceptable salts of the rhodanine derivatives according to the present invention may be prepared according to a typical method. For use in the formation of pharmaceutically acceptable salts of the rhodanine derivative, inorganic acids or organic acids may be used. Examples of the inorganic acids useful for the pharmaceutically acceptable salts according to the present invention include hydrochloric acid, bromic acid, sulfuric acid, and phosphoric acid. Suitable organic acids are exemplified by citric acid, acetic acid, lactic acid, tartaric acid, fumaric acid, formic acid, propionic acid, oxalic acid, trifluoroacetic acid, methanesulfonic acid, maleic acid, benzoic acid, gluconic acid, glycolic acid, succinic acid, 4-morpholino ethanesulfonic acid, camphorsulfonic acid, 4-nitrobenzenesulfonic acid, hydroxy-O-sulfonic acid, 4-toluenesulfonic acid, galacturonic acid, embonic acid, glutamic acid and aspartic acid.

In accordance with a further aspect, the present invention provides a pharmaceutical composition useful in the prevention and treatment of the diseases caused by the activation of phosphatase, comprising the compound of chemical formula 1 or a pharmaceutically acceptable salt thereof as an active ingredient.

Having inhibitory activity against protein phosphatase, the compound of chemical compound 1 is effective in the prevention and treatment of various diseases including autoimmune disease, diabetes mellitus, impaired glucose intolerance, insulin resistance, obesity, cancers, etc.

The pharmaceutically acceptable composition comprising the compound of chemical formula 1 or a pharmaceutically acceptable salt thereof may be formulated into various oral or non-oral administration forms. For the oral administration formulations, for example, tablets, pills, hard/soft capsules, liquids, suspensions, emulsions, syrups, granules, and elixirs are available. Typically, these formulations may contain at least one expedient or carrier, such as fillers, thickeners, humectants, disintegrants, lubricants, binders, surfactants, etc., in addition to the active ingredient. Agar, starch, alginic acid or sodium alginate, or anhydrous potassium monohydrogen phosphate may be used as a disintegrant. The lubricant may be exemplified by silica, talc, stearic acid or a magnesium or potassium salt thereof; and polyethylene glycol. Examples of the binder useful in the present invention include magnesium aluminum silicate, starch paste, gelatin, traganath, methyl cellulose, sodium carboxymethyl cellulose, polyvinylpyrrolidine, and low-substituted hydroxypropylcellulose. Besides those, a diluent such as lactose, dextrose, sucrose, mannitol, sorbitol, cellulose, glycine, etc. may be used. Optionally, a general boiling mixture, an absorbent, a colorant, a flavor and a sweetener may be used alone or in combination therewith.

The pharmaceutical composition containing the compound of chemical formula 1 or a pharmaceutically acceptable salt thereof may be administered via a non-oral route. For this, the composition may be formulated into subcutaneous, intravenous, intramuscular, or intrathoracic injections. In order to obtain such non-oral administration forms, the compound of chemical formula 1 or a pharmaceutically acceptable salt thereof may be mixed with a stabilizer or a buffer in water to afford a solution or a suspension which is then packaged in ampule or vial units.

Further, the composition is sterilized and may contain an auxiliary agent, such as a preservative, a stabilizer, a wettable agent, an emulsifier, an osmotic pressure-controlling salt and a buffer, and/or other therapeutically effective materials. They may be mixed, granulated, or coated according to a method well known in the art.

As an active ingredient, the compound of chemical formula 1 may be once or many time administered to mammals including humans, at a dose of 0.1 to 500 mg/kg (body weight) a day, preferably at a dose of 0.5 to 100 mg/kg (body weight) via an oral or non-oral route.

A better understanding of the present invention may be realized with the Mowing examples, which are set forth to illustrate, but are not to be construed to limit the present invention.

MODE FOR INVENTION

Example 1

Preparation of 5-(2-benzyloxy-5-bromobenzylidene)-2-thioxo-thiazolidin-4-one (Compound 1)

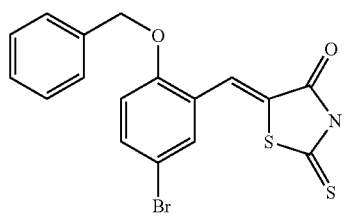

Step 1): Synthesis of 2-benzyloxy-5-bromobenzaldehyde

To a solution of 5-bromo-2-hydroxybenzaldehyde (5 g, 24.9 mmol) in acetone (200 mL) were added benzyl bromide (5.11 mL, 29.9 mmol), potassium iodide (KI, 2.07 g, 12.45 mmol) and potassium carbonate ($K_2CO_3$, 5.17 g, 37.4 mmol), followed by mixing at 70° C. for 2 hours under a reflux condition. The product thus obtained was diluted in ethyl acetate (EtOAc), washed with brine, and dried over magnesium sulfate ($MgSO_4$) to concentrate it. The concentrate was purified using silica column chromatography (10% ethyl acetate/hexane) to afford the title compound (5.88 g, 81%).

Step 2): Synthesis of 5-(2-benzyloxy-5-bromobenzylidene)-2-thioxo-thiazolidin-4-one 2-Benzyloxy-5-bromobenzaldehyde (0.29 g, 1 mmol), obtained in Step 1), was dissolved, together with 2-thioxo-thiazolidin-4-one (0.133 g, 1 mmol) and ammonium acetate (0.154 g, 2 mmol), in benzene (30 ml), and acetic acid (0.572 g, 10 mmol) was added to the solution before fluxing at 110° C. for 4 hours with stirring. Subsequently, the resulting mixture was cooled to form precipitates which were then washed with hexane and water to afford the title compound (0.289 g, 71%).

$^1$H-NMR (DMSO-$d_6$, 200 MHz) δ 13.8 (brs, 1H), 7.90-7.59 (m, 2H), 7.45-7.33 (m, 6H), 7.19 (d, J=9.0 Hz, 1H), 525 (s, 2H)

Example 2

Preparation of 5-[5-bromo-2-(2-thiopen-2-yl-ethoxy)benzylidene]-2-thioxo-thiazolidin-4-one (Compound 57)

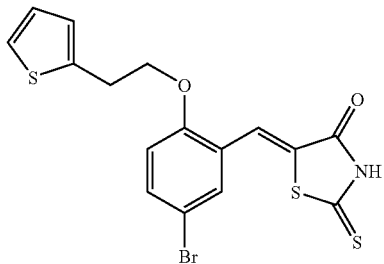

Step 1): Synthesis of 4-bromo-2-(dimethoxymethyl)phenol

To a solution of 5-bromosalicylaldehyde (4.00 g, 19.90 mmol) in methanol (50 ml) were added orthoformic acid trimethyl (9.70 g, 10.00 ml, 91.41 mmol) and TsOH.H2O (38.04 mg, 0.20 mmol), followed by reacting them at room temperature for 1 hour. Following neutralization with potassium carbonate (55.28 mg, 0.40 mmol), the solution was cleansed with brine and 5%-sodium hydrogen carbonate (=1:1, 50 ml) and extracted with pet ether (×2). A pool of the organic layer thus formed was dried over anhydrous MgSO$_4$ and filtered. The filtrate was concentrated in a vacuum to prepare the object compound (white, solid, 4.92 g, 100%).

$^1$H NMR (300 MHz, CDCl$_3$) δ 8.01 (s, 1H) 7.34-7.29 (m, 2H) 6.77 (d, J=9.1 Hz, 1H) 5.51 (s, 1H) 3.84 (s, 9H).

Step 2): 2-((4-bromo-2-(dimethoxymethyl)phenoxy)ethyl)thiophene

4-Bromo-2-(dimethoxymethyl)phenol (200 mg, 0.81 mmol), obtained in step 1), was dissolved in benzene (15 ml) to which triphenylphosphine (254.42 mg, 0.97 mmol) and 2-(2-thienyl)ethanol (124.34 mg, 0.11 ml, 0.97 mmol) were added. The reactant mixture was cooled to 0° C. in an ice bath, and diisopropyl azodicarboxylate (196.14 mg, 0.19 ml, 0.97 mmol) was dropwise added to the cooled mixture which was then allowed to react at room temperature for 30 min. Following extraction with brine and ethyl acetate, the organic layer was dried over anhydrous MgSO$_4$ and filtered. The filtrate was concentrated in a vacuum. The residue was purified through column chromatography (n-hexane→ethyl acetate:n-hexane=1:20) to prepare the object compound (colorless oil, 270 mg, 93.4%).

$^1$H NMR (200 MHz, CDCl$_3$) δ 7.65 (d, J=2.4 Hz, 1H) 7.37 (dd, J=8.7, 2.6 Hz, 1H) 7.18 (dd, J=5.0, 1.4 Hz, 1H) 6.99-6.92 (m, 2H) 6.75 (d, J=8.7 Hz, 1H) 5.57 (s, 1H) 4.21 (t, J=6.7 Hz, 1H) 3.39-3.31 (m, 8H);

m/e (relative intensity) 358 (M+2, 0) 356 (M+, 0) 294 (5) 292 (4) 111 (100) 97 (72).

Step 3): Synthesis of 2-(2-(thiopen-2-yl)ethoxy-5-bromobenzaldehyde 2-((4-Bromo-2-(dimemoxymethyl)phenoxy)ethyl)thiophene (230 mg, 0.64 mmol), obtained in step 2), was dissolved in THF (20 ml) and cooled to 0° C. before the addition of 1N—HCl (15 ml) thereto. After reaction for 1 hour, the reaction solution was neutralized with a saturated sodium hydrogen carbonate solution (ca. pH 8) and subjected to extraction with ethyl acetate. The organic layer thus formed was dried over anhydrous MgSO$_4$ and filtered. The filtrate was concentrated in a vacuum to prepare the object compound (yellowish semi-solid, 190 mg, 95.5%).

$^1$H NMR (200 MHz, CDCl$_3$) δ 10.42 (s, 1H) 7.92 (d, J=2.6 Hz, 1H) 7.60 (dd, J=8.9, 2.6 Hz, 1H) 7.18 (dd, J=5.0, 12 Hz, 1H) 6.98-6.84 (m, 3H) 4.28 (t, J=6.3 Hz, 2H) 3.38 (t, J=6.3 Hz, 2H)

Step 4): Synthesis of 5-(2-(2-(thiopen-2-yl)ethoxy)-5-bromobenzylidene)-2-thioxothiazolidin-4-one 2-(2-(Thiopen-2-yl)ethoxy)-5-bromobenzaldehyde (140 mg, 0.45 mmol), obtained in step 3), was dissolved, together with 2-thioxothiazolidin-4-one (59.94 mg, 0.45 mmol) and ammonium acetate (69.37 mg, 0.90 mmol), in benzene (15 ml), and acetic acid (270.23 mg, 0.26 ml, 4.50 mmol) was added to the solution before fluxing for 2 hours with stirring. The addition of n-hexane and water (each 510 ml) to the reaction mixture cooled resulted in the formation of yellow precipitates which were then purified in n-hexane to give the final compound of interest (white solid, 165 mg, 86.4%).

$^1$H NMR (200 MHz, DMSO-$d_6$) δ 13.81 (brs, 1H, NH) 7.76 (s, 1H) 7.62 (dd, J=8.7, 22 Hz, 1H) 7.43 (d, J=2.2 Hz, 1H) 7.34 (dd, J=4.7, 1.5 Hz, 1H) 7.15 (d, J=9.1 Hz, 1H) 6.97-6.93 (m, 2H) 4.30 (t, J=6.0 Hz, 2H) 3.31 (t, J=6.3 Hz, 2H);

m/e (relative intensive) 427 (M+2, 3) 425 (M+, 4) 111 (100) 45 (42)

Example 3

Preparation of Methanesulfonic Acid 4-bromo-2-(4-oxo-2-thioxothiazolidin-5-ylidenemethyl)phenyl ester (Compound 68)

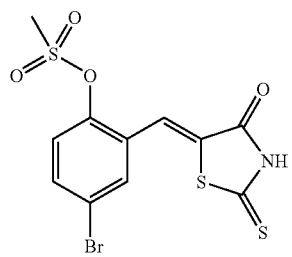

Step 1): Methanesulfonic acid 4-bromo-2-formyl ester

To a solution of 5-bromo-2-hydroxybenzaldehyde (0.5 g, 2.49 mmol) in pyridine (5 mL) was added methanesulfonyl chloride (0.342 g, 2.99 mmol), followed by stirring at room temperature 12 hours. The reaction solution was extracted with dichloromethane and the extract was washed with brine, dried over MgSO$_4$ and concentrated. The residue was purified through column chromatography (30% ethyl acetate/hexane) and concentrated to afford the object compound (0.407 g, 59%).

$^1$H NMR (CDCl$_3$, 200 MHz) δ 1021 (s, 1H), 8.07 (d, J=2.4 Hz, 1H), 7.77 (dd, J=8.8, 2.8 Hz, 1H), 7.33 (d, J=8.8 Hz, 1H), 3.32 (s, 3H);

EI-MS m/z (relative intensity) 280 (M+, 17), 200 (20), 143 (19), 79 (22), 63 (100), 53 (15)

Step 2): Synthesis of methanesulfonic acid 4-bromo-2-(4-oxo-2-thioxothiazolidin-5-ylidenemethyl)phenyl ester Methanesulfonic acid 4-bromo-2-formyl ester (0.1 g, 0.353 mmol), obtained in step 1), was dissolved together with 2-thioxothiazolidin-4-one (0.048 g, 0.358 mmol) and ammonium acetate (0.055 g, 0.717 mmol) in benzene (30 mL), and acetic acid (0.215 mL, 3.58 mmol) was added to the solution, Mowed by fluxing for 4 hours at 110° C. with stirring. The reaction solution was cooled to form precipitates which were washed with hexane and water to give the object compound (0.029 g, 21%).

$^1$H NMR (DMSO-d$_6$, 200 MHz) δ7.82 (dd, J=8.8, 2.2 Hz, 1H), 7.67-7.66 (m, 1H), 7.58-7.51 (m, 2H), 3.34 (s, 3H);

EI-MS m/z (relative intensity) 393 (M+, 10), 300 (13), 227 (37), 199 (17), 79 (74), 59 (100)

Example 4

Preparation of 5-[5-Bromo-2-(2-bromophenoxy)benzylidene]-2-thioxothiazolidin-4-one (Compound 77)

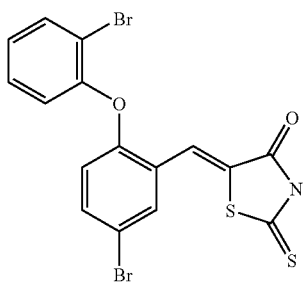

Step 1): Synthesis of 5-bromo-2-(2-bromo-phenoxy)-benzaldehyde

To a solution of 5-bromo-2-fluorobenzaldehyde (0.203 g, 1 mmol) in DMA (2.5 mL) were added 2-bromophenol (0.182 g, 1.05 mmol) and potassium carbonate (0.138 g, 1 mmol), followed by stirring at 120° C. for 12 hours. The reaction solution was diluted with ethyl acetate, washed with brine, dried over MgSO$_4$, and concentrated. The residue was purified through column chromatography (20% ethyl acetate/hexane) and concentrated to obtain the object compound (0.164 g, 46%).

$^1$H NMR (CDCl$_3$, 200 MHz) δ 10.53 (s, 1H), 8.05 (d, J=2.6 Hz, 1H), 7.69 (dd, J=7.8, 1.4 Hz, 1H), 7.55 (dd, J=6.4, 3.0 Hz, 1H), 7.41-7.33 (m, 1H), 7.19-7.08 (m, 2H), 6.80 (d, J=8.8 Hz, 1H);

EI-MS m/z (relative intensity) 356 (M+, 15), 275 (20), 200 (36), 75 (97), 63 (100), 50 (50).

Step 2): Synthesis of 5-[5-bromo-2-(2-bromophenoxy)benzylidene]-2-thioxothiazolidin-4-one 5-Bromo-2-(2-bromophenoxy)benzaldehyde (0.1 g, 0.281 mmol), obtained in step 1), was dissolved together with 2-thioxothiazolidin-4-one (0.048 g, 0.358 mmol) and ammonium acetate (0.055 g, 0.717 mmol) in benzene (30 mL) and acetic acid (0.215 mL, 3.58 mmol) was added to the solution, followed by fluxing for 4 hours at 110° C. with stirring. Cooling the reaction solution resulted in forming precipitates which were then washed with hexane and water to prepare the object compound (0.089 g, 68%).

$^1$H NMR (DMSO-d$_6$, 200 MHz) δ 7.83-7.74 (m, 2H), 7.64-7.52 (m, 2H), 7.49-729 (m, 1H), 725-7.22 (m, 2H), 6.67 (d, J=7.8 Hz, 1H);

EI-MS m/z (relative intensity) 300 (6), 120 (31), 76 (46), 59 (60), 40 (100).

Example 5

Preparation of 5-(4-Benzyloxy-4'-dimethylamino-biphenyl-3-ylmethylene)-2-thioxo-thiazolidin-4-one (Compound 95)

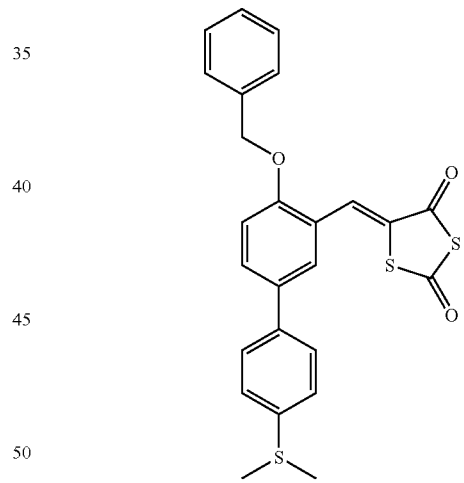

Step 1): Synthesis of 4'-dimethylamino-4-hydroxybiphenyl-3-carbaldehyde

Within a vacuum tube, 5-bromo-2-hydroxybenzaldehyde (0.5 g, 2.49 mmol), 4-dimethylaminophenyl boronic acid (0.62 g, 3.73 mg), dichloro[1,1'-ferrocenylbis(diphenylphosphine)]palladium(II)dichloromethane (Pd(dppf)Cl$_2$, 0.33 g, 0.40 mmol, 'dppf'=1,1'-bis(diphenylphospino)ferrocene) and sodium carbonate (0.53 g, 4.98 mmol) were dissolved in ethylene glycol dimethylether:water (15 ml:5 ml), followed by stirring at 100° C. for 4 hours. The reaction product thus obtained was diluted in ethyl acetate, washed with brine, dried over anhydrous MgSO$_4$, and concentrated. The concentrate was purified through column chromatography (10% ethyl acetate/hexane) and the fraction was concentrated to give 4'-dimethylamino-4-hydroxybiphenyl-3-carbaldehyde (0.383 g, 64%).

Step 2): Synthesis of 4-benzyloxy-4'-dimethylamino-biphenyl-3-carbaldehyde

The same procedure as in step 1) of Example 1 was performed in order to synthesize 4-benzyloxy-4' dimethylaminobiphenyl-3-carbaldehyde (0.114 g, 83%) from 4'-dimethylamino-4-hydroxybiphenyl-3-carbaldehyde (0.1 g, 0.41 mmol) obtained in step 1).

Step 3): Synthesis of 5-(4-benzyloxy-4'-dimethy-lamino-biphenyl-3-ylmethylene)-2-thioxo-thiazolidin-4-one 4-Benzyloxy-4' dimethylaminobiphenyl-3-carbaldehyde (0.1 g, 0.302 mmol) obtained in step 2) was reacted with 2-thioxo-thiazolidin-4-one (0.04 g, 0.302 mmol) in the same procedure as in step 2) of Example 1 to afford the object compound (0.081 g, 60%).

$^1$H-NMR (DMSO-$d_6$, 200 MHz) δ 7.89 (s, 1H), 7.68 (d, J=9.4 Hz, 1H), 7.51-7.26 (m, 3H), 6.84 (d, J=9.4 Hz, 2H), 5.30 (s, 2H), 2.94 (s, 6H)

Example 6

Preparation of 5-5-Bromo-2-[2-(3-bromophenoxy) ethoxy]benzylidene-2-thioxothiazolidin-4-one (Compound 114)

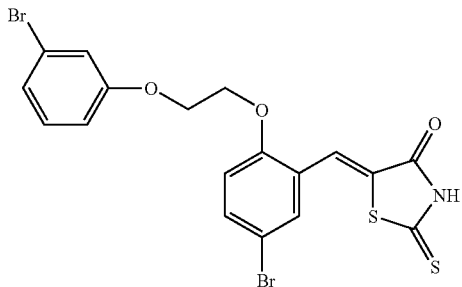

Step 1: Synthesis of 5-bromo-2-(2-bromoethoxy)benzaldehyde

To a solution of 5-bromosalicylaldehyde (5.00 g, 24.87 mmol) in DMF (200 ml) were added $K_2CO_3$ (4.47 mg, 32.34 mmol) and 1,2-dibromoethane (46.73 mg, 21.44 ml, 248.73 mmol), followed by stirring at 50° C. for 9 hours. After complete reaction, the solution was cooled to room temperature, cleansed with an aqueous saturated $NH_4Cl$ solution and extracted with ethyl acetate. The organic layer thus obtained was additionally washed once with an aqueous saturated $NH_4Cl$ solution. Then, the organic layer was dried over anhydrous $MgSO_4$ and filtered, and the filtrate was concentrated in a vacuum. The residue was subjected to column chromatography (ethyl acetate/n-hexane 1/9→1/5) to afford the object compound (yellowish solid, 300 mg, 90.1%).

Step 2: Synthesis of 5-bromo-2-[2-(3-bromophenoxy)ethoxy]benzaldehyde

5-Bromo-2-(2-bromoethoxy)benzaldehyde (170 mg, 0.55 mol) obtained in step 1) was dissolved in DMF (20 ml), and $K_2CO_3$ (229.43 mg, 1.66 mmol), KI (9.96 mg, 0.06 mmol), and 3-bromophenol (95.46 mg, 0.55 mmol) were added to the solution, followed by stirring for 2 hours at an elevated temperature. After completion of the reaction, the reaction solution was cooled to room temperature, washed with an aqueous saturated $NH_4Cl$ solution and extracted with ethyl acetate. The organic layer thus obtained was washed one more time with an aqueous saturated $NH_4Cl$ solution. Then, the organic layer was dried over anhydrous $MgSO_4$ and filtered. The filtrate was concentrated in vacuo. The residue was subjected to column chromatography (ethyl acetate/n-hexane=1/9) to afford the object compound (pale yellowish solid, 161 mg, 72.7%).

$^1$H NMR (200 MHz, $CDCl_3$) δ 10.38 (s, 1H) 7.95 (d, J=2.4 Hz, 1H) 7.65 (dd, J=8.5, 2.4 Hz, 1H) 7.17-7.09 (m, 3H) 6.95 (d, J=8.5 Hz, 1H) 6.89-6.83 (m, 1H) 4.46-4.34 (m, 4H);

mass spectrum m/e (relative intensity) 400 (M+2, 7) 398 (M+, 6) 120 (88) 63 (100).

Step 3: Synthesis of 5-5-bromo-2-[2-(3-bromophenoxy)ethoxy]benzylidene-2-thioxothiazolidin-4-one 5-Bromo-2-[2-(3-bromophenoxy)ethoxy]benzaldehyde (146 mg, 0.36 mmol) obtained in step 2 was dissolved in benzene (15 ml) and reacted with 2-thioxothiazolidin-4-one in the same procedure as in step 2) of Example 1 so as to afford the object compound (yellowish solid, 145 mg, 77.5%).

$^1$H NMR (200 MHz, DMSO-$d_6$) δ 7.70-7.64 (m, 2H) 7.49 (d, J=2.0 Hz, 1H) 7.29-7.21 (m, 3H) 7.14 (d, J=7.6 Hz, 1H) 7.01 (dd, J=8.1, 1.5 Hz, 1H) 4.46 (m, 2H) 4.41 (m, 2H);

mass spectrum m/e (relative intensity) 436 (15) 157 (24) 155 (24) 120 (87) 40 (100).

Example 7

Preparation of 5-[2-(2-Bromobenzyloxy)-(2-morpholin-4-ylethoxy)benzylidene]-2-thioxothiazolidin-4-one (Compound 149)

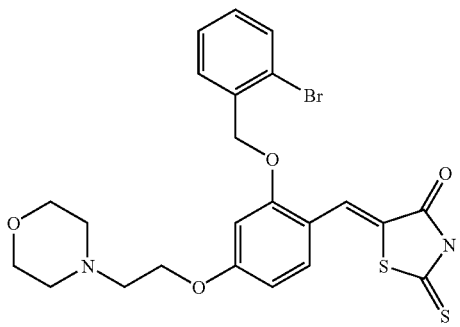

Step 1: Synthesis of 2-(2-bromobenzyloxy)-4-(tetrahydro-2H-pyran-2-yloxy)benzaldehyde With the exception that 2-hydroxy-4-(tetrahydropyran-2-yloxy)benzaldehyde (3 g, 13.45 mmol), obtained according to a method well known in the art (J. Med. Chem. 1979, 22, 1535), was used, the same procedure as in step 1 of Example 1 was conducted to synthesize the object compound (4.4 g, 83%).

Step 2: Synthesis of 2-(2-bromobenzyloxy)-4-hydroxybenzaldehyde 2-(2-Bromobenzyloxy)-4-(tetrahydro-2H-pyran-2-yloxy) benzaldehyde (4.4 g) obtained in step 1) was dissolved in a mixture of 10% HCL (30 mL) and EtOH (20 mL), followed by stirring for 1 hour and extraction with ethyl acetate. The extract was dried over MgSO$_4$ and concentrated. The solid thus formed was cleansed with hexane to afford the object compound (3.78 g, 91%).

Step 3: Synthesis of 2-(2-bromobenzyloxy)-4-(2-bromoethoxy)-benzaldehyde 2-(2-Bromobenzyloxy)-4-hydroxybenzaldehyde (1.34 g, 4.36 mmol), obtained in step 2) was dissolved in DMF, and K$_2$CO$_3$ (3.01 g, 21.8 mmol) and dibromoethane (8.19 g, 43.6 mmol) were added to the solution, followed by stirring for 18 hours. Then, the reaction solution was cooled, filtered, washed with brine and extracted with CH$_2$Cl$_2$. The extract was dried over anhydrous MgSO$_4$ and filtered, and the filtrate was concentrated in vacuo to afford the object compound (white solid, 1.68 g, 93%).

Step 4: Synthesis of 2-(2-bromobenzyloxy)-4-(2-morpholin-4-yl-ethoxy)benzaldehyde 2-(2-Bromobenzyloxy)-4-(2-bromoethoxy)benzaldehyde (100 mg, 0.241 mmol) synthesized in step 3 was dissolved in acetone, and K$_2$CO$_3$ (66.6 mg, 0.482 mmol), NaI (3.6 mg, 0.024 mmol), and morpholine (0.032 ml, 0.362 mmol) were added to the solution, followed by flux with stirring. After stirring for 24 hours, the solution was cooled, filtered, washed with brine, and extracted with CH$_2$Cl$_2$. Then, the extract was dried over anhydrous MgSO$_4$ and filtered and the filtrate was concentrated in a vacuum. The residue was subjected to column chromatography (50% EA/Hx) to afford the object compound (yellowish oil, 52 mg, 51%).

$^1$H NMR (200 MHz, CDCl$_3$) δ 10.41 (s, 1H), 7.84 (d, J=8.3 Hz, 1H), 7.63-7.50 (m, 2H), 7.40-7.33 (m, 1H), 7.26-7.19 (m, 1H), 6.60-6.55 (m, 2H), 5.21 (s, 2H), 4.16 (t, J=5.7 Hz, 2H), 3.74 (t, J=4.8 Hz, 4H), 2.81 (t, J=5.7 Hz, 2H), 2.57 (t, J=4.8 Hz, 4H);

mass spectrum m/e (relative intensity) 419 (M+, 0.2), 293 (9), 149(34), 100(85), 42 (100).

Step 5: Synthesis of 5-[2-(2-bromobenzyloxy)-4-(2-morpholin-4-ylethoxy)benzylidene]-2-thioxothiazolidin-4-one (Compound 161)

2-(2-Bromobenzyloxy)-4-(2-morpholin-4-yl-ethoxy)benzaldehyde (43 mg, 0.102 mmol) obtained in step 4 was dissolved in benzene and reacted with 2-thioxothiazolidin-4-one in the same manner as in step 2 of Example 1 to afford the object compound (yellowish solid, 25 mg, 46%).

$^1$H NMR (200 MHz, DMSO-d$_6$) δ 7.74-7.70 (m, 2H), 7.61-7.58 (m, 1H), 7.49-7.31 (m, 3H), 6.82-6.75 (m, 2H), 5.26 (s, 2H), 4.22 (t, J=5.9 Hz, 2H), 3.61 (t, J=4.6 Hz, 4H), 2.81 (t, J=5.9 Hz, 2H), 2.49 (t, J=4.6 Hz, 4H);

mass spectrum m/e (relative intensity) 534 (M+, 0.5), 169 (5), 114(26), 100 (100).

Example 8

Preparation of 1-2-[4-Bromo-2-(4-oxo-2-thioxothiazolidin-5-ylidenemethyl)phenoxy]ethyl-3-ethyl-1-methylurea (Compound 161)

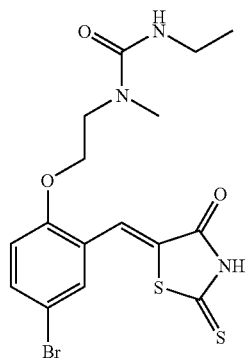

Step 1: Synthesis of t-butyl 2-hydroxyethylmethylcarbamate

To a solution of 2-(methylamino)ethanol (500 mg, 0.53 ml, 6.66 mmol) in CH$_2$Cl$_2$ (20 ml) was added Boc$_2$O (1.48 g, 6.79 mmol), followed by stirring at room temperature for 1 hour. The reaction solution was extracted with brine and CH$_2$Cl$_2$. The organic layer thus obtained was dried over MgSO$_4$ and filtered. Then, the filtrate was concentrated in vacuo to obtain the object compound (colorless oil, quantitative);

$^1$H NMR (200 MHz, CDCl$_3$) δ 3.74 (q, J=10.5, 5.2 Hz, 2H) 3.25 (t, J=5.2 Hz, 2H) 2.91 (s, 3H) 1.45 (s, 9H);

mass spectrum m/e (relative intensity) 144 (20) 102 (24) 57 (70) 44 (100).

Step 2: Synthesis of t-butyl 2-(4-bromo-2-(dimethoxymethyl)phenoxy)ethylmethylcarbamate To a solution of 4-bromo-2-dimethoxymethylphenol (6.00 g, 24.3 mmol) in benzene (100 ml) were added triphenylphosphine (7.63 g, 29.1 mmol) and t-butyl 2-hydroxyethylmethylcarbamate (5.10 g, 29.1 mmol) synthesized in step 1). The reaction solution was cooled to 0° C. in an ice bath, and diisopropyl azodicarboxylate (5.88 g. 5.73 ml, 29.1 mmol) was dropwise added thereto, after which it was allowed to react for 1 hour. Following extraction with brine and ethyl acetate, the organic layer was dried over anhydrous MgSO$_4$ and filtered. The filtrate was concentrated in a vacuum. The residue was purified through column chromatography (ethyl acetate/n-hexane=1/20) to afford the object compound (colorless oil, 11.30 g, 96.1%).

$^1$H NMR (200 MHz, CDCl$_3$) δ 7.65 (d, J=2.4 Hz, 1H) 7.38 (dd, J=8.9, 2.8 Hz, 1H) 6.75 (d, J=8.9 Hz, 1H) 5.57 (s, 1H) 4.09 (m, 2H) 3.62 (m, 2H) 3.34 (s, 6H) 2.99 (s, 3H) 1.46 (s, 9H);

mass spectrum m/e (relative intensity) 390 (1) 216 (16) 102 (100) 57 (87).

Step 3: Synthesis of t-butyl 2-(4-bromo-2-formylphenoxy)-ethylmethylcarbamate t-Butyl 2-(4-bromo-2-(dimethoxymethyl)phenoxy)ethylmethylcarbamate (300 mg; 0.74 mmol) obtained in step 2 was dissolved in THF (15 ml) and was added to the solution at 0° C., 1N—HCl (20 ml). Following reaction for 2 hours, the solution was neutralized with a saturated aqueous NaHCO₃ solution (ca. pH 8) and extracted with ethyl acetate. The organic layer thus formed was dried over anhydrous MgSO₄ and filtered. The filtrate was concentrated in vacuo and purified through column chromatography (ethyl acetate/n-hexane=1/9) to afford the object compound (colorless oil 1,259 mg, 98.4%).

$^1$H NMR (200 MHz, CDCl₃) δ 10.4 (s, 1H) 7.93 (d, J=2.8 Hz, 1H) 7.62 (dd, J=8.9, 2.8 Hz, 1H) 6.89 (d, J=8.9 Hz, 1H) 4.20 (m, 2H) 3.68 (t, J=5.2 Hz, 2H) 2.98 (s, 3H) 1.47 (s, 9H).

Step 4: Synthesis of 5-bromo-2-(2-methylaminoethoxy)-benzaldehyde trifluoro acetic acid To a solution of t-butyl 2-(4-bromo-2-formylphenoxy)ethylmethylcarbamate (1.26 g, 3.52 mmol) in CH₂Cl₂ (50 ml) was added TFA (4.01 g, 2.71 mmol 35.17 mmol) at 0° C., followed by stirring for 9 hours. Thereafter, the reaction solution was concentrated in a vacuum and completely dried to afford the object compound (dark brown oil, suitable amount).

$^1$H NMR (200 MHz, CDCl₃) δ9.64 (brs, acid, TFA) 8.95 (s, 1H) 7.85 (d, J=2.0 Hz, 1H) 7.79 (dd, J=8.7, 22 Hz, 1H) 7.09 (d, J=8.7 Hz, 1H) 4.61 (m, 2H) 429 (m, 2H) 3.64 (s, 3H);

mass spectrum m/e (relative intensity) 214 (13) 212 (14) 69 (61) 44 (100).

Step 5: Synthesis of 1-[2-(4-bromo-2-formylphenoxy)ethyl]-3-ethyl-1-methylurea

5-Bromo-2-(2-methylaminoethoxy)benzaldehyde trifluoro acetic acid (400 mg, 1.07 mmol), obtained in step 4, dissolved in CH₂Cl₂ (20 ml) and Et₃N (130.33 mg, 0.18 ml, 129 mmol) was added to the solution, followed by stirring for 2~3 min. After the addition of ethyl isocyanate (76.40 mg, 85 µl, 1.07 mmol), the solution was allowed to react at room temperature for 1 hour. Thereafter, the reaction solution was extracted with brine and CH₂Cl₂ (×3), and the organic layer thus obtained was dried over anhydrous MgSO₄ and filtered. The filtrate was concentrated in a vacuum. The residue was purified through column chromatography (ethyl acetate/n-hexane=1/1→CH₂Cl₂/CH₃OH→98/2) to afford the object compound (pale yellowish solid, 204 mg, 57.7%).

$^1$H NMR (200 MHz, CDCl₃) δ 10.35 (s, 1H, CHO) 7.91 (d, J=2.6 Hz, 1H) 7.62 (dd, 7=8.9, 2.6 Hz, 1H) 6.91 (d, J=8.9 Hz, 1H) 4.49 (bis, 1H, NH) 422 (t, J=52 Hz, 2H) 3.75 (t, J=5.2 Hz, 2H) 3.34-3.21 (m, 2H) 3.00 (s, 1H, N—CH₃) 1.15 (% J=7.1 Hz, 3H);

mass spectrum m/e (relative intensity) 330 (M+2, 0.2) 328 (M+, 0.2) 129 (19) 57 (32) 44 (100).

Step 6: Synthesis of 1-2-[4-bromo-2-(4-oxo-2-thioxothiazolidin-5-ylidenemethyl)phenoxy]ethyl-3-ethyl-1-methylurea 1-[2-(4-Bromo-2-formylphenoxy)ethyl]-3-ethyl-1-methylurea (140 mg, 0.43 mmol) obtained step 5 was dissolved in benzene (15 ml) and reacted with 2-thioxothiazolidin-4-one in the same procedure as in step 2 of Example 1 to afford the object compound (yellowish solid, 31 mg, 16.2%).

$^1$H NMR (200 MHz, DMSO-d₆) δ 7.71 (s, 1H) 7.62 (dd, J=8.9, 2.4 Hz, 2H) 7.43 (d, J=2.2 Hz, 1H) 7.16 (d, J=8.9 Hz, 1H) 6.28 (t, J=4.9 Hz, 1H, NH) 4.17 (t, J=5.5 Hz, 2H) 3.60 (t, J=5.5 Hz, 2H) 3.03 (q, J=19.4, 13.8, 6.8 Hz, 2H) 2.89 (s, 3H, N—CH₃) 0.98 (t, J=7.2 Hz, 3H);

mass spectrum m/e (relative intensity) 258 (4) 256 (4) 149 (3) 129 (25) 44 (100).

Example 9

Preparation of N-2-[3-(2-Bromobenzyloxy)-4-((4-oxo-2-thioxothiazolidin-5-ylidene)methyl)phenoxy]ethylbenzamide (Compound 169)

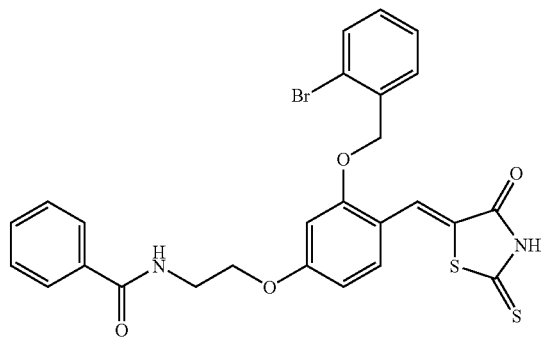

Step 1: Synthesis of t-butyl-2-(3-(2-bromobenzyloxy)-4-formylphenoxy)ethylcarbamate To a solution of 2-(2-bromobenzyloxy)-4-hydroxybenzaldehyde (60 mg, 020 mmol) in DMF (10 ml) were added t-butyl-2-bromoethylcarbamate (43.70 g, 0.20 mmol) and K₂CO₃ (54.18 mg, 0.39 mmol), followed by stirring at 100° C. for 3 hours. After completion of the reaction, the solution was extracted with a saturated aqueous NH₄Cl solution and ethyl acetate. The organic layer was dried over anhydrous MgSO₄ and filtered. The filtrate was concentrated in a vacuum. The residue was purified through column chromatography (ethyl acetate/n-hexane=1/9→1/5) to afford the object compound (pale yellowish solid, 69 mg, 79.3%).

$^1$H NMR (200 MHz, CDCl₃) δ 10.39 (s, 1H), 7.83 (d, J=8.5 Hz, 1H), 7.63-7.53 (m, 2H), 7.36 (t, J=7.5 Hz, 1H), 7.25-7.18 (m, 1H), 6.59-6.53 (m, 2H), 5.21 (s, 2H), 4.99 (brs, 1H), 4.07 (t, J=4.4 Hz, 2H), 3.54 (q, J=10.9, 5.4 Hz, 2H), 1.45 (s, 9H);

mass spectrum m/e (relative intensity) 451 (M+2, 1), 449 (M+, 1), 394 (1), 169 (85), 88 (80), 57 (100).

Step 2: Synthesis of 4-(2-aminoethoxy)-2-(2-bromobenzyloxy)benzaldehyde

A solution of t-butyl-2-(3-(2-bromobenzyloxy)-4-formylphenoxy)ethylcarbamate (449 mg, 1 mmol) in CH₂Cl₂ was cooled to 0° C., and TEA (30 eq.) was dropwise added to the solution, followed by stirring for 2 hours. Thereafter, the reaction solution was concentrated in a vacuum and completely dried to prepare the object compound (448 mg, 100%), which was immediately used in the subsequent reaction. For NMR analysis, the product was treated with Et₃N to form a free amine which was then dissolved in CDCl₃.

$^1$H NMR (200 MHz, CDCl₃) δ 10.41 (s, 1H) 7.85 (d, J=8.5 Hz, 1H) 7.64-7.53 (m, 2H) 7.41-7.33 (m, 1H) 7.27-7.19 (m, 1H) 6.76 (brs, NH₂) 6.59-6.52 (m, 2H) 5.23 (s, 2H) 4.17 (t, J=4.8 Hz, 2H) 3.82 (q, J=10.5, 5.1 Hz, 2H).

Step 3: Synthesis of N-(2-(3-(2-bromobenzyloxy)-4-formylphenoxy)ethyl)benzamide 4-(2-Aminoethoxy)-2-(2-bromobenzyloxy)benzaldehyde (200 mg, 0.43 mmol) was dissolved in $CH_2Cl_2$ (20 ml) and $Et_3N$ (87.02 mg, 0.12 ml, 0.86 mmol) was added to the solution, followed by stirring for 2~3 min. Benzoyl chloride (60.45 mg, 50 μl, 0.43 mmol) was also added before additionally stirring at room temperature for 2 hours. After completion of the reaction, the reaction solution was extracted with brine and $CH_2Cl_2$ (×3). The organic layer was dried over anhydrous $MgSO_4$ and filtered. The filtrate was concentrated in a vacuum. The residue was purified using column chromatography (ethyl acetate/n-hexane=1/5→1/3) to afford the object compound (white solid, 78 mg, 40%).

$^1$H NMR (200 MHz, $CDCl_3$) δ 10.40 (s, 1H), 7.92-7.80 (m, 3H), 7.76-7.37 (m, 6H), 7.33-7.19 (m, 2H), 6.62-6.55 (m, 3H), 5.22 (s, 2H), 4.23 (t, J=5.2 Hz, 2H), 3.91 (t, J=5.2 Hz, 2H);

mass spectrum m/e (relative intensity) 454 (M+, 0.5), 169 (123), 148 (100), 105 (53).

Step 4: Synthesis of N-2-[3-(2-bromobenzyloxy)-4-((4-oxo-2-thioxothiazolidin-5-ylidene)methyl)phenoxy]ethylbenzamide N-(2-(3-(2-Bromobenzyloxy)-4-formylphenoxy)ethyl) benzamide (60 mg, 0.13 mmol), obtained in step 3, was dissolved in benzene (10 ml) and reacted with 2-thioxothiazolidin-4-one in the same manner as in step 2 of Example 1 to synthesize the object compound (yellowish solid, 65 mg, 87.8%).

$^1$H NMR (200 MHz, DMSO-$d_6$) δ 8.72 (m, 1H) 7.88-7.84 (m, 2H) 7.78 (s, 1H) 7.71 (d, J=8.8 Hz, 1H) 7.61-7.32 (m, 7H) 6.86-6.78 (m, 2H) 5.26 (s, 2H) 4.24 (t, J=5.3 Hz, 2H) 3.68 (t, J=5.3 Hz, 2H);

mass spectrum m/e (relative intensity) 169 (22), 148 (100), 105 (46), 77 (45).

Structural formulas of the rhodanine derivatives prepared according to the method described in one of Examples 1 to 9 are given, together with $^1$H NMR data thereof, in Table 1~9, below.

TABLE 1

Compounds Prepared According to Method of Example I and Equivalent Methods

| Nos. | Cpd. Structure | $^1$H-NMR (DMSO-$d_6$, 200 MHz) δ |
|---|---|---|
| 1 | (structure) | 13.8 (brs, 1 H), 7.90-7.59 (m, 2 H), 7.45-7.33 (m, 6 H), 7.19 (d, J = 9.0 Hz, 1 H), 5.25 (s, 2 H), (Example 1) |
| 2 | (structure) | 13.85 (brs, 1 H), 8.04-7.79 (m, 3 H), 7.55 (d, J = 6.6 Hz, 1 H), 7.46-7.39 (m, 8 H), 5.32 (s, 2 H) |
| 3 | (structure) | 8.05 (m, 2 H), 7.92 (d, J = 7.2 Hz, 1 H), 7.79 (d, J = 8.4 Hz, 1 H), 7.57-7.28 (m, 8 H), 5.41 (s, 2 H) |
| 4 | (structure) | 7.66-7.60 (m, 2 H), 7.57-7.10 (m, 7 H), 4.28 (t, J = 6.4 Hz, 2 H), 3.06 (t, J = 6.4 Hz, 2 H) |

TABLE 1-continued

Compounds Prepared According to Method of Example I and Equivalent Methods

| Nos. | Cpd. Structure | $^1$H-NMR (DMSO-$d_6$, 200 MHz) δ |
|---|---|---|
| 5 | | 7.73 (s, 1 H), 7.60 (dd, J = 2.4, 8.6 Hz, 1 H), 7.40 (s, 1 H), 7.12 (d, J = 9.0 Hz, 1 H), 3.86 (d, J = 6.6 Hz, 2 H), 2.08 (qin, 1 H), 0.98 (d, J = 6.6 Hz, 6 H) |
| 6 | | 8.35 (s, 1 H), 7.93-7.86 (m, 2 H), 7.79-7.51 (m, 2 H), 7.65-7.36 (m, 6 H), 5.31 (s, 2 H) |
| 7 | | 7.81 (s, 1 H), 7.44-7.30 (m, 10 H), 6.91 (m, 2 H), 5.19 (s, 2 H) |
| 8 | | 8.39-8.33 (m, 1 H), 8.21-8.21 (m, 1 H), 7.76-7.73 (m, 1 H), 7.74-7.41 (m, 6 H), 5.44 (s, 2 H) |
| 9 | | 7.97 (m, 1 H), 7.44-7.34 (m, 7 H), 4.95 (s, 2 H) |

TABLE 1-continued

Compounds Prepared According to Method of Example I and Equivalent Methods

| Nos. | Cpd. Structure | $^1$H-NMR (DMSO-d$_6$, 200 MHz) δ |
|---|---|---|
| 10 | | 7.85 (s, 1 H), 7.42-7.37 (m, 6 H), 6.77-6.71 (m, 2 H), 5.27 (s, 2 H) |
| 11 | | 7.90 (s, 1 H) 7.41-7.35 (m, 15 H), 6.49 (s, 2 H), 5.30 (s, 4 H), 5.14 (s, 2 H) |
| 12 | | 8.26 (s, 1 H), 7.90 (d, J = 8.3 Hz, 1 H), 7.74-7.63 (m, 3 H), 7.53 (s, 1 H), 7.20 (d, J = 8.3 Hz, 1 H), 5.61 (s, 2 H) |
| 13 | | 7.75-7.70 (m, 1 H), 7.54-7.34 (m, 6 H), 5.30 (s, 2 H) |

TABLE 1-continued
Compounds Prepared According to Method of Example I and Equivalent Methods
| Nos. | Cpd. Structure | $^1$H-NMR (DMSO-$d_6$, 200 MHz) δ |
|---|---|---|
| 14 | 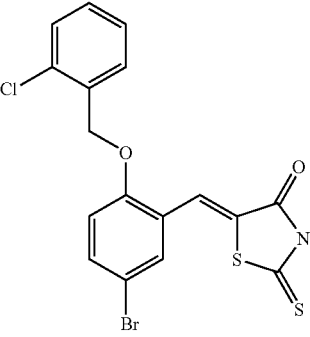 | 7.71 (s, 1 H), 7.58-7.39 (m, 5 H), 7.25 (d, J = 9.0 Hz, 1 H), 5.32 (s, 2 H) |
| 15 | 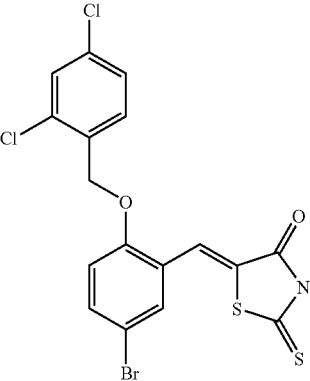 | 7.74-7.62 (m, 4 H), 7.58-7.48 (m, 2 H), 7.24 (d, J = 9.0 Hz, 1 H), 5.30 (s, 2 H) |
| 16 | 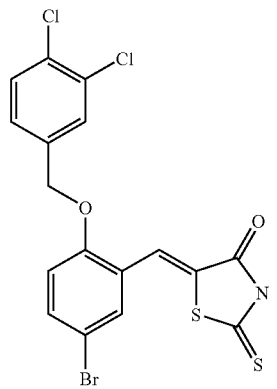 | 7.76 (s, 1 H), 7.67-7.65 (m, 3 H), 7.51-7.43 (m, 2 H), 7.19 (d, J = 9.4 Hz, 1 H), 5.29 (s, 2 H) |
| 17 | 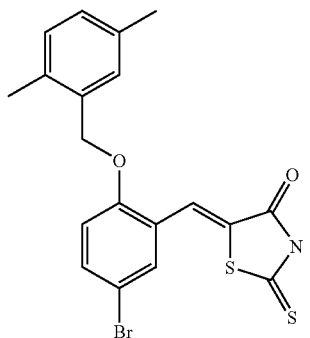 | 7.67-7.64 (m, 2 H), 7.44 (m, 1 H), 7.29-7.21 (m, 2 H), 7.15-7.05 (m, 2 H), 5.18 (s, 2 H), 2.26 (s, 6 H) |

TABLE 1-continued

Compounds Prepared According to Method of Example I and Equivalent Methods

| Nos. | Cpd. Structure | $^1$H-NMR (DMSO-$d_6$, 200 MHz) δ |
|---|---|---|
| 18 | | 7.73-7.63 (m, 6 H), 7.66-7.33 (m, 6 H), 7.24 (d, J = 8.8 Hz, 1 H), 5.32 (s, 2 H) |
| 19 | | 7.84 (s, 1 H), 7.72-7.65 (m, 5 H), 7.48 (s, 1 H), 7.21 (d, J = 8.8 Hz, 1 H), 5.37 (s, 2 H) |
| 20 | | 7.75 (s, 1 H), 7.65 (dd, J = 2.4, 9.0 Hz, 1 H), 7.47 (s, 1 H), 7.21 (d, J = 9.0 Hz, 1 H), 6.61 (s, 2 H), 6.46 (s, 1 H), 5.20 (s, 2 H) |
| 21 | | 7.71 (d, J = 9.2 Hz, 1 H), 7.59-7.48 (m, 3 H), 7.36 (d, J = 8.8 Hz, 1 H), 7.24-7.16 (m, 2 H), 5.28 (s, 2 H) |

TABLE 1-continued

Compounds Prepared According to Method of Example I and Equivalent Methods

| Nos. | Cpd. Structure | $^1$H-NMR (DMSO-d$_6$, 200 MHz) δ |
|---|---|---|
| 22 | | 7.68-7.58 (m, 4 H), 7.46-7.37 (m, 3 H), 7.16 (d, J = 8.8 Hz, 1 H), 5.24 (s, 2 H) |
| 23 | | 7.66 (s, 1 H), 7.56-7.53 (m, 3 H), 7.45-7.36 (m, 3 H), 7.12 (d, J = 9.0 Hz, 1 H), 5.24 (s, 2 H) |
| 24 | | 7.73-7.65 (m, 3 H), 7.57 (d, J = 7.0 Hz, 1 H), 7.48-7.23 (m, 4 H), 5.27 (s, 2 H) |
| 25 | | 8.14 (d, J = 7.6 Hz, 1 H), 7.83-7.60 (m, 5 H), 7.49 (s, 1 H), 7.18 (d, J = 8.6 Hz, 1 H), 5.61 (s, 2 H) |

TABLE 1-continued

Compounds Prepared According to Method of Example I and Equivalent Methods

| Nos. | Cpd. Structure | ¹H-NMR (DMSO-d$_6$, 200 MHz) δ |
|---|---|---|
| 26 | | 7.98 (s, 1 H) 7.48-7.45 (m, 2 H) 7.31-7.18 (m, 5 H) 6.77 (d, J = 9.3 Hz, 1 H) 4.04 (t, J = 6.6 Hz, 2 H) 2.27 (t, J = 7.5 Hz, 2 H) 2.19 (quin, J = 6.9, 4.6, 2.3 Hz, 2 H) |
| 27 | | 9.16 (brs, NH) 7.98 (s, 1 H) 7.48-7.44 (m, 2 H) 7.32-7.26 (m, 3 H) 7.22-7.18 (m, 2 H) 6.47 (d, J = 9.3 Hz, 1 H) 4.04 (t, J = 6.5 Hz, 2 H) 2.82 (t, J = 7.5 Hz, 2 H) 2.22 (quin, J= 9.2, 6.9, 2.3 Hz, 2 H) |
| 28 | | 7.87 (s, 1 H), 7.51-7.32 (m, 7 H), 7.26-7.22 (m, 1 H), 7.15-7.08 (m, 1 H), 5.26 (s, 2 H) |
| 29 | | 78.04-7.85 (m, 3 H), 7.73-7.60 (m, 2 H), 7.58-7.33 (m, 5 H), 5.38 (s, 2 H) |
| 30 | | 78.10-7.81 (m, 4 H), 7.56-7.40 (m, 3 H), 6.71 (s, 2 H), 6.49 (s, 1 H), 5.28 (s, 2 H), 3.77 (s, 6 H) |

TABLE 1-continued

Compounds Prepared According to Method of Example I and Equivalent Methods

| Nos. | Cpd. Structure | $^1$H-NMR (DMSO-$d_6$, 200 MHz) δ |
| --- | --- | --- |
| 31 | | 8.06-7.98 (m, 4 H), 7.86-7.71 (m, 1 H), 7.68-7.60 (m, 7 H), 7.56-7.37 (m, 4 H), 5.40 (s, 2 H) |
| 32 | | 7.84 (s, 1 H), 7.49-7.33 (m, 5 H), 7.18 (d, J = 8.8 Hz, 1 H), 6.45 (d, J = 9.4 Hz, 1 H), 6.26 (s, 1 H), 5.29 (s, 2 H), 3.35 (q, J = 6.4 Hz, 4 H), 1.06 (t, J = 6.4 Hz, 6 H) |
| 33 | | 7.86 (s, 1 H), 7.74-7.66 (m, 4 H), 7.58-7.36 (m, 5 H), 7.19 (d, J = 8.8 Hz, 1 H), 6.46 (d, J = 8.0 Hz, 1 H), 6.30 (s, 1 H), 5.34 (s, 2 H), 3.39 (q, J = 6.6 Hz, 4 H), 1.05 (t, J = 6.6 Hz, 6 H) |
| 34 | | 7.69 (s, 1 H), 7.59-7.29 (m, 3 H), 7.18 (d, J = 9.2 Hz, 1 H), 6.52-6.44 (m, 2 H), 5.33 (s, 2 H), 3.46 (q, J = 7.0 Hz, 4 H), 1.14 (t, J = 7.0 Hz, 6 H) |

TABLE 1-continued

Compounds Prepared According to Method of Example I and Equivalent Methods

| Nos. | Cpd. Structure | $^1$H-NMR (DMSO-$d_6$, 200 MHz) δ |
|---|---|---|
| 35 | | 7.90 (s, 1 H), 7.37 (s, 1 H), 7.19 (d, J = 9.6 Hz, 1 H), 6.64 (s, 2 H), 6.48-6.46 (m, 2 H), 6.28 (s, 1 H), 5.22 (s, 2 H), 3.75 (s, 6 H), 3.42 (q, J = 6.6 Hz, 4 H), 1.07 (t, J = 6.6 Hz, 6 H) |
| 36 | | 7.84 (s, 1 H), 7.36-7.32 (m, 3 H), 6.50-6.40 (m, 1 H), 6.21 (s, 1 H), 4.29 (t, J = 7.2 Hz, 2 H), 3.44 (q, J = 7.0 Hz, 2 H), 3.10 (t, J = 7.2 Hz, 2 H), 1.12 (t, J = 7.0 Hz, 6 H) |
| 37 | | 8.16 (d, J = 9.0 Hz, 1 H), 8.01-7.91 (m, 2 H), 7.83-7.61 (m, 2 H), 7.57-7.22 (m, 5 H), 5.42 (s, 2 H) |
| 38 | | 8.10-8.06 (m, 2 H), 7.93 (d, J = 8.0 Hz, 1 H), 7.82 (d, J = 8.0 Hz, 1 H), 7.65-7.43 (m, 3 H), 6.61 (s, 2 H), 6.42 (s, 1 H), 5.36 (s, 2 H), 3.71 (s, 6 H) |
| 39 | | 7.75 (s, 1 H) 7.34-7.30 (m, 3 H) 7.23-7.16 (m, 1 H) 7.07-6.92 (m, 2 H) 6.78 (d, J = 9.5 Hz, 1 H) 5.09 (s, 2 H) |

TABLE 1-continued
Compounds Prepared According to Method of Example I and Equivalent Methods
| Nos. | Cpd. Structure | $^1$H-NMR (DMSO-$d_6$, 200 MHz) δ |
|---|---|---|
| 40 | 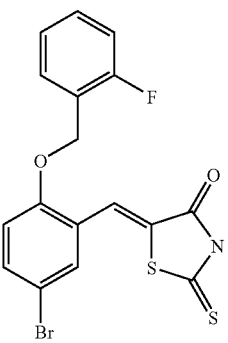 | 7.76 (s, 1 H), 7.41-7.28 (m, 2 H), 7.21-7.17 (m, 2 H), 7.09-6.97 (m, 2 H), 6.89 (d, J = 8.0 Hz, 1 H), 5.12 (s, 2 H) |
| 41 | 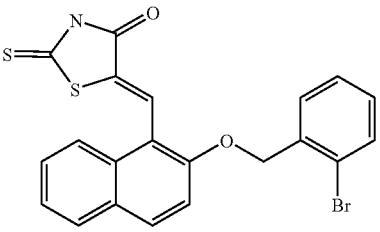 | 8.13-8.02 (m, 1 H), 7.98-7.95 (m, 2 H), 7.68 (d, J = 7.8 Hz, 1 H), 7.01-7.25 (m, 7 H), 5.41 (s, 2 H) |
| 42 | 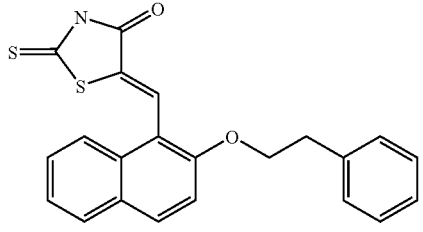 | 8.07 (d, J = 9.2 Hz, 1 H), 7.95-7.92 (m, 2 H), 7.76 (d, J = 8.6 Hz, 1 H), 7.61-7.40 (m, 3 H), 7.36-7.21 (m, 5 H), 4.48 (t, J = 6.4 Hz, 2 H), 3.09 (t, J = 6.4 Hz, 2 H) |
| 43 | 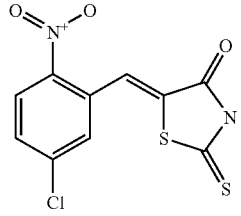 | 8.24 (d, J = 8.8 Hz, 1 H), 7.83-7.69 (m, 3 H) |
| 44 | 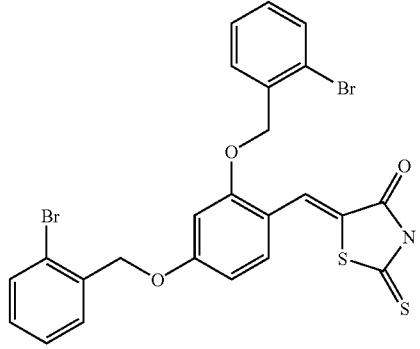 | 7.81 (s, 1 H), 7.74-7.58 (m, 4 H), 7.08-7.30 (m, 5 H), 6.96-6.84 (m, 2 H), 5.28 (s, 2 H), 5.24 (s, 2 H) |

TABLE 1-continued

Compounds Prepared According to Method of Example I and Equivalent Methods

| Nos. | Cpd. Structure | $^{1}$H-NMR (DMSO-$d_6$, 200 MHz) δ |
|---|---|---|
| 45 | | 7.81 (s, 1 H), 7.61-7.31 (m, 8 H), 7.18 (s, 1 H), 6.89 (d, J = 8.4 Hz, 1 H), 5.29 (s, 4 H) |
| 46 | | 7.71 (s, 1 H), 7.68-7.51 (m, 2 H), 7.45-7.20 (m, 10 H), 6.96 (d, J = 8.0 Hz, 1 H), 5.24 (s, 2 H), 5.04 (s, 2 H) |
| 47 | | 7.84 (s, 1 H), 7.46-7.31 (m, 5 H), 7.24-7.05 (m, 2 H), 6.90-6.86 (m, 1 H), 5.22 (s, 2 H), 3.79 (s, 3 H) |
| 48 | | 13.6 (br, 1 H), 10.54 (brs, 1 H), 7.80 (s, 1 H), 7.72-7.23 (m, 5 H), 6.59-6.55 (m, 2 H), 5.20 (s, 2 H) |

TABLE 1-continued
Compounds Prepared According to Method of Example I and Equivalent Methods
| Nos. | Cpd. Structure | ¹H-NMR (DMSO-d$_6$, 200 MHz) δ |
|---|---|---|
| 49 | 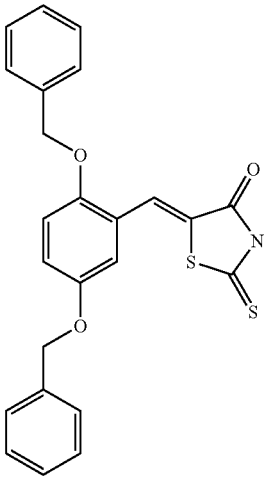 | 7.79 (s, 1 H), 7.47-7.33 (m, 10 H), 721-7.11 (m, 2 H), 6.91 (s, 1 H), 5.19 (s, 2 H), 5.12 (s, 2 H) |
| 50 | 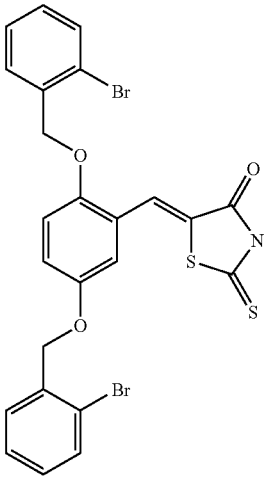 | 7.79 (s, 1 H), 7.72-7.70 (m, 2 H), 7.69-7.55 (m, 2 H), 7.47-7.23 (m, 7 H), 6.93 (s, 1 H), 5.21 (s, 2 H), 5.16 (s, 2 H) |
| 51 | 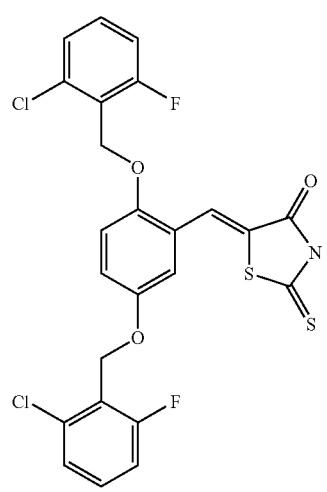 | 7.64 (s, 1 H), 7.57-7.28 (s, 8 H), 6.98 (s, 1 H), 5.25 (s, 2 H), 5.18 (s, 2 H) |

TABLE 1-continued

Compounds Prepared According to Method of Example I and Equivalent Methods

| Nos. | Cpd. Structure | $^1$H-NMR (DMSO-$d_6$, 200 MHz) δ |
|---|---|---|
| 52 | | 7.63 (dd, J = 8.5, 2.4 Hz, 2 H) 7.58 (s, 2 H) 7.42 (d, J = 2.4 Hz, 2 H) 7.22 (d, J = 8.9 Hz, 2 H) 4.53 (s, 4 H) |
| 53 | | 7.83 (s, 1 H), 7.52 (dd, J = 2.4, 9.3 Hz, 1 H), 7.46-7.22 (m, 6 H), 7.01 (d, J = 8.4 Hz, 1 H), 5.68 (q, J = 6.6 Hz, 1 H), 1.62 (d, J = 6.6 Hz, 3 H) |
| 54 | | 7.68-7.60 (m, 2 H), 7.47 (d, J = 2.4 Hz, 1 H), 7.15 (d, J = 9 Hz, 1 H), 5.46 (t, J = 7.2 Hz, 1 H), 4.68 (d, J = 7.5 Hz, 2 H), 1.75 (d, J = 7.8 Hz, 6 H) |
| 55 | | 8.10 (d, J = 7.5 Hz, 2 H), 7.81 (s, 1 H), 7.64-7.40 (m, 5 H), 6.54 (d, J = 9.9 Hz, 1 H), 1.73 (s, 6 H) |

TABLE 1-continued

Compounds Prepared According to Method of Example 1 and Equivalent Methods

| Nos. | Cpd. Structure | $^1$H-NMR (DMSO-$d_6$, 200 MHz) δ |
|---|---|---|
| 56 | | 7.91 (s, 1 H), 7.60-7.20 (m, 12 H), 7.10 (d, J = 8.7 Hz, 1 H), 6.73 (s, 1 H) |

TABLE 2

Compounds Prepared According to Method of Example 2 and Equivalent Methods

| Nos. | Cpd. Structure | $^1$H-NMR (DMSO-$d_6$, 200 MHz) δ |
|---|---|---|
| 57 | | 13.81 (brs, 1 H, NH) 7.76 (s, 1 H) 7.62 (dd, J = 8.7, 2.2 Hz, 1 H) 7.43 (d, J = 2.2 Hz, 1 H) 7.34 (dd, J = 4.7, 1.5 Hz, 1 H) 7.15 (d, J = 9.1 Hz, 1 H) 6.97-6.93 (m, 2 H) 4.30 (t, J = 6.0 Hz, 2 H) 3.31 (t, J = 6.3 Hz, 2 H) (Example 2) |
| 58 | | 7.72-7.63 (m, 2 H) 7.60 (s, 1 H) 7.47 (s, 1 H) 7.33 (d, J = 6.1 Hz, 1 H) 6.64 (d, J = 2.6 Hz, 1 H) 6.49 (d, J = 1.3 Hz, 1 H) 3.32 (s, 4 H) |
| 59 | | 7.81 (s, 1 H) 7.42-7.37 (m, 2 H) 7.29 (d, J = 2.8 Hz, 1 H) 7.05 (d, J = 2.9 Hz, 1 H) 6.94 (dd, J = 5.0, 1.6 Hz, 1 H) 6.87 (d, J = 9.3 Hz, 1 H) 5.26 (s, 2 H) |

TABLE 2-continued
Compounds Prepared According to Method of Example 2 and Equivalent Methods
| Nos. | Cpd. Structure | $^1$H-NMR (DMSO-$d_6$, 200 MHz) δ |
|---|---|---|
| 60 | 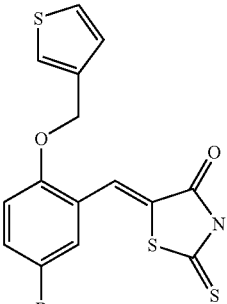 | 7.89 (s, 1 H) 7.45 (d, J = 1.4 Hz, 1 H) 7.41-7.27 (m, 3 H) 7.09 (dd, J = 4.8, 1.4 Hz, 1 H) 6.85 (d, J = 8.5 Hz, 1 H) 5.16 (s, 2 H) |
| 61 | 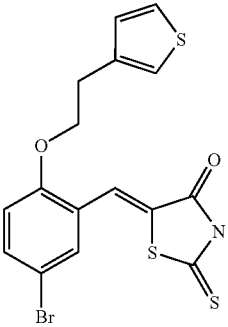 | 7.85 (s, 1 H) 7.43-7.27 (m, 2 H) 7.26-7.23 (m, 1 H) 7.07 (d, J = 1.4 Hz, 1 H) 6.99 (dd, J = 4.8, 1.2 Hz, 1 H) 6.75 (d, J = 9.3 Hz, 1 H) 4.17 (t, J = 6.9 Hz, 1 H) 3.14 (t, J = 6.6 Hz, 1 H) |
| 62 | 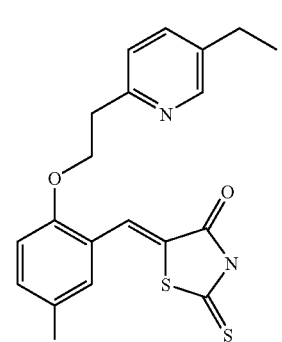 | 8.37 (d, J = 1.7 Hz, 1 H) 7.58 (s, 1 H) 7.55 (d, J = 2.2 Hz, 1 H) 7.47 (s, 1 H) 7.41 (d, J = 2.4 Hz, 1 H) 7.28 (d, J = 7.8 Hz, 1 H) 7.16 (d, J = 8.9 Hz, 1 H) 4.45 (t, J = 6.6 Hz, 2 H) 3.19 (t, J = 6.4 Hz, 2 H) 2.58 (q, J = 15.2, 7.6 Hz, 2 H) 1.16 (t, J = 7.4 Hz, 3 H) |
| 63 | 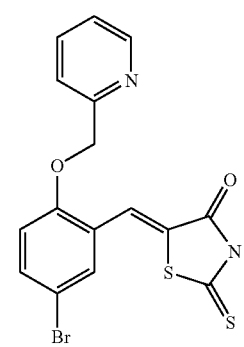 | 8.59 (d, J = 4.7 Hz, 1 H) 7.87-7.82 (m, 1 H) 7.75 (s, 1 H) 7.63 (dd, J = 8.6, 2.2 Hz, 1 H) 7.51-7.48 (m, 2 H) 7.40-7.34 (m, 1 H) 7.18 (d, J = 8.9 Hz, 1 H) 5.35 (s, 2 H) |

TABLE 2-continued

Compounds Prepared According to Method of Example 2 and Equivalent Methods

| Nos. | Cpd. Structure | $^1$H-NMR (DMSO-$d_6$, 200 MHz) δ |
|---|---|---|
| 64 | | 7.61 (s, 1 H), 7.57 (d, J = 2.0 Hz, 1 H), 7.42 (d, J = 2.6 Hz, 1 H), 7.14 (d, J = 9 H, 1 H), 4.27 (t, J = 5.4 Hz, 2 H), 3.65-3.61 (m, 4 H), 2.98 (t, J = 5.4 Hz, 2 H), 2.75-2.70 (m, 4 H) |
| 65 | | 8.49 (d, J = 4 Hz, 1 H), 7.72-7.54 (m, 3 H), 7.38-7.25 (m, 2 H), 7.22-7.15 (m, 2 H), 4.47 (t, J = 6.4 Hz, 2 H), 3.22 (t, J = 6.4 Hz, 2 H) |
| 66 | | 7.63-7.59 (m, 4 H), 7.47-7.35 (m, 3 H), 5.26 (t, J = 6.8 Hz, 2 H), 1.33-1.12 (m, 2 H), 1.21 (t, J = 6.8 Hz, 3 H) |

TABLE 3

Compounds Prepared According to Method of Example 3 and Equivalent Methods

| Nos. | Cpd. Structure | $^1$H-NMR (DMSO-$d_6$, 200 MHz) δ |
|---|---|---|
| 67 | | 7.81 (dd, J = 2.4, 8.8 Hz, 1 H), 7.55 (m, 2 H), 7.46 (m, 1 H), 7.34 (m, 4 H), 6.95 (s, 1 H), 2.32 (s, 3 H) |

TABLE 3-continued

Compounds Prepared According to Method of Example 3 and Equivalent Methods

| Nos. | Cpd. Structure | $^1$H-NMR (DMSO-$d_6$, 200 MHz) δ |
| --- | --- | --- |
| 68 | | 7.82 (dd, J = 8.8, 2.2 Hz, 1 H), 7.67-7.66 (m, 1 H), 7.58-7.51 (m, 2 H), 3.34 (s, 3 H); (Example 3) |
| 69 | | 7.78 (dd, J = 8.8, 2.6 Hz, 1 H), 7.28 (d, J = 8.6 Hz, 1 H), 7.14 (s, 1 H), 7.03 (s, 2 H), 2.35 (s, 6 H), 2.23 (s, 3 H) |
| 70 | | 7.85-7.78 (m, 4 H), 7.65-7.61 (m, 2 H), 7.52 (d, J = 2.0 Hz, 1 H), 7.38 (d, J = 8.8 Hz, 1 H), 6.95 (s, 1 H) |

TABLE 4

Compounds Prepared According to Method of Example 4 and Equivalent Methods

| Nos. | Cpd. Structure | $^1$H-NMR (DMSO-$d_6$, 200 MHz) δ |
| --- | --- | --- |
| 71 | | 7.65-7.61 (m, 3 H), 7.48-7.40 (m, 2 H), 7.26-7.07 (m, 3 H), 6.85-6.80 (m, 1 H) |

TABLE 4-continued
Compounds Prepared According to Method of Example 4 and Equivalent Methods
| Nos. | Cpd. Structure | $^1$H-NMR (DMSO-$d_6$, 200 MHz) δ |
|---|---|---|
| 72 | 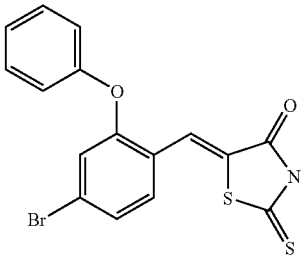 | 7.69 (s, 1 H), 7.50-7.43 (m, 4 H), 7.29-7.25 (m, 1 H), 7.15-7.10 (m, 2 H), 6.98 (s, 1 H) |
| 73 | 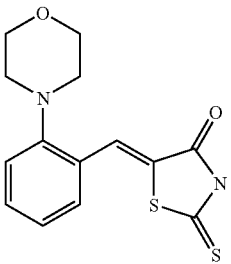 | 8.00 (s, 1 H), 7.48-7.41 (m, 2 H), 7.20-7.10 (m, 2 H), 3.91 (t, J = 4.5 Hz, 4 H), 2.98 (t, J = 4.5 Hz, 4 H) |
| 74 | 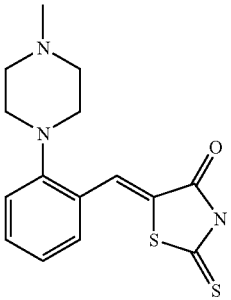 | 7.66 (s, 1 H), 7.51-7.45 (m, 2 H), 7.42-7.25 (m, 2 H), 3.31 (brs, 4 H), 3.21 (brs, 4 H), 2.83 (s, 3 H) |
| 75 | 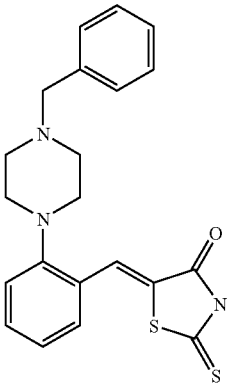 | 7.97 (s, 1 H), 7.45-7.29 (m, 7 H), 7.12 (t, J = 7.8 Hz, 2 H), 3.65 (s, 2 H), 3.05-3.01 (m, 4 H), 2.80-2.70 (m, 4 H) |
| 76 | 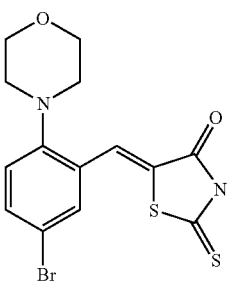 | 7.85 (s, 1 H), 7.54-7.50 (m, 2 H), 7.01-6.96 (m, 1 H), 3.89 (t, J = 4.5 Hz, 4 H), 2.94 (t, J = 4.5 Hz, 4 H) |

TABLE 4-continued

Compounds Prepared According to Method of Example 4 and Equivalent Methods

| Nos. | Cpd. Structure | $^1$H-NMR (DMSO-$d_6$, 200 MHz) δ |
|---|---|---|
| 77 | | 7.83-7.74 (m, 2 H), 7.64-7.52 (m, 2 H), 7.49-7.29 (m, 1 H), 7.25-7.22 (m, 2 H), 6.67 (d, J = 7.8 Hz, 1 H); (Example 4) |
| 78 | | 7.85-7.62 (m, 3 H), 7.42-7.36 (m, 3 H), 7.13-7.08 (m, 1 H), 6.95 (d, J = 8.6 Hz, 1 H) |
| 79 | | 7.67-7.59 (m, 5 H), 7.07 (d, J = 8.6 Hz, 2 H), 6.93 (d, J = 9.8 Hz, 1 H) |
| 80 | | 8.07-8.06 (m, 1 H), 7.70-7.60 (m, 4 H), 7.24 (s, 1 H), 7.20 (d, J = 8.6 Hz, 1 H), 7.78 (d, J = 9.6 Hz, 1 H) |
| 81 | | 7.97 (dd, J = 7.6, 1.8 Hz), 7.77-7.68 (m, 2 H), 7.60 (s, 1 H), 7.44-7.35 (m, 1 H), 7.15-7.03 (m, 2 H) |

TABLE 4-continued

Compounds Prepared According to Method of Example 4 and Equivalent Methods

| Nos. | Cpd. Structure | $^1$H-NMR (DMSO-d$_6$, 200 MHz) δ |
|---|---|---|
| 82 | | 7.59-7.37 (m, 8 H), 7.11 (d, J = 8.5 Hz, 1 H), 3.82 (s, 2 H), 2.96 (brs, 4 H), 2.78 (brs, 4 H) |
| 83 | | 7.59-7.56 (m, 2 H), 7.47 (d, J = 2.1 Hz, 1 H), 7.10 (d, J = 8.4 Hz, 1 H), 2.85 (brs, 4 H), 1.66-1.56 (m, 6 H) |
| 84 | | 7.69 (s, 1 H), 7.51 (d, J = 2.4 Hz, 1 H), 7.43 (dd, J = 8.9 Hz, 2.4 Hz, 1 H), 6.95 (d, J = 8.9 Hz, 1 H), 3.10 (brs, 4 H), 1.87 (brs, 4 H) |
| 85 | | 7.84-7.77 (m, 2 H), 7.56-7.47 (m, 3 H), 7.32-7.25 (m, 2 H), 6.81 (s, 1 H) |
| 86 | | 7.62-7.36 (m, 6 H), 7.16-7.09 (m, 2 H) |

TABLE 4-continued

Compounds Prepared According to Method of Example 4 and Equivalent Methods

| Nos. | Cpd. Structure | $^1$H-NMR (DMSO-$d_6$, 200 MHz) δ |
|---|---|---|
| 87 | | 7.68-7.36 (m, 6 H), 7.11-6.93 (m, 4 H), 6.90 (d, J = 8.6 Hz, 1 H), 6.93 (s, 1 H) |
| 88 | | 7.68 (dd, J = 8.6 Hz, 2.4 Hz, 1 H), 7.51 (2, 2 H), 7.18 (d, J = 8.6 Hz, 2 H), 3.32 (brs, 4 H), 3.19 (brs, 4 H), 2.83 (s, 3 H) |
| 89 | | 7.98 (d, J = 7.8 Hz, 1 H), 7.76-7.52 (m, 4 H), 7.44-7.37 (m, 2 H), 7.13 (d, J = 8.8 Hz, 1 H) |

TABLE 5

Compounds Prepared According to Method of Example 5 and Equivalent Methods

| Nos. | Cpd. Structure | $^1$H-NMR (DMSO-$d_6$, 200 MHz) δ |
|---|---|---|
| 90 | | 7.89 (s, 1 H), 7.78 (d, J = 8.8 Hz, 1 H), 7.65-7.62 (m, 3 H), 7.60-7.30 (m, 1 H), 5.32 (s, 2 H) |

TABLE 5-continued
Compounds Prepared According to Method of Example 5 and Equivalent Methods
| Nos. | Cpd. Structure | $^1$H-NMR (DMSO-$d_6$, 200 MHz) δ |
|---|---|---|
| 91 | 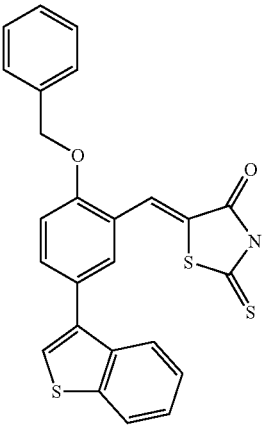 | 8.12-8.07 (m, 1 H), 7.92-7.86 (m, 3 H), 7.75-7.71 (m, 1 H), 7.58-7.38 (m, 10 H), 5.35 (s, 2 H) |
| 92 | 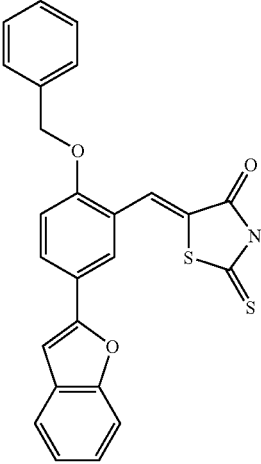 | 7.01 (d, J = 8.8 Hz, 1 H), 7.87-7.38 (m, 1 H), 7.64 (d, J = 6.4 Hz, 2 H), 7.51-7.25 (m, 10 H), 5.34 (s, 2 H) |
| 93 | 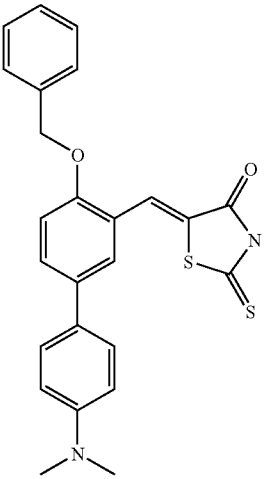 | 7.89 (s, 1 H), 7.68 (d, J = 9.4 Hz, 1 H), 7.51-7.26 (m, 3 H), 6.84 (d, J = 9.4 Hz, 2 H), 5.30 (s, 2 H), 2.94 (s, 6 H); (Example 5) |

TABLE 5-continued

Compounds Prepared According to Method of Example 5 and Equivalent Methods

| Nos. | Cpd. Structure | ¹H-NMR (DMSO-$d_6$, 200 MHz) δ |
|---|---|---|
| 94 | | 7.92-7.72 (m, 2 H), 7.56-7.31 (m, 7 H), 6.84 (d, J = 8.6 Hz, 2 H), 5.34 (s, 2 H), 2.94 (s, 6 H) |
| 95 | | (s, 1 H), 7.70 (d, J = 8.2 Hz, 2 H), 7.62-7.26 (m, 7 H), 6.84 (d, J = 6.8 Hz, 2 H), 5.29 (s, 2 H), 2.93 (s, 6 H) |
| 96 | | 7.83 (s, 1 H), 7.68 (d, J = 8.0 Hz, 1 H), 7.85-7.17 (m, 6 H), 6.96 (d, J = 8.4 Hz, 2 H), 6.83 (d, J = 9.0 Hz, 2 H), 5.20 (s, 2 H), 3.76 (s, 3 H), 2.93 (s, 6 H) |

TABLE 5-continued
Compounds Prepared According to Method of Example 5 and Equivalent Methods
| Nos. | Cpd. Structure | $^1$H-NMR (DMSO-$d_6$, 200 MHz) δ |
|---|---|---|
| 97 | 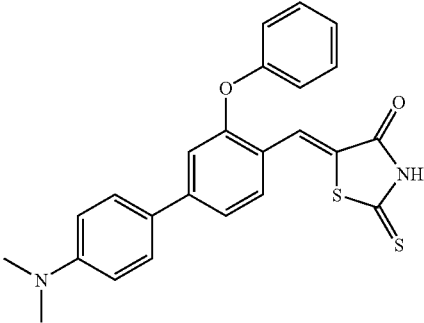 | 7.66-7.36 (m, 7 H), 7.22-7.06 (m, 4 H), 6.14 (d, J = 8.6 Hz, 2 H), 2.97 (s, 6 H) |
| 98 | 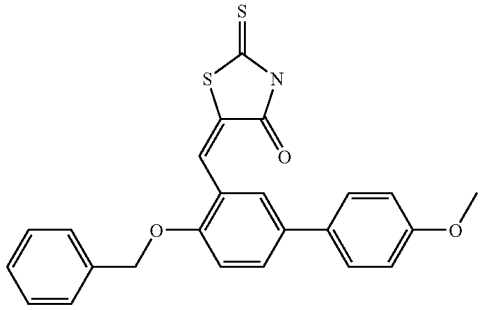 | 7.89 (s, 1 H), 7.73 (dd, J = 2.4, 8.7 Hz, 1 H), 7.60-7.26 (m, 9 H), 7.06 (d, J = 8.4 Hz, 2 H), 5.31 (s, 2 H), 3.80 (s, 3 H) |
| 99 | 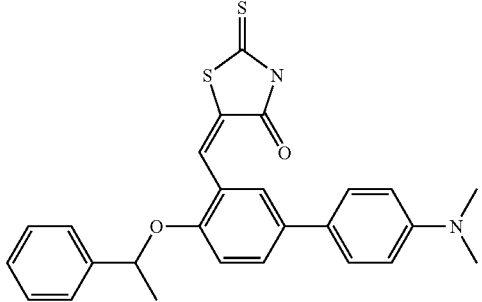 | 7.97 (s, 1 H), 7.55 (d, J = 1.8, 8.4 Hz, 1 H), 7.50-7.20 (m, 8 H), 7.06 (d, J = 8.7 Hz, 1 H), 6.81 (d, J = 9.3 Hz, 2 H), 5.69 (q, J = 6.6 Hz, 1 H), 2.92 (s, 6 H), 1.64 (d, J = 6.0 Hz, 3 H) |
| 100 | 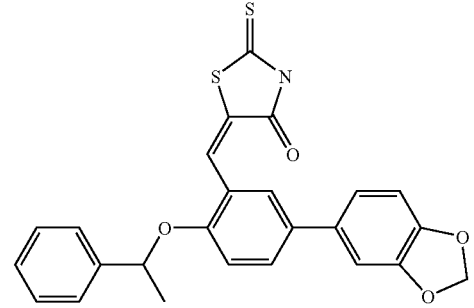 | 13.87 (brs, 1 H), 7.99 (s, 1 H), 7.58 (dd, J = 2.1, 8.4 Hz, 1 H), 7.52-6.98 (m, 10 H), 6.05 (s, 2 H), 5.72 (q, J = 6.9 Hz, 1 H), 1.64 (d, J = 6.6 Hz, 3H) |

TABLE 5-continued

Compounds Prepared According to Method of Example 5 and Equivalent Methods

| Nos. | Cpd. Structure | $^1$H-NMR (DMSO-$d_6$, 200 MHz) δ |
|---|---|---|
| 101 | | 13.81 (brs, 1 H), 7.89 (s, 1 H), 7.69 (dd, J = 1.5, 8.7 Hz, 1 H), 7.56-7.24 (m, 8 H), 6.84 (d, J = 9 Hz, 2 H), 5.30 (s, 2 H), 2.94 (s, 6 H) |
| 102 | | 13.84 (brs, 1 H), 7.87 (s, 1 H), 7.72 (dd, J = 1.8, 8.4 Hz, 1 H), 7.56-6.99 (m, 10 H), 6.07 (s, 2 H), 5.32 (s, 2 H) |
| 103 | | 7.80 (s, 1 H), 7.68 (dd, J = 1.5, 8.7 Hz, 1 H), 7.55-7.40 (m, 3 H), 7.20 (d, J = 8.4 Hz, 1 H), 6.84 (d, J = 9 Hz, 2 H), 5.49 (t, J = 16.2 Hz, 1 H), 4.70 (d, J = 6.6 Hz, 2 H), 2.93 (s, 6 H), 1.76 (d, J = 6.6 Hz, 6 H) |
| 104 | | 8.18 (d, J = 7.2 Hz, 2 H), 7.98 (s, 1 H), 7.65-7.44 (m, 5 H), 7.40 (d, J = 8.7 Hz, 2 H), 6.80 (d, J = 8.4 Hz, 1 H), 6.60 (d, J = 4.0 Hz, 1 H), 2.92 (s, 6 H), 1.74 (s, 6 H) |

TABLE 5-continued

Compounds Prepared According to Method of Example 5 and Equivalent Methods

| Nos. | Cpd. Structure | $^1$H-NMR (DMSO-$d_6$, 200 MHz) δ |
|---|---|---|
| 105 | | 8.17 (d, J = 7.2 Hz, 2 H), 7.97 (s, 1 H), 7.68-7.41 (m, 5 H), 7.14 (d, J = 3, 1 H), 7.10-6.94 (m, 2 H), 6.62 (d, J = 7.8 Hz, 1 H), 6.04 (s, 2 H), 1.75 (s, 6 H) |
| 106 | | 8.05 (s, 1 H), 7.66-7.11 (m, 15 H), 6.82 (d, J = 8.7 Hz, 2 H), 6.74 (s, 1 H), 2.92 (s, 6 H) |
| 107 | | 8.07 (s, 1 H), 7.61 (dd, J = 1.8, 8.4 Hz, 1 H), 7.55-6.97 (m, 15 H), 6.77 (s, 1 H), 6.05 (s, 2 H) |

TABLE 6

Compounds Prepared According to Method of Example 6 and Equivalent Methods

| Nos. | Cpd. Structure | $^1$H-NMR (DMSO-$d_6$, 200 MHz) δ |
|---|---|---|
| 108 | | 7.62-7.59 (m, 3 H), 7.56-7.43 (m, 3 H), 7.40-7011 (m, 2 H), 4.41 (s, 4 H) |

TABLE 6-continued

Compounds Prepared According to Method of Example 6 and Equivalent Methods

| Nos. | Cpd. Structure | $^1$H-NMR (DMSO-$d_6$, 200 MHz) δ |
| --- | --- | --- |
| 109 | | 8.76-8.74 (m, 1 H), 8.24 (d, J = 8.0 Hz, 1 H), 7.94 (d, J = 9.8 Hz, 1 H), 7.69-7.65 (m, 2 H), 7.51-7.44 (m, 4 H), 7.29-7.25 (m, 1 H), 4.55-4.53 (m, 4 H) |
| 110 | | 8.19 (s, 1 H), 7.68-7.64 (m, 2 H), 7.47 (s, 1 H), 7.39-7.35 (m, 1 H), 7.25-7.16 (m, 2 H), 4.46 (s, 2 H), 4.42 (s, 2 H), 2.37 (s, 3 H) |
| 111 | | 8.24 (s, 1 H), 7.87 (d, J = 6.4 hz, 1 H), 7.68-7.64 (m, 2 H), 7.48 (s, 1 H), 7.36-7.32 (m, 2 H), 7.21-7.06 (m, 1 H), 4.46 (s, 4 H) |
| 112 | | 8.24 (s, 1 H), 7.87 (d, 1 = 6.4 hz, 1 H), 7.68-7.64 (m, 2 H), 7.48 (s, 1 H), 7.36-7.32 (m, 2 H), 7.21-7.06 (m, 1 H), 4.46 (s, 4 H) |
| 113 | | 7.84 (dd, J = 8.9, 2.4 Hz, 1 H) 7.73 (d, J = 2.6 Hz, 1 H) 7.57 (dd, J = 7.8, 1.7 Hz, 1 H) 7.40-7.32 (m, 3 H) 7.21 (dd, J = 8.3, 1.5 Hz, 1 H) 6.91 (dt, J = 7.8, 1.5 Hz, 1 H) 4.59-4.53 (m, 2 H), 4.50-5.27 (m, 2 H) |

TABLE 6-continued
Compounds Prepared According to Method of Example 6 and Equivalent Methods
| Nos. | Cpd. Structure | ¹H-NMR (DMSO-d$_6$, 200 MHz) δ |
|---|---|---|
| 114 | 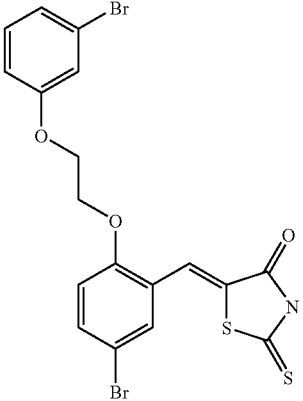 | 7.70-7.64 (m, 2 H) 7.49 (d, J = 2.0 Hz, 1 H) 7.29-7.21 (m, 3 H) 7.14 (d, J = 7.6 Hz, 1 H) 7.01 (dd, J = 8.1, 1.5 Hz, 1 H) 4.46 (m, 2 H) 4.41 (m, 2 H); (Example 6) |
| 115 | 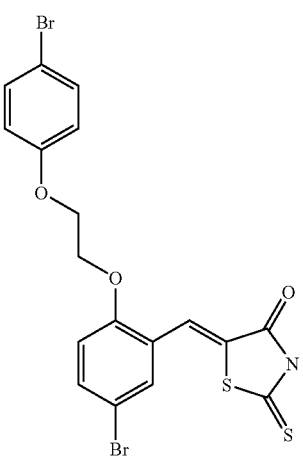 | 7.68-7.64 (m, 2 H) 7.47-7.36 (m, 3 H) 7.23 (d, J = 9.1 Hz, 1 H) 6.97 (dd, J = 9.1, 2.2 Hz, 2 H) 4.45 (m, 2 H) 4.38 (m, 2 H) |
| 116 | 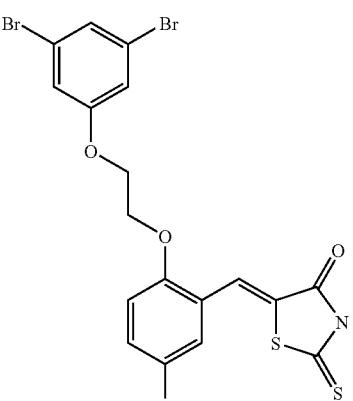 | 7.77 (s, 1 H) 7.64-7.60 (m, 2 H) 7.54 (d, J = 8.1 Hz, 1 H) 7.46 (s, 1 H) 7.25-7.17 (m, 2 H) 4.47 (m, 4 H) |

TABLE 6-continued

Compounds Prepared According to Method of Example 6 and Equivalent Methods

| Nos. | Cpd. Structure | $^1$H-NMR (DMSO-$d_6$, 200 MHz) δ |
| --- | --- | --- |
| 117 | | 7.73-7.63 (m, 4 H) 7.48 (d, J = 2.4 Hz, 1 H) 7.49-7.25 (m, 2 H) 7.10 (t, J = 7.4 Hz, 1 H) 4.57-4.53 (m, 4 H) |
| 118 | | 7.77 (d, J = 9.1 Hz, 2 H) 7.67-7.65 (m, 2 H) 7.47 (s, 1 H) 7.24 (d, J = 9.1 Hz, 1 H) 7.17 (d, J = 8.9 Hz, 2 H) 4.49 (s, 4 H) |
| 119 | | 7.71-7.65 (m, 2 H) 7.48 (s, 1 H) 7.41 (d, J = 7.6 Hz, 1 H) 7.36-7.25 (m, 3 H) 6.97 (t, J = 7.9 Hz, 1 H) 4.51-4.47 (m, 4 H) |

TABLE 6-continued
Compounds Prepared According to Method of Example 6 and Equivalent Methods
| Nos. | Cpd. Structure | $^1$H-NMR (DMSO-$d_6$, 200 MHz) δ |
|---|---|---|
| 120 | 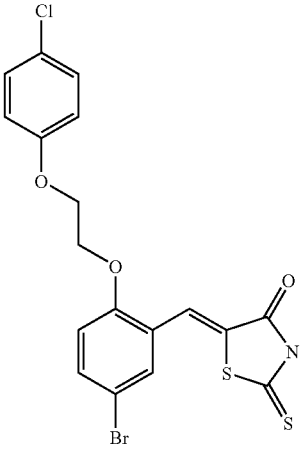 | 7.65-7.55 (m, 3 H) 7.47 (d, J = 2.2 Hz, 1 H) 7.23 (d, J = 8.9 Hz, 1 H) 6.85 (d, J = 8.7 Hz, 2 H) 4.51-4.47 (m, 4 H) |
| 121 | 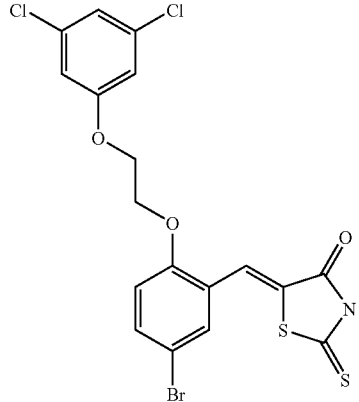 | 7.64-7.62 (m, 2 H) 7.55 (d, J = 2.2 Hz, 1 H) 7.47 (d, J = 2.2 Hz, 1 H) 7.36 (d, J = 2.4 Hz, 1 H) 7.29-7.22 (m, 2 H) 4.51-4.47 (m, 4 H) |
| 122 | 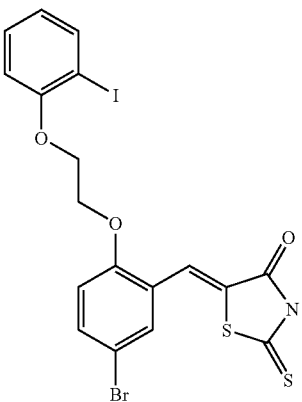 | 7.78-7.74 (m, 2 H), 7.68 (dd, J = 9.0, 2.3 Hz, 1 H), 7.49 (d, J = 2.1 Hz, 1 H), 7.40-7.27 (m, 2 H), 7.10 (d, J = 8.0 Hz, 1 H), 6.78 (m, 1 H), 4.50-4.43 (m, 4 H) |

TABLE 6-continued

Compounds Prepared According to Method of Example 6 and Equivalent Methods

| Nos. | Cpd. Structure | $^1$H-NMR (DMSO-$d_6$, 200 MHz) δ |
|---|---|---|
| 123 | | 7.69 (s, 1 H) 7.65-7.55 (m, 3 H) 7.47 (d, J = 2.2 Hz, 1 H) 7.23 (d, J = 8.9 Hz, 1 H) 6.85 (d, J = 8.7 Hz, 2 H) 4.47-4.44 (m, 2 H) 4.36-4.34 (m, 2 H) |
| 124 | | 7.69-7.64 (m, 2 H) 7.48 (d, J = 2.4 Hz, 1 H) 7.36-7.33 (m, 2 H) 7.24 (d, J = 9.1 Hz, 1 H) 4.47-4.45 (m, 2 H) 4.39-4.36 (m, 2 H) |
| 125 | | 7.69-7.63 (m, 2 H), 7.47 (d, J = 2.3 Hz, 1 H), 7.34-7.22 (m, 3 H), 7.02-6.91 (m, 3 H), 4.48 (m, 2 H), 4.36 (m, 2 H) |

TABLE 6-continued

Compounds Prepared According to Method of Example 6 and Equivalent Methods

| Nos. | Cpd. Structure | $^1$H-NMR (DMSO-$d_6$, 200 MHz) δ |
|---|---|---|
| 126 | | 8.34 (d, J = 2.8 Hz, 1 H) 8.18 (d, J = 4.3 Hz, 1 H) 7.69-7.65 (m, 2 H) 7.49-7.44 (m, 2 H) 7.36 (d, J = 4.5 Hz, 1 H) 7.25 (d, J = 8.9 Hz, 1 H) 4.55-4.45 (m, 4 H) |
| 127 | | 8.45 (dd, J = 4.9, 1.5 Hz, 2 H) 7.68-7.59 (m, 2 H) 7.48 (d, J = 1.9 Hz, 1 H) 7.23 (d, J = 8.9 Hz, 1 H) 7.12 (dd, J = 4.9, 1.5 Hz, 2 H) 4.51 (m, 4 H) |
| 128 | | 8.82 (dd, J = 4.1, 1.5 Hz, 1 H) 8.28 (d, J = 6.8 Hz, 1 H) 7.89 (d, J = 8.9 Hz, 1 H) 7.68-7.63 (m, 2 H) 7.48-7.45 (m, 2 H) 7.41-7.37 (m, 1 H) 7.35-7.28 (m, 1 H) 7.28 (d, J = 8.5 Hz, 1 H) 4.56 (s, 4 H) |

TABLE 6-continued
Compounds Prepared According to Method of Example 6 and Equivalent Methods
| Nos. | Cpd. Structure | $^1$H-NMR (DMSO-$d_6$, 200 MHz) δ |
|---|---|---|
| 129 | 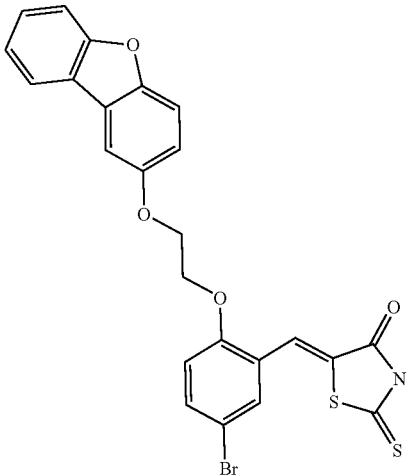 | 8.10 (d, J = 6.4 Hz, 1 H) 7.79 (d, J = 2.4 Hz, 1 H) 7.72-7.58 (m, 4 H) 7.54-7.47 (m, 2 H) 7.39 (d, J = 7.4 Hz, 1 H) 7.29 (d, J = 9.1 Hz, 1 H) 7.16 (dd, J = 8.9, 2.6 Hz, 1 H) 4.53-4.47 (m, 4 H) |
| 130 | 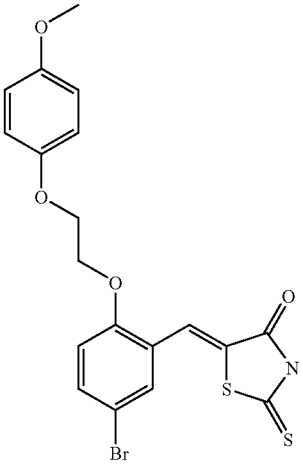 | 7.71-7.63 (m, 2 H), 7.47-7.45 (m, 1 H), 7.25-7.21 (m, 1 H), 6.95-6.82 (m, 4 H), 4.43 (brs, 2 H), 4.30 (brs, 2 H), 3,69 (s, 3 H) |
| 131 | 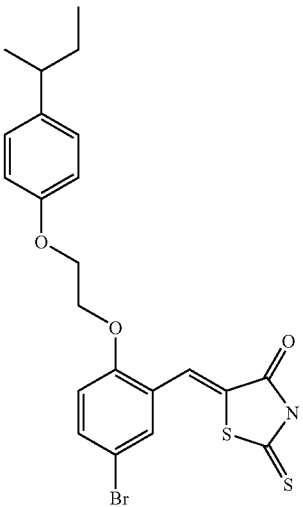 | 7.72 (s, 1), 7.66 (dd, J = 9.0, 2.2 Hz, 1 H), 7.47 (d, J = 2.4 Hz, 1 H), 7.27-7.22 (m, 1 H), 7.08 (d, J = 8.6 Hz, 2 H), 6.88 (d, J = 8.6 Hz, 2 H), 4.47 (brs, 2 H), 4.32 (brs, 2 H), 2.57-2.49 (m, 1 H), 1.47 (quin, J = 7.6 Hz, 2 H), 1.14 (d, J = 7.0 Hz, 3 H), 0.74 (t, J = 7.4 Hz, 3 H) |

TABLE 6-continued

Compounds Prepared According to Method of Example 6 and Equivalent Methods

| Nos. | Cpd. Structure | $^1$H-NMR (DMSO-$d_6$, 200 MHz) δ |
|---|---|---|
| 132 | | 7.81 (s, 1 H), 7.66 (dd, J = 8.6, 1.8 Hz, 1 H), 7.46 (d, J = 2.0 Hz, 1 H), 7.13 (d, J = 9.0 Hz, 1 H), 7.02-6.87 (m, 3 H), 4.42 (brs, 2 H), 4.13 (brs, 2 H), 2.38 (s, 6 H) |
| 133 | | 7.72 (s, 1 H), 7.54 (dd, J = 8.8, 2.2 Hz, 1 H), 7.36-7.26 (m, 3 H), 6.95-6.82 (m, 3 H, 4.45-4.43 (m, 2 H), 3.69 (s, 3 H) |
| 134 | | 7.74 (s, 1 H), 7.54 (dd, J = 8.6, 2.4 Hz, 1 H), 7.34-7.23 (m, 2 H), 7.00-6.84 (m, 3 H), 4.36 (t, J = 5.6 Hz, 2 H), 3.89 (t, J = 5.6 Hz, 2 H), 7.28-7.17 (m, 8 H) |
| 135 | | δ 8.30 (s, 1 H), 7.82-7.43 (m, 6 H), 7.24 (d, J = 1.3 Hz, 1 H), 7.06 (d, J = 8.8 Hz, 1 H), 4.25 (t, J = 6.5 Hz, 2 H), 4.08 (t, J = 5.9 Hz, 2 H) |

TABLE 6-continued
Compounds Prepared According to Method of Example 6 and Equivalent Methods
| Nos. | Cpd. Structure | $^1$H-NMR (DMSO-$d_6$, 200 MHz) δ |
|---|---|---|
| 136 | 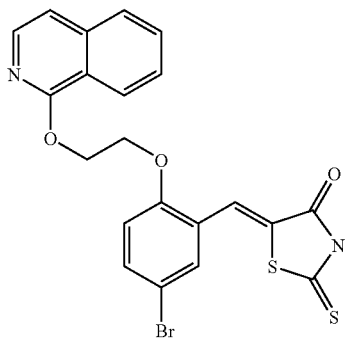 | δ 8.21 (s, 1 H), 7.67-7.23 (m, 6 H), 7.24 (d, J = 1.3 Hz, 1 H), 7.06 (d, J = 8.8 Hz, 1 H), 4.25 (t, J = 6.5 Hz, 2 H), 4.08 (t, J = 5.9 Hz, 2 H) |
| 137 | 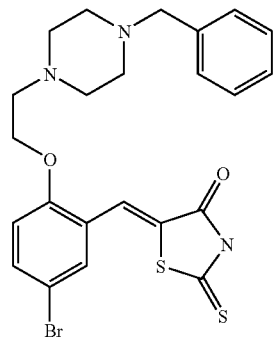 | 7.62-7.05 (m, 9 H), 4.19-4.17 (m, 2 H), 3.64 (s, 2 H), 2.94-2.86 (m, 2 H), 2.62-2.57 (m, 8 H) |
| 138 | 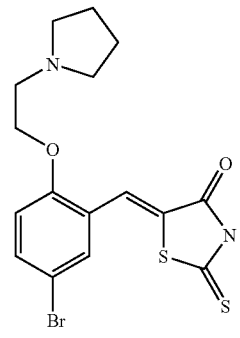 | 7.69-7.39 (m, 2 H), 7.10-7.01 (m, 2 H), 4.22-4.19 (m, 2 H), 2.90-2.88 (m, 2 H), 2.64-2.60 (m, 4 H), 1.55-1.51 (m, 4 H) |
| 139 | 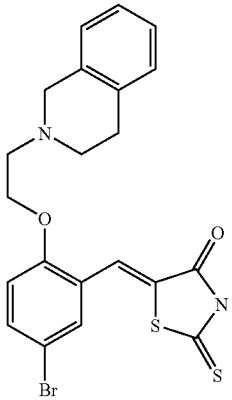 | 7.51-7.44 (m, 9 H), 7.14-7.11 (m, 5 H), 4.33-4.31 (m, 2 H), 3.90 (s, 2 H), 3.11-3.09 (m, 2 H), 2.99-2.97 (m, 2 H), 2.91-2.89 (m, 2 H) |

TABLE 6-continued
Compounds Prepared According to Method of Example 6 and Equivalent Methods
| Nos. | Cpd. Structure | $^{1}$H-NMR (DMSO-$d_6$, 200 MHz) δ |
|---|---|---|
| 140 | 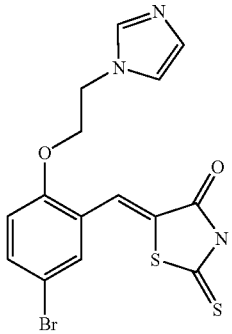 | $^{1}$H NMR (200 MHz, DMSO-$d_6$) δ 8.33 (s, 1 H), 7.57-7.43 (m, 3 H), 7.24 (d, J = 1.3 Hz, 1 H), 7.06 (d, J = 8.8 Hz, 1 H), 4.25 (t, J = 6.5 Hz, 2 H), 4.08 (t, J = 5.9 Hz, 2 H) |
| 141 | 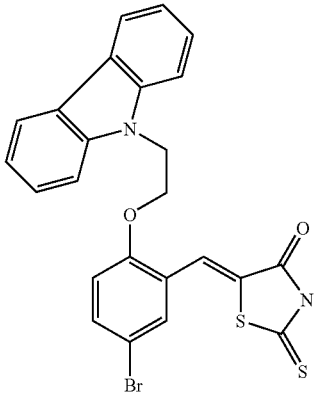 | 8.12 (s, 1 H), 8.09 (s, 1 H), 7.69 (s, 1 H), 7.64 (s, 2 H), 7.54-7.42 (m, 3 H), 7.32 (s, 1 H), 7.21-7.14 (m, 2 H), 7.05 (d, J = 9.0 Hz, 1 H), 4.85 (brs, 2 H), 4.47 (brs, 2 H) |
| 142 | 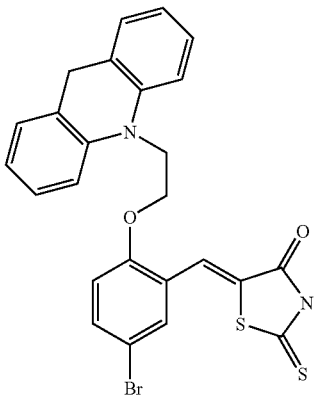 | $^{1}$H NMR (200 MHz, DMSO-$d_6$) δ 7.45-7.42 (m, 3 H), 7.11-7.06 (m, 1 H), 6.89-6.87 (m, 4 H), 6.65-6,63 (m, 4 H), 4.29-4.27 (m, 2 H), 4.09-4.07 (m, 2 H) |
| 143 | 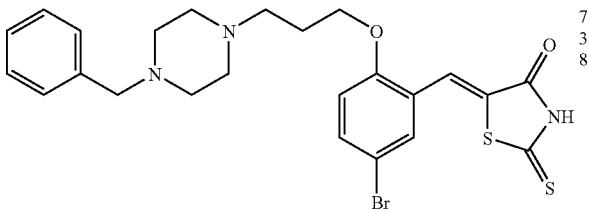 | 7.52-7.33 (m, 9 H), 7.09-7.02 (m, 1 H), 4.12-4.10 (m, 2 H), 3.66 (s, 2 H), 2.87-2.83 (m, 8 H), 2.65-2.61 (m, 2 H), 2.08-1.99 (m, 2 H) |

TABLE 6-continued

Compounds Prepared According to Method of Example 6 and Equivalent Methods

| Nos. | Cpd. Structure | $^1$H-NMR (DMSO-$d_6$, 200 MHz) δ |
|---|---|---|
| 144 | | 7.58-7.39 (m, 2 H), 7.02-6.94 (m, 2 H), 4.11-4.09 (m, 2 H), 2.84-2.69 (m, 6 H), 2.09-2.04 (m, 2 H), 1.62-1.47 (m, 4 H) |
| 145 | | $^1$H NMR (200 MHz, DMSO-$d_6$) δ 8.14 (s, 1 H), 8.10 (s, 1 H), 7.82 (s, 1 H), 7.58-7.54 (m, 3 H), 7.44-7.36 (m, 3 H), 7.21-7.13 (m, 2 H), 6.99 (d, J = 9.0 Hz, 1 H), 4.58-4.51 (m, 2 H), 4.12-4.09 (m, 2 H), 2.29-2.26 (m, 2 H) |
| 146 | | 8.33 (s, 1 H), 7.57-7.43 (m, 3 H), 7.24 (d, J = 1.3 Hz, 1 H), 7.06 (d, J = 8.8 Hz, 1 H), 4.25 (t, J = 6.5 Hz, 2 H), 4.08 (t, J = 5.9 Hz, 2 H), 2.33-2.27 (m, 2 H) |

TABLE 7

Compounds Prepared According to Method of Example 7 and Equivalent Methods

| Nos. | Cpd. Structure | $^1$H-NMR (DMSO-$d_6$, 200 MHz) δ |
|---|---|---|
| 147 | | 7.77-7.31 (m, 6 H), 6.85-6.83 (m, 2 H), 5.26 (s, 2 H), 4.43 (t, J = 5.4 Hz, 2 H), 3.81 (t, J = 5.4 Hz, 2 H) |
| 148 | | 7.77-7.71 (m, 3 H), 7.63-7.59 (m, 2 H), 7.46-7.42 (m, 6 H), 6.83-6.76 (m, 2 H), 5.27 (s, 2 H), 4.30 (brs, 2 H), 3.33 (s, 2 H), 3.90 (brs, 2 H), 3.07-2.87 (m, 8 H) |

TABLE 7-continued
Compounds Prepared According to Method of Example 7 and Equivalent Methods
| Nos. | Cpd. Structure | $^1$H-NMR (DMSO-$d_6$, 200 MHz) δ |
|---|---|---|
| 149 | 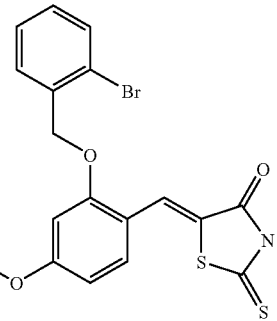 | 7.74-7.70 (m, 2 H), 7.61-7.58 (m, 1 H), 7.49-7.31 (m, 3 H), 6.82-6.75 (m, 2 H), 5.26 (s, 2 H), 4.22 (t, J = 5.9 Hz, 2 H), 3.61 (t, J = 4.6 Hz, 4 H), 2.81 (t, J = 5.9 Hz, 2 H), 2.49 (t, J = 4.6 Hz, 4 H); (Example 7) |
| 150 | 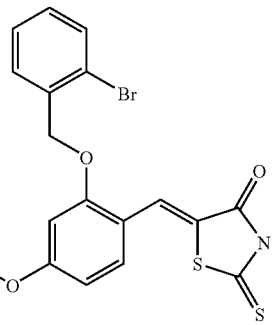 | 7.75-7.71 (m, 1 H), 7.63-7.59 (m, 2 H), 7.47-7.35 (m, 3 H), 6.81-6.78 (m, 2 H), 5.26 (s, 2 H), 4.39 (brs, 2 H), 3.33 (brs, 2 H), 3.33-3.12 (m, 2 H), 1.21 (t, J = 6.8 Hz, 3 H) |
| 151 | 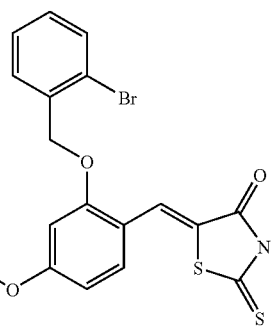 | 7.74-7.71 (m, 2 H), 7.62-7.31 (m, 4 H), 6.78-6.74 (m, 2 H), 5.24 (s, 2 H), 4.34-4.30 (m, 2 H), 3.37-3.34 (m, 2 H), 3.02-2.99 (m, 4 H), 1.70-1.66 (m, 4 H), 1.52-1.48 (m, 2 H) |
| 152 | 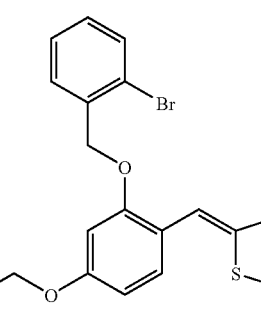 | 7.71-7.69 (m, 2 H), 7.59-7.57 (m, 1 H), 7.45-7.33 (m, 4 H), 7.16-7.13 (m, 4 H), 6.84-6.78 (m, 2 H), 5.26 (s, 2 H), 4.36-4.34 (m, 2 H), 3.92 (s, 2 H), 3.34-2.80 (m, 6 H) |

TABLE 7-continued

Compounds Prepared According to Method of Example 7 and Equivalent Methods

| Nos. | Cpd. Structure | ¹H-NMR (DMSO-d$_6$, 200 MHz) δ |
|---|---|---|
| 153 | | 7.70-7.68 (m, 2 H), 7.55-7.47 (m, 2 H), 7.43-7.29 (m, 4 H), 6.83-6.66 (m, 8 H), 5.21 (s, 2 H), 4.05-4.03 (m, 2 H) |
| 154 | | 7.75-7.69 (m, 2 H), 7.58-7.52 (m, 3 H), 7.47-7.28 (m, 4 H), 7.15 (t, J = 7.5 Hz, 1 H), 7.02 (t, J = 7.3 Hz, 1 H), 6.73-6.69 (m, 2 H), 6.45 (d, J = 3.2 Hz, 1 H), 5.19 (s, 2 H), 4.60-4.58 (m, 2 H), 4.14-4.42 (m, 2 H) |
| 155 | | 7.78-7.70 (m, 2 H), 7.62-7.59 (m, 2 H), 7.50-7.28 (m, 4 H), 6.94 (d, J = 1.1 Hz, 1 H), 6.77-6.71 (m, 2 H), 5.23 (s, 2 H), 4.37 (brs, 2 H) |
| 156 | | 8.16 (s, 1 H), 7.70-7.67 (m, 4 H), 7.59-7.16 (m, 8 H), 6.63-6.58 (m, 2 H), 5.12 (s, 2 H), 4.82 (brs, 2 H), 4.46 (brs, 2 H) |

TABLE 8

Compounds Prepared According to Method of Example 8 and Equivalent Methods

| Nos. | Cpd. Structure | $^1$H-NMR (DMSO-$d_6$, 200 MHz) δ |
|---|---|---|
| 157 | | 7.69 (s, 1 H) 7.64 (dd, J = 8.7, 2.4 Hz, 1 H) 7.46 (s, 1 H) 7.18 (d, J = 8.7 Hz, 1 H) 4.25 (m, 2 H) 3.57 (m, 2 H) 2.88 (s, 3 H) 2.50 (d, J = 1.7 Hz, 9 H) |
| 158 | | 8.72 (brs, 2 H) 7.81 (s, 1 H) 7.68 (dd, J = 8.9, 2.4 Hz, 1 H) 7.50 (d, J = 2.4 Hz, 1 H) 7.18 (d, J = 9.1 Hz, 1 H) 4.37 (t, J = 4.1 Hz, 2 H) 3.41 (m, 2 H) 2.51 (s, 3 H) |
| 159 | | 7.79 (s, 1 H) 7.34-7.29 (m, 3 H) 7.19-7.11 (m, 2 H) 6.99 (s, 1 H) 6.93-6.86 (m, 1 H) 6.78 (d, J = 9.5 Hz, 1 H), 4.15 (t, J = 5.0 Hz, 2 H) 3.72 (t, J = 5.1 Hz, 2 H) 3.14 (s, 3 H) |
| 160 | | 8.13 (s, 1 H, NH) 7.67 (s, 1 H) 7.59 (dd, J = 8.9, 2.4 Hz, 1 H) 7.43 (d, J = 2.4 Hz, 1 H) 7.32 (d, J = 8.7 Hz, 2 H) 7.16 (d, J = 8.9 Hz, 1 H) 6.79 (8.9 Hz, 2 H) 4.24 (t, J = 5.5 Hz, 2 H) 3.72 (t, J = 5.5 Hz, 2 H) 3.69 (s, 3 H, OCH$_3$) 3.07 (s, 3 H, N—CH$_3$) |

TABLE 8-continued
Compounds Prepared According to Method of Example 8 and Equivalent Methods
| Nos. | Cpd. Structure | $^1$H-NMR (DMSO-$d_6$, 200 MHz) δ |
|---|---|---|
| 161 | 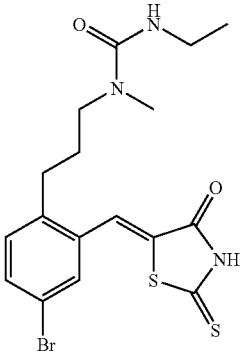 | 7.71 (s, 1 H) 7.62 (dd, J = 8.9, 2.4 Hz, 2 H) 7.43 (d, J = 2.2 Hz, 1 H) 7.16 (d, J = 8.9 Hz, 1 H) 6.28 (t, J = 4.9 Hz, 1 H, NH) 4.17 (t, J = 5.5 Hz, 2 H) 3.60 (t, J = 5.5 Hz, 2 H) 3.03 (q, J = 19.4, 13.8, 6.8 Hz, 2 H) 2.89 (s, 3 H, N—CH$_3$) 0.98 (t, J = 7.2 Hz, 3 H); (Example 8) |
| 162 | 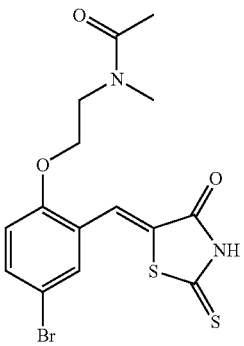 | 7.70-7.61 (m, 2 H) 7.41 (m, 1 H) 7.17 (d, J = 8.9 Hz, 1 H) 4.23 (q, J = 15.4, 9.8, 4.9 Hz, 2 H) 3.76 (t, J = 5.5 Hz, 1 H) 3.67 (t, J = 5.5 Hz, 1 H) 3.07 (s, 3 H) 2.00 (s, 3 H) |
| 163 | 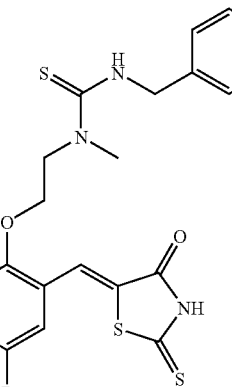 | 8.04 (t, J = 5.1 Hz, 1 H, NH) 7.73 (s, 1 H) 7.62 (dd, J = 8.9, 2.4 Hz, 1 H) 7.45 (d, J = 2.3 Hz, 1 H) 7.36 (s, 1 H) 7.28-7.17 (m, 5 H) 4.78 (d, J = 5.7 Hz, 2 H) 4.36 (m, 2 H) 4.22 (m, 2 H) 3.22 (s, 3 H, N—CH$_3$) |
| 164 | 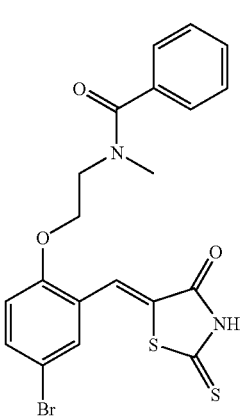 | 7.71-7.63 (m, 1 H) 7.46 (d, J = 2.2 Hz, 1 H) 7.40-7.36 (m, 5 H) 7.26 (brs, 1 H) 7.07 (brs, 1 H) 4.39 (brs, 2 H) 4.27 (brs, 1 H) 3.86 (brs, 1 H) 3.66 (brs, 1 H) 3.01 (s, 3 H) |

TABLE 8-continued
Compounds Prepared According to Method of Example 8 and Equivalent Methods
| Nos. | Cpd. Structure | $^1$H-NMR (DMSO-d$_6$, 200 MHz) δ |
|---|---|---|
| 165 | 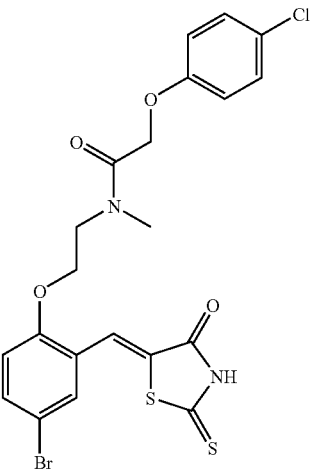 | 7.67-7.64 (m, 3 H) 7.44 (d, J = 2.2 Hz, 1 H) 7.24-7.18 (m, 4 H) 6.87 (d, J = 9.1 Hz, 1 H) 4.84 (s, 2 H) 4.21 (m, 2 H) 3.71 (m, 2 H) 3.13 (s, 3 H) |
| 166 | 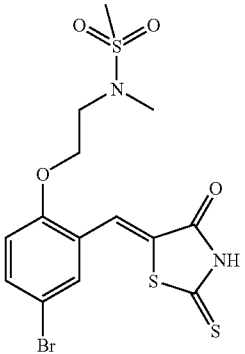 | 7.73 (s, 1 H) 7.66 (dd, J = 8.9, 2.2 Hz, 1 H) 7.46 (d, J = 2.4 Hz, 1 H) 7.36 (s, 1 H) 7.19 (d, J = 9.1 Hz, 1 H) 4.27 (t, J = 5.5 Hz, 2 H) 3.52 (t, J = 5.5 Hz, 2 H), 2.92 (s, 3 H) 2.89 (s, 3 H) |
| 167 | 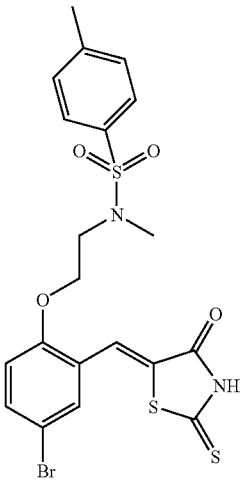 | 7.67-7.61 (m, 4 H) 7.43 (d, J = 2.4 Hz, 1 H) 7.38 (d, J = 7.6 Hz, 2 H) 7.14 (d, J = 8.9 Hz, 1 H) 4.26 (t, J = 5.3 Hz, 2 H) 3.62 (t, J = 5.3 Hz 2 H) 3.32 (s, 3 H) 2.37 (s, 3 H) |

TABLE 9

Compounds Prepared According to Method of Example 9 and Equivalent Methods

| Nos. | Cpd. Structure | $^1$H-NMR (DMSO-$d_6$, 200 MHz) δ |
|---|---|---|
| 168 | | 8.38 (t, J = 5.0 Hz, 1 H), 7.67-7.158 (m, 2 H), 7.59 (d, J = 7.7 Hz, 1 H), 7.46 (m, 1 H), 7.36-7.30 (m, 3 H), 6.97 (d, J = 9.0 Hz, 2 H), 6.82-6.75 (m, 2 H). 5.27 (s, 2 H), 4.52 (s, 2 H), 4.15 (t, J = 5.4 Hz, 2 H), 3.54 (m, 2 H) |
| 169 | | 8.72 (m, 1 H) 7.88-7.84 (m, 2 H) 7.78 (s, 1 H) 7.71 (d, J = 8.8 Hz, 1 H) 7.61-7.32 (m, 7 H) 6.86-6.78 (m, 2 H) 5.26 (s, 2 H) 4.24 (t, J = 5.3 Hz, 2 H) 3.68 (t, J = 5.3 Hz, 2 H); (Example 9) |
| 170 | | 8.58 (s, 1 H), 7.79 (s, 1 H), 7.72 (d, J = 7.8 Hz, 1 H), 7.59 (d, J = 7.4 Hz, 1 H), 7.48-7.33 (m, 5 H), 7.25-7.17 (m, 2 H), 6.92-6.82 (m, 3 H), 6.39 (t, J = 5.5 Hz, 1 H), 5.28 (s, 2 H), 4.15 (t, J = 4.9 Hz, 2 H), 3.45 (t, J = 5.5 Hz, 2 H) |
| 171 | | 8.00 (brs, 1 H), 7.79 (s, 1 H), 7.72 (dd, J = 7.6, 1.1 Hz, 2 H), 7.59 (dd, J = 7.4, 1.7 Hz, 1 H), 7.49-7.41 (m, 2 H), 7.39-7.22 (m, 6 H), 6.85-6.74 (m, 2 H), 5.27 (s, 2 H), 4.67 (s, 2 H), 4.22 (m, 2 H), 3.84 (m, 2 H) |

TABLE 9-continued

Compounds Prepared According to Method of Example 9 and Equivalent Methods

| Nos. | Cpd. Structure | $^1$H-NMR (DMSO-$d_6$, 200 MHz) δ |
|---|---|---|
| 172 | 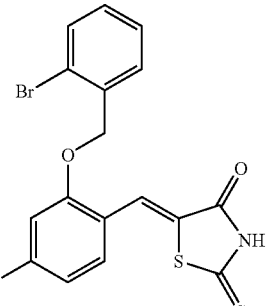 | 8.13 (m, 1 H), 7.77 (s, 1 H), 7.73 (dd, J = 7.8, 1.4 Hz, 1 H), 7.61 (d, J = 7.4 Hz, 1 H), 7.50-7.33 (m, 2 H), 6.83-6.74 (m, 2 H), 5.27 (s, 2 H), 4.10 (t, J = 6.2 Hz, 2 H), 3.42 (t, J = 5.5 Hz, 2 H), 2.51 (s, 3 H) |
| 173 | 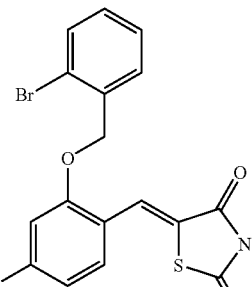 | 7.80 (s, 1 H), 7.73 (d, J = 7.6 Hz, 1 H), 7.60 (d, J = 7.1 Hz, 1 H), 7.47 (m, 1 H), 7.39-7.34 (m, 2 H), 6.83-6.77 (m, 2 H), 5.29 (s, 2 H), 4.15 (t, J = 5.5 Hz, 2 H), 3.33 (m, 2 H), 2.96 (s, 3 H) |
| 174 | 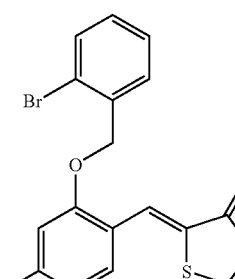 | 7.77 (s, 1 H), 7.73 (dd, J = 7.8, 1.4 Hz, 1 H), 7.61 (d, J = 7.4 Hz, 1 H), 7.50-7.33 (m, 6 H), 6.83-6.74 (m, 2 H), 5.27 (s, 2 H), 4.10 (t, J = 6.2 Hz, 2 H), 3.42 (t, J = 5.5 Hz, 2 H) |

Experimental Example

Assay of the Rhodanine Derivatives for Inhibitory Activity Against Protein Phosphatase In order to examine the ability of the rhodanine derivatives, that is, Compounds 1~174, to inhibit protein phosphatases, they were assayed for IC50 values through the following experiments.

For the experiments, FDP (fluorescein diphosphate) was used as a substrate for genetically recombinant enzymes to measure the fluorescence of FMP (fluorescein monophosphate). The results are given in Table 10, below. In Table 10, IC50 values represent the % concentrations of the rhodanine derivatives of Examples 1, 2, 4, 18, 19, 32, 141, 142, and 157, which are required for 50% inhibition of 20 μM of each of the protein phosphatases (PTP1B, Yop, VHR, PP1, CD45, LAR, Cdc25A, Cdc25B, Cdc25C, pp2A and Prl-3).

TABLE 10

| | IC$_{50}$ | | | | | | | | | | |
|---|---|---|---|---|---|---|---|---|---|---|---|
| Ex. No. | PTP1B | Yop | VHR | PPI | CD45 | LAR | Cdc25A | Cdc25B | Cdc25C | pp2A | Prl-3 |
| 1 | >>20 | | | | | | | | | | 2.98 |
| 2 | >>20 | | >>20 | | | | | | >>20 | | 1.03 |
| 4 | 10 | | >>20 | | | | | | | >>20 | |
| 18 | 2.1 | | | | >>20 | | | | | | |
| 19 | 5.0 | | >>20 | >>20 | | | | | >>20 | | |
| 32 | >>20 | | >>20 | | >>20 | | | | >>20 | | 1.34 |
| 141 | 47 | | | | | >>20 | 2.7 | | | | 1.6 |

TABLE 10-continued

| | | | | | | IC$_{50}$ | | | | | |
|---|---|---|---|---|---|---|---|---|---|---|---|
| Ex. No. | PTP1B | Yop | VHR | PPI | CD45 | LAR | Cdc25A | Cdc25B | Cdc25C | pp2A | Prl-3 |
| 142 | 13 | | | | | | 4.4 | | >>20 | | 3.6 |
| 157 | >>20 | >>20 | | | >>20 | | | | | | 6.2 |

As are apparent from data of Table 10, the rhodanine derivatives according to the present invention have potent inhibitory activity against protein phosphatase.

Preparation Example

1. Preparation of Syrup

A hydrochloric acid salt of 5-(4-benzyloxy-4'-dimethylamino-biphenyl-3-ylmethylene)-2-thioxo-thiazolidin-4-one was prepared from the rhodanine derivative synthesized in Example 5 using a typical process. 2 g of the hydrochloric acid salt, 25.4 g of glucose, and 0.4 g of saccharin were dissolved in 80 g of warm water, followed by cooling the solution. To this solution were added 8.0 g of glycerin, 0.4 g of saccharin, 0.04 g of a flavoring agent, 4.0 g of ethanol, 0.4 g of sorbic acid, and water. The syrup thus obtained was transferred to a suitable container, and water was added to form a volume of 100 ml. The ingredients of the syrup are given in Table 11, below.

TABLE 11

| Ingredients | Contents |
|---|---|
| Hydrochloric acid salt of 5-(4-benzyloxy-4'-dimethylamino-biphenyl-3-ylmethylene)-2-thioxo-thiazolidin-4-one | 2 g |
| Saccharin | 0.8 g |
| Glucose | 25.4 g |
| Glycerin | 8.0 g |
| Flavoring agent | 0.04 g |
| Ethanol | 4.0 g |
| Sorbic Acid | 0.4 g |
| Distilled Water | Added to form a final volume of 100 ml |

2. Preparation of Tablet

A hydrochloric acid salt of 5-(4-benzyloxy-4'-dimethylamino-biphenyl-3-ylmethylene)-2-thioxo-thiazolidin-4-one was prepared from the rhodanine derivative synthesized in Example 5 using a typical process. 250 g of the hydrochloric acid salt, 175.9 g of lactose, 180 g of potato starch, and 32 g of colloidal silicate were mixed and added to a 10% gelatin solution. After being pulverized, the mixture was passed through a 14-sieve and dried. The powder thus obtained was mixed with 160 g of potato starch, 50 g of talc, and 5 g of magnesium stearate, and the mixture was subjected to a tabletting process. Ingredients of the tablet are given in Table 12, below.

TABLE 12

| Ingredients | Contents |
|---|---|
| Hydrochloric acid salt of 5-(4-benzyloxy-4'-dimethylamino-biphenyl-3-ylmethylene)-2-thioxo-thiazolidin-4-one | 250 g |
| Lactose | 175.9 g |
| Potato Starch | 180 g |
| Colloidal Silicate | 32 g |
| 10% Gelatin Sol'n | 50 ml |
| Potato Starch | 160 g |
| Mg Stearate | 5 g |
| Distilled Water | Suitable amount |

3. Preparation of Injection

A hydrochloric acid salt of 5-(4-benzyloxy-4'-dimethylamino-biphenyl-3-ylmethylene)-2-thioxo-thiazolidin-4-one was prepared from the indene derivative synthesized in Example 2 using a typical process. 1 g of the hydrochloric acid salt, 0.6 g of sodium chloride, and 0.1 g of ascorbic acid were dissolved in an amount of distilled water that formed a volume of 100 ml. The resulting solution was placed in a vial and sterilized at 20° C. for 30 min to prepare an injection. The ingredients of the injection are given in Table 13, below.

TABLE 13

| Ingredient | Contents |
|---|---|
| Hydrochloric acid salt of 5-(4-benzyloxy-4'-dimethylamino-biphenyl-3-ylmethylene)-2-thioxo-thiazolidin-4-one | 1 g |
| HCl | 0.6 g |
| Ascorbic Acid | 0.1 g |
| Distilled Water | Added to form a final volume of 100 ml |

INDUSTRIAL APPLICABILITY

Exhibiting potent inhibitory activity against protein phosphatase, the rhodanine derivatives or pharmaceutically acceptable salts thereof in accordance with the present invention are effective in the prevention and treatment of various phosphatase-related diseases, including autoimmune disease, diabetes, impaired glucose intolerance, insulin resistance, obesity, cancers, etc. when their activities are modulated.

The invention claimed is:

1. A rhodanine compound represented by the following Chemical Formula 1, or a pharmaceutically acceptable salt thereof:

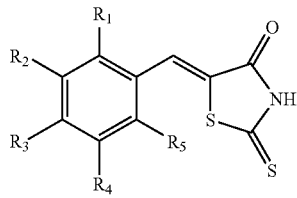

Chemical Formula 1 wherein, $R_1$ is one selected from the group consisting of:

phenyl-$C_2$-$C_6$ alkoxy, phenyl-$C_1$-$C_6$ alkoxy substituted with halogen, phenyl-$C_1$-$C_6$ alkoxy substituted with nitro, phenyl-$C_1$-$C_6$ alkoxy substituted with halogen and nitro, phenyl-$C_1$-$C_6$ alkoxy substituted with $C_1$-$C_6$ alkyl, phenyl-$C_1$-$C_6$ alkoxy substituted with $C_1$-$C_6$ alkoxy, phenyl-$C_1$-$C_6$ alkoxy substituted with $CF_3$, phenyl-$C_1$-$C_6$ alkoxy substituted with phenyl, nitro, phenoxy-$C_1$-$C_6$ alkoxy, phenoxy-$C_1$-$C_6$ alkoxy substituted with halogen, phenoxy-$C_1$-$C_6$ alkoxy substituted with cyano, phenoxy-$C_1$-$C_6$ alkoxy substituted with $C_1$-$C_6$ alkyl, phenoxy-$C_1$-$C_6$ alkoxy substituted with $C_1$-$C_6$ alkoxy, phenoxy-$C_1$-$C_6$ alkoxy substituted with 4-oxo-2-thioxo-thiazolidine, $C_1$-$C_6$ alkenyloxy, $C_1$-$C_6$ alkoxy substituted with benzhydryl, $C_1$-$C_6$ alkoxy substituted with benzoyl, $C_1$-$C_6$ alkoxy substituted with furan, $C_1$-$C_6$ alkoxy substituted with thiophene, $C_1$-$C_6$ alkoxy substituted with pyridine, $C_1$-$C_6$ alkoxy substituted with $C_1$-$C_6$ alkyl, $C_1$-$C_6$ alkoxy substituted with morpholine, $C_1$-$C_6$ alkoxy substituted with benzylpiperazine, $C_1$-$C_6$ alkoxy substituted with pyrrolidine, $C_1$-$C_6$ alkoxy substituted with tetrahydroisoquinoline, $C_1$-$C_6$ alkoxy substituted with imidazole, $C_1$-$C_6$ alkoxy substituted with carbazole, $C_1$-$C_6$ alkoxy substituted with acridine, oxy-$C_1$-$C_6$ alkoxy substituted with benzothiazole, oxy-$C_1$-$C_6$ alkoxy substituted with isoquinoline, oxy-$C_1$-$C_6$ alkoxy substituted with quinoline, oxy-$C_1$-$C_6$ alkoxy substituted with dibenzofuran, pyridine-oxy-$C_1$-$C_6$ alkoxy, pyridine-oxy-$C_1$-$C_6$ alkoxy substituted with $C_1$-$C_6$ alkyl, pyridine-oxy-$C_1$-$C_6$ alkoxy substituted with oxo, methylamino-$C_1$-$C_6$ alkoxy substituted with $C_1$-$C_6$ alkoxycarbonyl, methylamino-$C_1$-$C_6$ alkoxy substituted with acetyl, methylamino-$C_1$-$C_6$ alkoxy substituted with benzoyl, methylamino-$C_1$-$C_6$ alkoxy substituted with methanesulfonyl, methylamino-$C_1$-$C_6$ alkoxy substituted with benzenesulfonyl, methylaminocarbonylamino-$C_1$-$C_6$ alkoxy substituted with $C_1$-$C_6$ alkyl, methylaminocarbonylamino-$C_1$-$C_6$ alkoxy substituted with phenyl, methylaminocarbonylamino-$C_1$-$C_6$ alkoxy substituted with $C_1$-$C_6$ alkoxy, benzyl-NH—C(=S)-amino-$C_1$-$C_6$ alkoxy, phenoxy, phenoxy substituted with halogen, phenoxy substituted with cyano, morpholine, piperazine substituted with $C_1$-$C_6$ alkyl, piperazine substituted with benzyl, piperidine, pyrrolidine, $C_1$-$C_6$ alkylsulfonyl, and phenylsulfonyl substituted with $C_1$-$C_6$ alkyl or halogen;

$R_2$ is H, Br, or

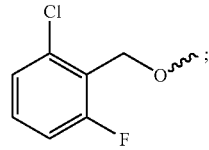

$R_3$ is one selected from the group consisting of:

H,

Halogen,

Hydroxyl, $C_1$-$C_6$ alkoxy substituted with halogen, $C_1$-$C_6$ alkoxy substituted with di($C_1$-$C_6$ alkyl)amine, $C_1$-$C_6$ alkoxy substituted with piperidine, $C_1$-$C_6$ alkoxy substituted with benzylpiperazine, $C_1$-$C_6$ alkoxy substituted with morpholine, $C_1$-$C_6$ alkoxy substituted with tetrahydroisoquinoline, $C_1$-$C_6$ alkoxy substituted with phenoxazine, $C_1$-$C_6$ alkoxy substituted with indole, $C_1$-$C_6$ alkoxy substituted with imidazole, $C_1$-$C_6$ alkoxy substituted with carbazole, $C_1$-$C_6$ alkoxy substituted with pyridine, amino-$C_1$-$C_6$ alkoxy substituted with phenxoxy-$C_1$-$C_6$ alkylcarbonyl, amino-$C_1$-$C_6$ alkoxy substituted with benzoyl, amino-$C_1$-$C_6$ alkoxy substituted with acetyl, amino-$C_1$-$C_6$ alkoxy substituted with phenylaminocarbonyl, amino-$C_1$-$C_6$ alkoxy substituted with benzylaminocarbonyl, amino-$C_1$-$C_6$ alkoxy substituted with methanesulfonyl, phenyl-$C_1$-$C_6$ alkoxy, phenyl-$C_1$-$C_6$ alkoxy substituted with halogen, di($C_1$-$C_6$ alkyl)amine, and phenyl substituted with di($C_1$-$C_6$ alkyl)amine;

$R_4$ is one selected from the group consisting of:

H, halo, $C_1$-$C_6$ alkoxy, phenyl-$C_1$-$C_6$ alkoxy, phenyl-$C_1$-$C_6$ alkoxy substituted with halogen, benzothiopene, benzofuran, phenyl substituted with $C_1$-$C_6$ alkoxy, phenyl substituted with di($C_1$-$C_6$ alkyl)amine and benzodioxole; and $R_5$ is H,

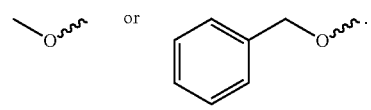

where, apart from the definition, $R_3$ and $R_4$ together may form a phenyl ring or a halogen-substituted phenyl ring, or $R_4$ and $R_5$ together may form a phenyl ring, and wherein $R_2$ to $R_5$ are not all hydrogen at the same time.

2. The rhodanine compound or the pharmaceutically acceptable salt as set forth in claim 1, wherein $R_1$ is one selected from the group consisting of substituents of the following Compound Group 1:

<Compound Group 1>
<Compound Group 1>
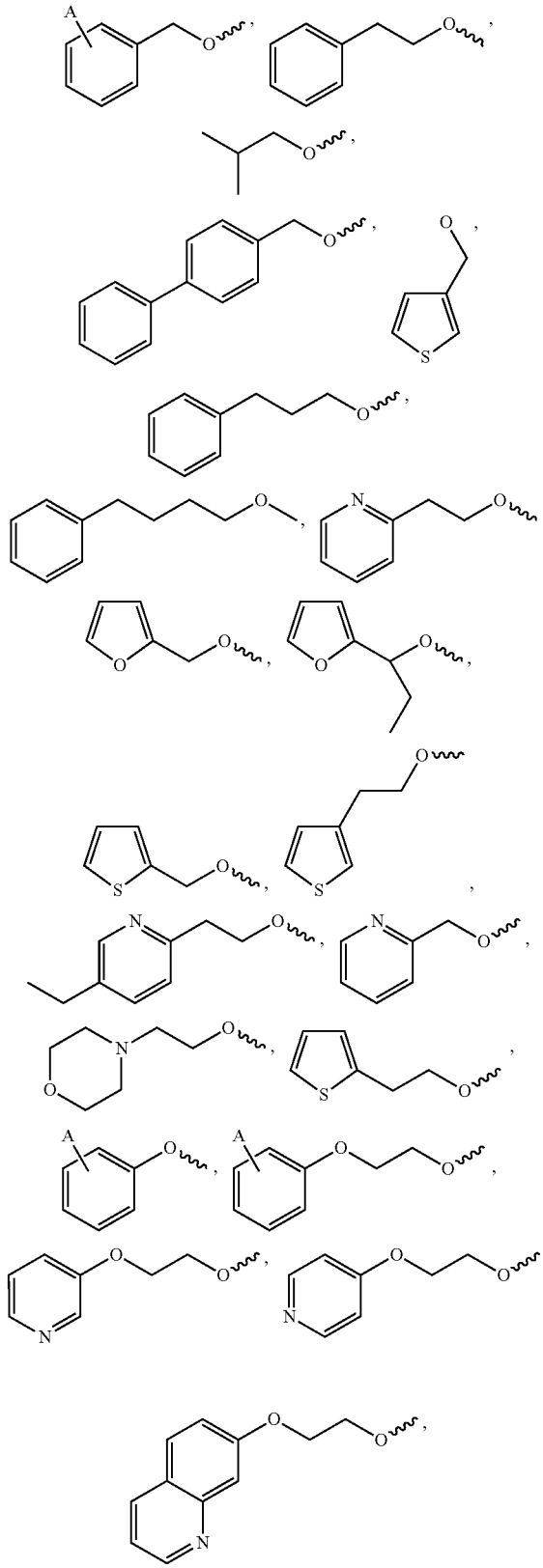
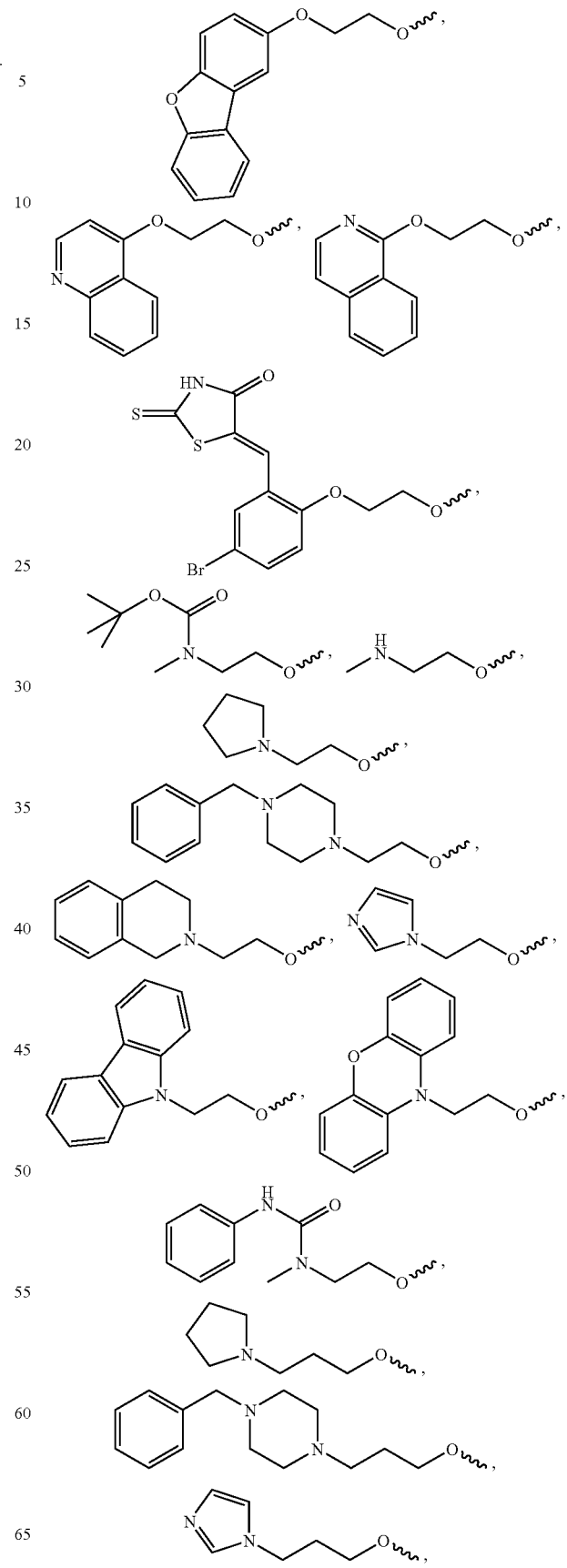

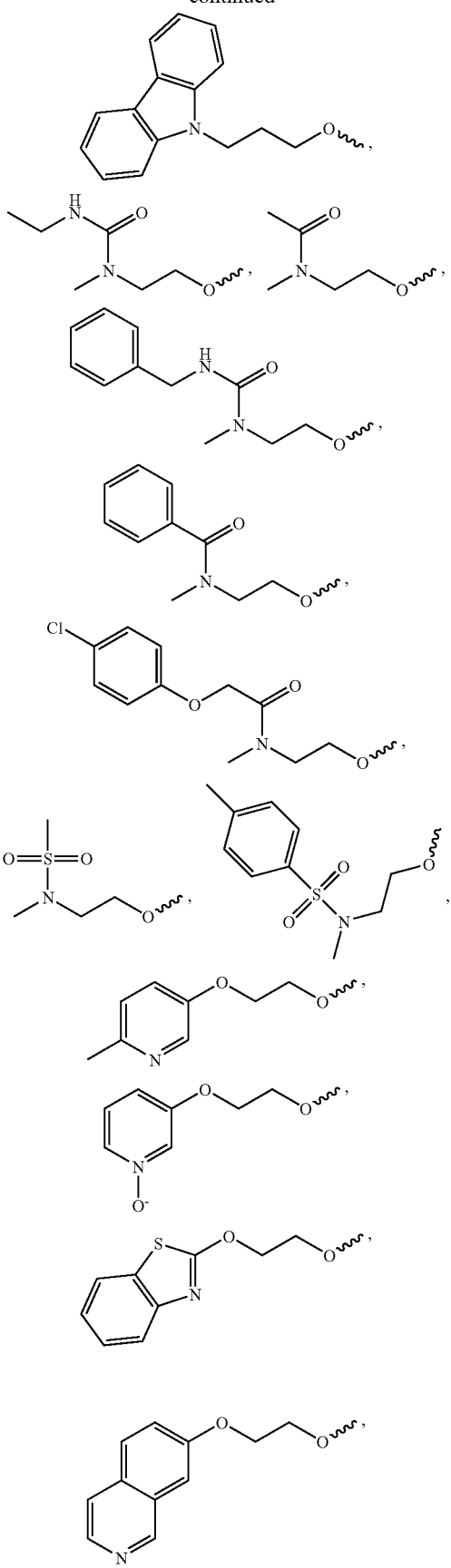
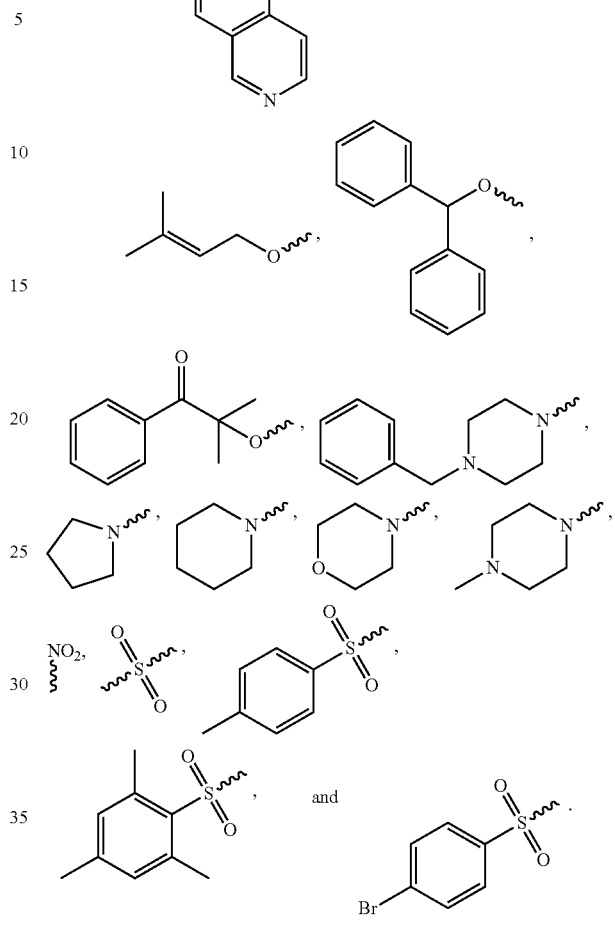
wherein A is one or two halogen atoms, $C_1$~$C_4$ alkyl, trifluoromethyl, cyano, or $C_1$~$C_4$ alkoxy.
3. The rhodanine compound or the pharmaceutically acceptable salt as set forth in claim 1, wherein $R_3$ is one selected from the group consisting of substituents of the following Compound Group 2:
<Compound Group 2>

-continued

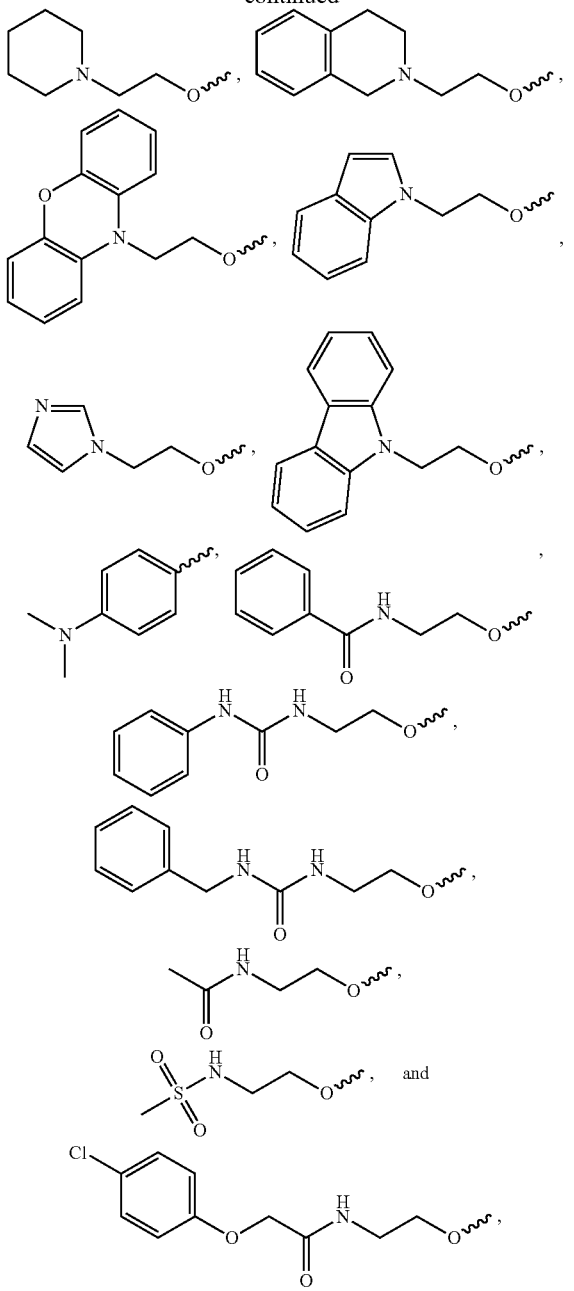

4. The rhodanine compound or the pharmaceutically acceptable salt as set forth in claim 1, wherein $R_4$ is one selected from the group consisting of substituents of the following Compound Group 3:

<Compound Group 3>

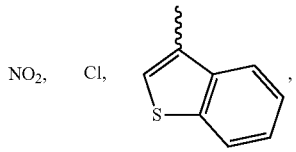

-continued

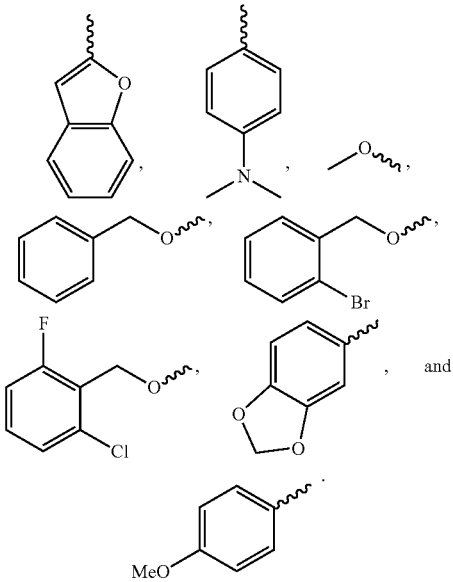

5. The rhodanine compound or the pharmaceutically acceptable salt as set forth in claim 1, wherein the rhodanine compound is one selected from the group consisting of;

4) 5-(5-bromo-2-phenethyloxy-benzylidene)-2-thioxo-thiazolidin-4-one,
5) 5-(5-bromo-2-isobutoxy-benzylidene)-2-thioxo-thiazolidin-4-one,
12) 5-[5-bromo-2-(4-chloro-2-nitro-benzyloxy)-benzylidene]-2-thioxo-thiazolidin-4-one,
13) 5-[5-bromo-2-(2-chloro-6-fluoro-benzyloxy)-benzylidene]-2-thioxo-thiazolidin-4-one,
14) 5-[5-bromo-2-(2-chloro-benzyloxy)-benzylidene]-2-thioxo-Thiazolidin-4-one,
15) 5-[5-bromo-2-(2,4-dichloro-benzyloxy)-benzylidene]-2-thioxo-thiazolidin-4-one,
16) 5-[5-bromo-2-(3,4-dichloro-benzyloxy)-benzylidene]-2-thioxo-thiazolidin-4-one,
17) 5-[5-bromo-2-(2,5-dimethyl-benzyloxy)-benzylidene]-2-thioxo-thiazolidin-4-one,
18) 5-[2-(biphenyl-ylmethoxy)-5-bromo-benzylidene]-2-thioxo-thiazolidin-4-one,
19) 5-[5-bromo-2-(3-trifluoromethyl-benzyloxy)-benzylidene]-2-thioxo-thiazolidin-4-one,
20) 5-[5-bromo-2-(3,5-dimethoxy-benzyloxy)-benzylidene]-2-thioxo-thiazolidin-4-one,
21) 5-[5-bromo-2-(2,6-difluoro-benzyloxy)-benzylidene]-2-thioxo-thiazolidin-4-one,
22) 5-[5-bromo-2-(4-bromo-benzyloxy)-benzylidene]-2-thioxo-thiazolidin-4-one,
23) 5-[5-bromo-2-(3-bromo-benzyloxy)-benzylidene]-2-thioxo-thiazolidin-4-one,
24) 5-[5-bromo-2-(2-bromo-benzyloxy)-benzylidene]-2-thioxo-thiazolidin-4-one,
25) 5-[5-bromo-2-(2-nitro-benzyloxy)-benzylidene]-2-thioxo-thiazolidin-4-one,
26) 5-[5-bromo-2-(3-phenyl-propoxy)-benzylidene]-2-thioxo-thiazolidin-4-one,
27) 5-[5-bromo-2-(5-phenyl-pentyloxy)-benzylidene]-2-thioxo-thiazolidin-4-one,
29) 5-[3-(2-chloro-6-fluoro-benzyloxy)-naphthalen-2-naphthalen-2-thioxo-thiazolidin-4-one, 30) 5-[3-(3,5-dimethoxy-benzyloxy)-naphthalen-2-ylmethylene]-2-thioxo-thiazolidin-4-one,
31) 5-[3-(biphenyl-4-ylmethoxy)-naphthalen-2-ylmethylene]-2-thioxo-thiazolidin-4-one,
33) 5-[2-(biphenyl-4-ylmethoxy)-4-diethylamino-benzylidene]-2-thioxo-thiazolidin-4-one,
34) 5-[2-(2-chloro-6-fluoro-benzyloxy)-4-diethylamino-benzylidene]-2-thioxo-thiazolidin-4-one,
35) 5-[4-diethylamino-2-(3,5-dimethoxy-benzyloxy)-benzylidene]-2-thioxo-thiazolidin-4-one,
36) 5-(4-diethylamino-2-phenethyloxy-benzylidene)-2-thioxo-thiazolidin-4-one,
37) 5-[2-(2-chloro-6-fluoro-benzyloxy)-naphthalen-1-ylmethylene]-2-thioxo-thiazolidin-4-one,
38) 5-[2-(3,5-dimethoxy-benzyloxy)-naphthalen-1-ylmethylene]-2-thioxo-thiazolidin-4-one,
39) 5-[5-bromo-2-(2-fluoro-benzyloxy)-benzylidene]-2-thioxo-thiazolidin-4-one,
40) 5-[5-bromo-2-(2-iodo-benzyloxy)-benzylidene]-2-thioxo-thiazolidin-4-one,
41) 5-[2-(2-bromo-benzyloxy)-naphthalen-1-ylmethylene]-2-thioxo-thiazolidin-4-one,
42) 5-(2-phenethyloxy-naphthalen-1-ylmethylene)-2-thioxo-thiazolidin-4-one,
43) 5-(5-chloro-2-nitro-benzylidene)-2-thioxo-thiazolidin-4-one,
44) 5-[2,4-bis-(2-bromo-benzyloxy)-benzylidene]-2-thioxo-thiazolidin-4-one,
45) 5-[2,3-bis-(2-chloro-6-fluoro-benzyloxy)-benzylidene]-2-thioxo-thiazolidin-4-one,
48) 5-[2-(2-bromo-benzyloxy)-4-hydroxy-benzylidene]-2-thioxo-thiazolidin-4-one,
50) 5-[2,5-bis-(2-bromo-benzyloxy)-benzylidene]-2-thioxo-thiazolidin-4-one,
51) 5-[2,5-bis-(2-chloro-6-fluoro-benzyloxy)-benzylidene]-2-thioxo-thiazolidin-4-one,
52) 5-5-bromo-2-[2-(5-bromo-2-(4-oxo-2-thioxo-thiazolidin-5-ylidenemethyl)-phenoxy)-ethoxy]-benzylidene-2-thioxo-thiazolidin-4-one,
53) 5-[5-bromo-2-(1-phenyl-ethoxy)-benzylidene]-2-thioxo-thiazolidin-4-one,
54) 5-[5-bromo-2-(3-methyl-but-2-enyloxy)-benzylidene]-2-thioxo-thiazolidin-4-one,
55) 5-[5-bromo-2-(1,1-dimethyl-2-oxo-2-methyllethoxy)-benzylidene]-2-thioxo-thiazolidin-4-one,
56) 5-(2-benzhydryloxy-5-bromo-benzylidene)-2-thioxo-thiazolidin-4-one,
57) 5-[5-bromo-2-(2-pyridin-2-yl-ethoxy)-benzylidene]-2-thioxo-thiazolidin-4-one,
58) 5-[5-bromo-2-(furan-2-ylmethoxy)-benzylidene]-2-thioxo-thiazolidin-4-one,
59) 5-[5-bromo-2-(thiopen-2-ylmethoxy)-benzylidene]-2-thioxo-thiazolidin-4-one,
60) 5-[5-bromo-2-(thiophen-3-ylmethoxy)-benzylidene]-2-thioxo-thiazolidin-4-one,
61) 5-[5-bromo-2-(2-thiophen-3-yl-ethoxy)-benzylidene]-2-thioxo-thiazolidin-4-one,
62) 5-5-bromo-2-[2-(5-ethyl-pyridin-2-yl)-ethoxy]-benzylidene-2-thioxo-thiazolidin-4-one
63) 5-[5-bromo-2-(pyridin-2-ylmethoxy)-benzylidene]-2-thioxo-thiazolidin-4-one,
64) 5-[5-bromo-2-(2-morpholin-4-yl-ethoxy)-benzylidene]-2-thioxo-thiazolidin-4-one,
65) 5-[5-bromo-2-(2-thiopen-2-yl-ethoxy)-benzylidene]-2-thioxo-thiazolidin-4-one,
66) 5-[5-bromo-2-(1-furan-2-yl-propoxy)-benzylidene]-2-thioxo-thiazolidin-4-one,
67) toluene-4-sulfonic acid 4-bromo-2-(4-oxo-2-thioxo-thiazolidin-5-ylidenemethyl)-phenyl ester,
68) methanesulfonic acid 4-bromo-2-(4-oxo-2-thioxo-thiazolidin-5-ylidenemethyl)-phenyl ester,
69) 2,4,6-trimethyl-benzenesulfonic acid-bromo-2-(4-oxo-2-thioxo-thiazolidin-5-ylidenemethyl)-phenyl ester,
70) 4-bromo-benzenesulfonic acid 4-bromo-2-(4-oxo-2-thioxo-thiazolidin-5-ylidenemethyl)-phenyl ester,
71) 5-(5-bromo-2-phenoxy-benzylidene)-2-thioxo-thiazolidin-4-one,
72) 5-(4-bromo-2-phenoxy-benzylidene)-2-thioxo-thiazolidin-4-one,
76) 5-(5-bromo-2-morpholin-4-ylbenzylidene)-2-thioxo-thiazolidin-4-one,
77) 5-[5-bromo-2-(2-bromo-phenoxy)-benzylidene]-2-thioxo-thiazolidin-4-one,
78) 5-[5-bromo-2-(3-bromo-phenoxy)-benzylidene]-2-thioxo-thiazolidin-4-one,
79) 5-[5-bromo-2-(4-bromo-phenoxy)-benzylidene]-2-thioxo-thiazolidin-4-one,
80) 2-[4-bromo-2-(4-oxo-2-thioxo-thiazolidin-5-ylidenemethyl)-phenoxy]-benzonitrile,
81) 5-[5-bromo-2-(2,4-dibromo-phenoxy)-benzylidene]-2-thioxo-thiazolidin-4-one,
82) 5-[2-(4-benzyl-piperazin-1-yl)-5-bromo-benzylidene]-2-thioxo-thiazolidin-4-one,
83) 5-(5-bromo-2-piperidin-1-yl-benzylidene)-2-thioxo-thiazolidin-4-one,
84) 5-(5-bromo-2-pyrrolidin-1-yl-benzylidene)-2-thioxo-thiazolidin-4-one,
85) 5-[4-bromo-2-(2-bromo-phenoxy)-benzylidene]-2-thioxo-thiazolidin-4-one,
86) 5-[4-bromo-2-(3-bromo-phenoxy)-benzylidene]-2-thioxo-thiazolidin-4-one,
87) 5-[2,4-bis-(4-bromo-phenoxy)-benzylidene]-2-thioxo-thiazolidin-4-one,
88) 5-[5-bromo-2-(4-methyl-piperazin-1-yl)-benzylidene]-2-thioxo-thiazolidin-4-one,
89) 2-[5-bromo-2-(4-oxo-2-thioxo-thiazolidin-5-ylidenemethyl)-phenoxy]-benzonitrile,
94) 5-[4-(2-chloro-6-fluoro-benzyloxy)-4'-dimethylamino-biphenyl-3-ylmethylene]-2-thioxo-thiazolidin-4-one,
95) 5-[4-(2-bromo-benzyloxy)-4'-dimethylamino-biphenyl-3-ylmethylene]-2-thioxo-thiazolidin-4-one,
96) 5-[4'-dimethylamino-4-(4-methoxy-benzyloxy)-biphenyl-3-ylmethylene]-2-thioxo-thiazolidin-4-one,
97) 5-(4'-dimethylamino-3-phenoxy-biphenyl-4-ylmethylene)-2-thioxo-thiazolidin-4-one,
99) 5-[4'-dimethylamino-4-(1-phenyl-ethoxy)-biphenyl-3-ylmethylene]-2-thioxo-thiazolidin-4-one,
100) 5-[5-benzo[1,3]dioxo-5-yl-2-(1-phenyl-ethoxy)-benzylidene]-2-thioxo-thiazolidin-4-one,
103) 5-[4'-dimethylamino-4-(3-methyl-but-2-enyloxy)-biphenyl-3-ylmethylene]-2-thioxo-thiazolidin-4-one,
104) 5-[4'-dimethylamino-4-(1,1-dimethyl-2-oxo-2-phenyl-ethoxy)-biphenyl-3-ylmethylene]-2-thioxo-thiazolidin-4-one,
105) 5-[5-benzo[1,3]dioxo-5-yl-2-(1,1-dimethyl-2-oxo-2-phenyl-ethoxy)-benzylidene]-2-thioxo-thiazolidin-4-one,
106) 5-(4-benzhydryloxy-4'-dimethylamino-biphenyl-3-ylmethylene)-2-thioxo-thiazolidin-4-one,
107) 5-(2-benzhydryloxy-5-benzo[1,3]dioxo-5-yl-benzylidene)-2-thioxo-thiazolidin-4-one, 108) 5-2-[2-(benzothiazol-2-yloxy)-ethoxy]-5-bromo-benzylidene-2-thioxo-thiazolidin-4-one,
109) 5-5-bromo-2-[2-(isoquinolin-5-yloxy)-ethoxy]-benzylidene-2-thioxo-thiazolidin-4-one
110) 5-5-bromo-2-[2-(isoquinolin-7-yloxy)-ethoxy]-benzylidene-2-thioxo-thiazolidin-4-one
111) 5-5-bromo-2-[2-(6-methyl-pyridin-3-yloxy)-ethoxy]-benzylidene-2-thioxo-thiazolidin-4-one,
112) 5-5-bromo-2-[2-(1-oxy-pyridin-3-yloxy)-ethoxy]-benzylidene-2-thioxo-thiazolidin-4-one,
113) 5-5-bromo-2-[2-(2-bromo-phenoxy)-ethoxy]-benzylidene-2-thioxo-thiazolidin-4-one,
114) 5-5-bromo-2-[2-(3-bromo-phenoxy)-ethoxy]-benzylidene-2-thioxo-thiazolidin-4-one,
115) 5-5-bromo-2-[2-(4-bromo-phenoxy)-ethoxy]-benzylidene-2-thioxo-thiazolidin-4-one,
116) 5-5-bromo-2-[2-(3,5-dibromo-phenoxy)-ethoxy]-benzylidene-2-thioxo-thiazolidin-4-one,
117) 2-2-[4-bromo-2-(4-oxo-2-thioxo-thiazolidin-5-ylidenemethyl)-phenoxy]-ethoxy-benzo nitrile,
118) 4-2-[4-bromo-2-(4-oxo-2-thioxo-thiazolidin-5-ylidenemethyl)-phenoxy]-ethoxy-benzo nitrile,
119) 5-5-bromo-2-[2-(2-chloro-phenoxy)-ethoxy]-benzylidene-2-thioxo-thiazolidin-4-one,
120) 5-5-bromo-2-[2-(4-chloro-phenoxy)-ethoxy]-benzylidene-2-thioxo-thiazolidin-4-one,
121) 5-5-bromo-2-[2-(3,5-dichloro-phenoxy)-ethoxy]-benzylidene-2-thioxo-thiazolidin-4-one,
122) 5-5-bromo-2-[2-(2-iodo-phenoxy)-ethoxy]-benzylidene-2-thioxo-thiazolidin-4-one,
123) 5-5-bromo-2-[2-(4-iodo-phenoxy)-ethoxy]-benzylidene-2-thioxo-thiazolidin-4-one,
124) 5-5-bromo-2-[2-(3-iodo-phenoxy)-ethoxy]-benzylidene-2-thioxo-thiazolidin-4-one,
125) 5-[5-bromo-2-(2-phenoxy-ethoxy)-benzylidene]-2-thioxo-thiazolidin-4-one,
126) 5-5-bromo-2-[2-(pyridin-3-yloxy)-ethoxy]-benzylidene-2-thioxo-thiazolidin-4-one,
127) 5-5-bromo-2-[2-(pyridin-4-yloxy)-ethoxy]-benzylidene-2-thioxo-thiazolidin-4-one,
128) 5-5-bromo-2-[2-(quinolin-7-yloxy)-ethoxy]-benzylidene-2-thioxo-thiazolidin-4-one,
129) 5-5-bromo-2-[2-(dibenzofuran-2-yloxy)-ethoxy]-benzylidene-2-thioxo-thiazolidin-4-one,
130) 5-5-bromo-2-[2-(4-methoxy-phenoxy)-ethoxy]-benzylidene-2-thioxo-thiazolidin-4-one,
131) 5-5-bromo-2-[2-(4-sec-butyl-phenoxy)-ethoxy]-benzylidene-2-thioxo-thiazolidin-4-one,
132) 5-5-bromo-2-[2-(2,6-dimethyl-phenoxy)-ethoxy]-benzylidene-2-thioxo-thiazolidin-4-one,
133) 5-5-chloro-2-[2-(4-methoxy-phenoxy)-ethoxy]-benzylidene-2-thioxo-thiazolidin-4-one,
134) 5-5-chloro-2-[3-(3,5-dimethyl-phenoxy)-propoxy]-benzylidene-2-thioxo-thiazolidin-4-one,
135) 5-5-bromo-2-[2-(quinolin-4-yloxy)-ethoxy]-benzylidene-2-thioxo-thiazolidin-4-one,
136) 5-5-bromo-2-[2-(isoquinolin-1-yloxy)-ethoxy]-benzylidene-2-thioxo-thiazolidin-4-one
137) 5-2-[2-(4-benzyl-piperazin-1-yl)-ethoxy]-5-bromo-benzylidene-2-thioxo-thiazolidin-4-one,
138) 5-[5-bromo-2-(2-pyrrolidin-1-yl-ethoxy)-benzylidene]-2-thioxo-thiazolidin-4-one,
139) 5-5-bromo-2-[2-(3,4-dihydro-1H-isoquinolin-2-yl)-ethoxy]-benzylidene-2-thioxo-thiazolidin-4-one,
140) 5-[5-bromo-2-(2-imidazol-1-yl-ethoxy)-benzylidene]-2-thioxo-thiazolidin-4-one,
141) 5-[5-bromo-2-(2-carbazol-9-yl-ethoxy)-benzylidene]-2-thioxo-thiazolidin-4-one,
142) 5-2-[2-(9H-acridin-10-yl)-ethoxy]-5-bromo-benzylidene-2-thioxo-thiazolidin-4-one,
143) 5-2-[3-(4-benzyl-piperazin-1-yl)-propoxy]-5-bromo-benzylidene-2-thioxo-thiazolidin-4-one,
144) 5-[5-bromo-2-(3-pyrrolidin-1-yl-propoxy)-benzylidene]-2-thioxo-thiazolidin-4-one,
145) 5-[5-bromo-2-(3-carbazol-9-yl-propoxy)-benzylidene]-2-thioxo-thiazolidin-4-one,
146) 5-[5-bromo-2-(3-imidazol-1-yl-propoxy)-benzylidene]-2-thioxo-thiazolidin-4-one,
147) 5-[2-(2-bromo-benzyloxy)-4-(2-bromo-ethoxy)-benzylidene]-2-thioxo-thiazolidin-4-one,
148) 5-[4-[2-(4-benzyl-piperazin-1-yl)-ethoxy]-2-(2-bromo-benzyloxy)-benzylidene]-2-thioxo-thiazolidin-4-one,
149) 5-[2-(2-bromo-benzyloxy)-4-(2-morpholin-4-yl-ethoxy)-benzylidene]-2-thioxo-thiazolidin-4-one,
150) 5-[2-(2-bromo-benzyloxy)-4-(2-diethylamino-ethoxy)-benzylidene]-2-thioxo-thiazolidin-4-one,
151) 5-[2-(2-bromo-benzyloxy)-4-(2-piperidin-1-yl-ethoxy)-benzylidene]-2-thioxo-thiazolidin-4-one,
152) 5-2-(2-bromo-benzyloxy)-4-[2-(3,4-dihydro-1H-isoquinolin-2-yl)-ethoxy]-benzylidene-2-thioxo-thiazolidin-4-one,
153) 5-[2-(2-bromo-benzyloxy)-4-(2-phenoxazin-10-yl-ethoxy)-benzylidene]-2-thioxo-thiazolidin-4-one,
154) 5-[2-(2-bromo-benzyloxy)-4-(2-indol-1-yl-ethoxy)-benzylidene]-2-thioxo-thiazolidin-4-one,
155) 5-[2-(2-bromo-benzyloxy)-4-(2-imidazol-1-yl-ethoxy)-benzylidene]-2-thioxo-thiazolidin-4-one,
156) 5-[2-(2-bromo-benzyloxy)-4-(2-carbazol-9-yl-ethoxy)-benzylidene]-2-thioxo-thiazolidin-4-one,
157) 2-[4-bromo-2-(4-oxo-2-thioxo-thiazolidin-5-ylidenemethyl)-phenoxy]-ethyl-methyl-carbamic acid t-butyl ester,
158) 5-[5-bromo-2-(2-methylamino-ethoxy)-benzylidene]-2-thioxo-thiazolidin-4-one; trifluoro acetic acid compound,
159) 1-2-[4-bromo-2-(4-oxo-2-thioxo-thiazolidin-5-ylidenemethyl)-phenoxy]-ethyl-1-methyl-3-phenyl-urea,
160) 1-2-[4-bromo-2-(4-oxo-2-thioxo-thiazolidin-5-ylidenemethyl)-phenoxy]-ethyl-3-(4-methoxy-phenyl)-1-methyl-urea,
161) 1-2-[4-bromo-2-(4-oxo-2-thioxo-thiazolidin-5-ylidenemethyl)-phenoxy]-ethyl-3-ethyl-1-methyl-urea,
162) N-2-[4-bromo-2-(4-oxo-2-thioxo-thiazolidin-5-ylidenemethyl)-phenoxy]-ethyl-N-methyl-acetamide,
163) 3-benzyl-1-2-[4-bromo-2-(4-oxo-2-thioxo-thiazolidin-5-ylidenemethyl)-phenoxy]-ethyl-1-methyl-thiourea,
164) N-2-[4-bromo-2-(4-oxo-2-thioxo-thiazolidin-5-ylidenemethyl)-phenoxy]-ethyl-N-methyl-benzamide,
165) N-2-[4-bromo-2-(4-oxo-2-thioxo-thiazolidin-5-ylidenemethyl)-phenoxy]-ethyl-2-(4-chloro-phenoxy)-N-methyl-acetamide,
166) N-2-[4-bromo-2-(4-oxo-2-thioxo-thiazolidin-5-ylidenemethyl)-phenoxy]-ethyl-N-methyl-methanesulfoneamide,
167) N-2-[4-bromo-2-(4-oxo-2-thioxo-thiazolidin-5-ylidenemethyl)-phenoxy]-ethyl-4,N-dimethyl-benzenesulfoneamide, 168) N-2-[3-(2-bromo-benzyloxy)-4-(4-oxo-2-thioxo-thiazolidin-5-ylidenemethyl)-phenoxy]-ethyl-2-(4-chloro-phenoxy)-acetamide, 169) N-2-[3-(2-bromo-benzyloxy)-4-(4-oxo-2-thioxo-thiazolidin-5-ylidenemethyl)-phenoxy]-ethyl-benzamide, 170) 1-2-[3-(2-bromo-benzyloxy)-4-(4-oxo-2-thioxo-thiazolidin-5-ylidenemethyl)-phenoxy]-ethyl-3-phenyl-urea, 171) 1-benzyl-3-2-[3-(2-bromo-benzyloxy)-4-(4-oxo-2-thioxo-thiazolidin-5-ylidenemethyl)-phenoxy]-ethyl-urea, 172) N-2-[3-(2-bromo-benzyloxy)-4-(4-oxo-2-thioxo-thiazolidin-5-ylidenemethyl)-phenoxy]-ethyl-acetamide, 173) N-2-[3-(2-bromo-benzyloxy)-4-(4-oxo-2-thioxo-thiazolidin-5-ylidenemethyl)-phenoxy]-ethyl-methane sulfoneamide, and 174) 5-[2-(2-bromo-benzyloxy)-4-(2-pyridin-2-yl-ethoxy)-benzylidene]-2-thioxo-thiazolidin-4-one.

6. A method for preparing a rhodanine compound, comprising:

(1) synthesizing an intermediate, represented by the following Chemical Formula 3, from a compound, represented by the following Chemical Formula 2 (step a); and (2) reacting the intermediate of Chemical Formula 3 with a rhodanine, represented by the following Chemical Formula 4, in the presence of sodium acetic and acetic acid to afford a rhodanine derivative represented by the following Chemical Formula 1 (step d):

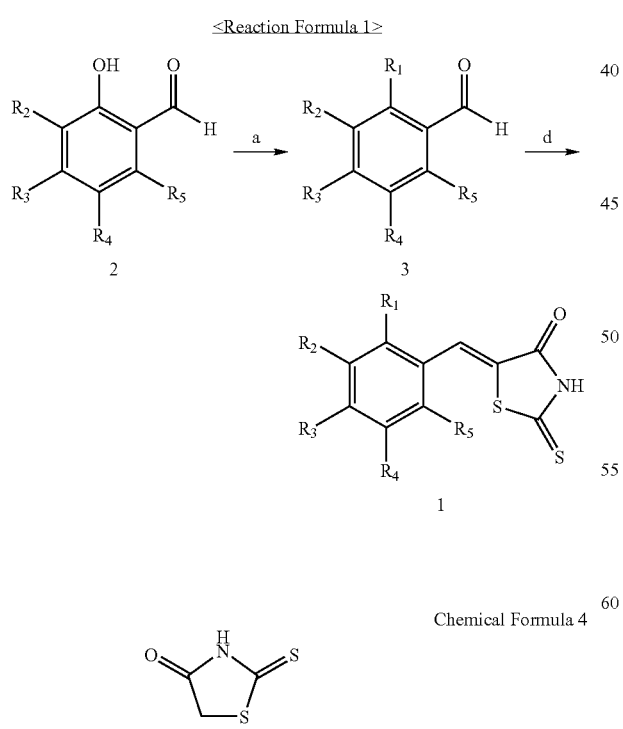

wherein $R_1$~$R_5$ are each as defined in claim 1.

7. The method as set forth in claim 6, wherein the step a is conducted by reacting the compound represented by Chemical Formula 2 of Reaction Formula 1 with a substituted alkyl or aryl bromide in the presence of a base in a nitrogen atmosphere to synthesize the intermediate represented by Chemical Formula 3 of Reaction Formula 1.

8. The method as set forth in claim 6, wherein the step a is conducted by introducing a substituent selected from among sulfide, ether and alkylamino into the compound represented by Chemical Formula 2 of Reaction Formula 1 through reaction with 1~3 equivalents of alcohol to synthesize the intermediate represented by Chemical Formula 3 of Reaction Formula 1.

9. The method as set forth in claim 6, wherein the step a is conducted by introducing a sulfonate group into the compound represented by Chemical Formula 2 of Reaction Formula 1 through reaction with sulfonyl chloride in the presence of 1~3 equivalents of pyridine or triethylamine to synthesize the intermediate represented by Chemical Formula 3 of Reaction Formula 1.

10. A method for preparing a rhodanine compound through routes of the following Reaction Formula 2, comprising:

1) synthesizing an intermediate represented by Chemical Formula 3 from a starting material represented by Chemical Formula 5 through reaction with an amine or phenol compound (step b); and 2) introducing the intermediate represented by Chemical Formula 3 into a rhodanine represented by Chemical Formula 4 of claim 6 in the presence of sodium acetate and acetic acid (step d):

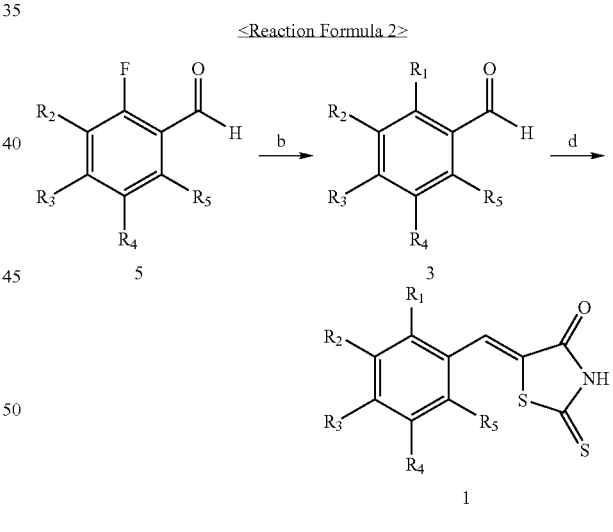

wherein $R_1$ to $R_5$ are each as defined in claim 1.

11. A method for preparing a rhodanine compound through routes of the following Reaction Formula 3, comprising;

1) synthesizing an intermediate represented by Chemical Formula 3 from a starting material represented by Chemical Formula 6 through reaction with boronic acid (step c); and 2) introducing the intermediate, represented by Chemical Formula 3, into rhodanine, represented by Chemical Formula 4 of claim 6, in the presence of sodium acetate and acetic acid (step d):

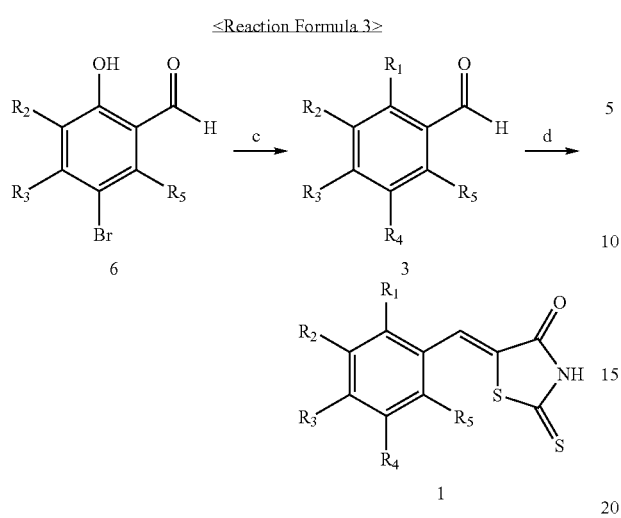

<Reaction Formula 3> wherein $R_1$ to $R_5$ are each as defined in claim 1.

12. A method for treating a diabetes mellitus or obesity caused by the activation of a protein phosphatase in a subject comprising administrating a therapeutically effective amount of the compound of claim 1 or a pharmaceutically acceptable salt thereof, to the subject, wherein the protein phosphatase is PTP1B, Prl-3, LAR, CD45, Cdc25A, Cdc25B, Cdc25C, Yop, PP1 or VHR protein phosphatase.

13. The method as set forth in claim 12, wherein the protein phosphatase is PTP1B or LAR protein phosphatase.

14. A rhodanine compound or the pharmaceutically acceptable salt thereof, wherein the rhodanine compound is one selected from the group consisting of:

2) 5-(3-benzyloxy-naphthalen-2-ylmethylene)-2-thioxothiazolidin-4-one;

3) 5-(2-benzyloxy-naphthalen-1-ylmethylene)-2-thioxo-thiazolidin-4-one;

6) 5-(3-benzyloxy-7-bromo-naphthalen-2-ylmethylene)-2-thioxo-thiazolidin-4-one;

7) 5-(2,4-bis-benzyloxy-benzylidene)-2-thioxo-thiazolidin-4-one;

9) 5-(2-benzyloxy-3-bromo-5-chloro-benzylidene)-2-thioxo-thiazolidin-4-one;

10) 5-(2-benzyloxy-6-methoxy-benzylidene)-2-thioxo-thiazolidin-4-one;

11) 2-thioxo-5-(2,4,6-tris-benzyloxy-benzylidene)-thiazolidin-4-one;

32) 5-(2-benzyloxy-4-diethylamino-benzylidene)-2-thioxo-thiazolidin-4-one;

46) 5-(2,3-bis-benzyloxy-benzylidene)-2-thioxo-thiazolidin-4-one;

73) 5-(2-morpholin-4-yl-benzylidene)-2-thioxo-thiazolidin-4-one, 74) 5-[2-(4-methyl-piperazin-1-yl)-benzylidene]-2-thioxo-thiazolidin-4-one, 75) 5-[2-(4-benzyl-piperazin-1-yl)-benzylidene]-2-thioxo-thiazolidin-4-one, 91) 5-(5-benzo[b]thiophen-3-yl-2-benzyloxy-benzylidene)-2-thioxo-thiazolidin-4-one;

92) 5-(5-benzofuran-2-yl-2-benzyloxy-benzylidene)-2-thioxo-thiazolidin-4-one;

93) 5-(4-benzyloxy-4'-dimethylamino-biphenyl-3-ylmethylene)-2-thioxo-thiazolidin-4-one;

98) 5-(4-benzyloxy-4'-methoxyethoxy-biphenyl-3-ylmethylene)-2-thioxo-thiazolidin-4-one, 101) 5-(4-benzyloxy-4'-dimethylamino-biphenyl-3-ylmethylene)-2-thioxo-thiazolidin-4-one; and 102) 5-(5-benzo[1,3]dioxo-5-yl-2-benzyloxy-benzylidene)-2-thioxo-thiazolidin-4-one.

\* \* \* \* \*